(12) United States Patent
Yoshida et al.

(10) Patent No.: US 8,653,125 B2
(45) Date of Patent: Feb. 18, 2014

(54) CYCLOHEXANE DERIVATIVE HAVING NPY Y5 RECEPTOR ANTAGONISM

(75) Inventors: Hiroshi Yoshida, Osaka (JP); Keisuke Tonogaki, Osaka (JP); Masahiro Sakagami, Osaka (JP); Kenji Takaya, Osaka (JP)

(73) Assignee: Shionogi Co., Ltd., Osaka-shi (JP)

( * ) Notice: Subject to any disclaimer, the term of this patent is extended or adjusted under 35 U.S.C. 154(b) by 231 days.

(21) Appl. No.: 13/254,702

(22) PCT Filed: Mar. 5, 2010

(86) PCT No.: PCT/JP2010/053663
§ 371 (c)(1),
(2), (4) Date: Sep. 2, 2011

(87) PCT Pub. No.: WO2010/101247
PCT Pub. Date: Sep. 10, 2010

(65) Prior Publication Data
US 2012/0004227 A1    Jan. 5, 2012

(30) Foreign Application Priority Data

Mar. 5, 2009  (JP) ................................ 2009-052065

(51) Int. Cl.
*A61K 31/4172*   (2006.01)
*A61K 31/165*    (2006.01)
*C07D 233/61*    (2006.01)
*C07C 233/30*    (2006.01)

(52) U.S. Cl.
USPC ......... 514/399; 548/345.1; 514/623; 564/191

(58) Field of Classification Search
USPC ................. 548/345.1; 564/191; 514/399, 623
See application file for complete search history.

(56) References Cited

U.S. PATENT DOCUMENTS

| | | | |
|---|---|---|---|
| 6,699,891 B1 | 3/2004 | Kawanishi et al. |
| 7,049,307 B2 | 5/2006 | Souers et al. |
| 7,067,509 B2 | 6/2006 | Goodfellow et al. |
| 7,223,788 B2 | 5/2007 | Schwink et al. |
| 7,265,130 B2 | 9/2007 | Kawanishi et al. |
| 7,504,412 B2 | 3/2009 | Kishino et al. |
| 7,534,892 B2 | 5/2009 | Nakatani |
| 7,781,461 B2 | 8/2010 | Kawanishi et al. |
| 2004/0176462 A1 | 9/2004 | Kawanishi et al. |
| 2004/0180964 A1 | 9/2004 | Kawanishi et al. |
| 2004/0220191 A1 | 11/2004 | Schwink et al. |
| 2005/0187279 A1 | 8/2005 | Souers et al. |
| 2006/0178403 A1 | 8/2006 | Goodfellow et al. |
| 2007/0010671 A1 | 1/2007 | Sekiguchi et al. |
| 2007/0015762 A1 | 1/2007 | Kawanishi et al. |
| 2007/0049593 A1 | 3/2007 | Oka et al. |
| 2007/0099929 A1 | 5/2007 | Thede et al. |
| 2007/0207991 A1 | 9/2007 | Schwink et al. |
| 2007/0287710 A1 | 12/2007 | Nakatani |
| 2009/0203712 A1 | 8/2009 | Yano |
| 2010/0004295 A1 | 1/2010 | Kouyama |
| 2010/0063027 A1 | 3/2010 | Okuno et al. |
| 2010/0267945 A1 | 10/2010 | Okuno et al. |
| 2010/0273841 A1 | 10/2010 | Okuno et al. |
| 2010/0273842 A1 | 10/2010 | Okuno et al. |
| 2010/0292500 A1 | 11/2010 | Kawanishi et al. |
| 2011/0028468 A1 | 2/2011 | Sakagami et al. |
| 2011/0039802 A1 | 2/2011 | Kawanishi et al. |

FOREIGN PATENT DOCUMENTS

| | | | | |
|---|---|---|---|---|
| EP | 1 249 233 A1 | 10/2002 | | |
| EP | 1 489 078 A1 | 12/2004 | | |
| EP | 1 657 242 A1 | 5/2006 | | |
| EP | 1657242 A1 * | 5/2006 | ........... C07D 471/04 |
| EP | 1 775 298 A1 | 4/2007 | | |
| JP | 6-220269 | 8/1994 | | |
| JP | 6-271762 | 9/1994 | | |
| JP | 2004-315511 | 11/2004 | | |
| JP | 2005-120080 | 5/2005 | | |
| JP | 2006 124387 | 5/2006 | | |
| JP | 2006 517563 | 7/2006 | | |
| JP | 2006 522109 | 9/2006 | | |

(Continued)

OTHER PUBLICATIONS

U.S. Appl. No. 13/254,750, filed Sep. 2, 2011, Sakagami, et al.
International Search Report issued Jun. 8, 2010 in PCT/JP10/53663 filed Mar. 5, 2010.
International Preliminary Report on Patentability and Written Opinion of the Internatinal Searching Authority issued Sep. 15, 2011, in PCT/JP2010/053663.
Lars Grundemar, et al., "Neuropeptide Y effector systems: perspectives for drug development", Trends in Pharmacological Sciences Reviews, vol. 15, May 1994, pp. 153-159.

(Continued)

*Primary Examiner* — Kamal A Saeed
*Assistant Examiner* — Janet L Coppins
(74) *Attorney, Agent, or Firm* — Oblon, Spivak, McClelland, Maier & Neustadt, L.L.P.

(57) ABSTRACT

The present invention discloses novel cyclohexane derivatives having NPY Y5 receptor antagonistic activity. Specifically, the present invention discloses a compound represented by the formula (I), or a pharmaceutically acceptable salt or a solvate thereof:

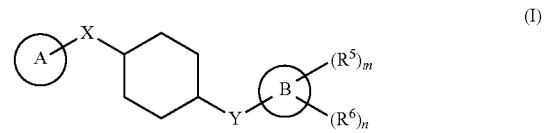

(I)

wherein A is substituted or unsubstituted aryl or heterocyclyl; a combination of X and Y is a combination selected from (X, Y)=(C(=O)N($R^1$), C(=O)N($R^2$)), (C(=O)N($R^1$), imidazole-1,3-diyl), (N($R^1$), C(=O)N($R^2$)), (O, C(=O)N($R^2$)), (C($R^3$)($R^4$), N($R^2$)) or (a single bond, C(=O)N($R^2$)); $R^1$, $R^2$ and $R^3$ are independently hydrogen or substituted or unsubstituted alkyl; $R^5$ is substituted or unsubstituted aryl or heterocyclyl; $R^6$ is halogen, oxo, substituted or unsubstituted alkyl, substituted or unsubstituted alkoxy, substituted or unsubstituted aryloxy; m is 0 or 1; and n is an integer of 0 to 5; and B is aromatic carbocycle, monocyclic heterocycle or fused bicyclic heterocycle.

18 Claims, No Drawings

(56) References Cited

FOREIGN PATENT DOCUMENTS

| | | |
|---|---|---|
| JP | 2007 91649 | 4/2007 |
| WO | 97 20823 | 6/1997 |
| WO | WO 98/22432 A1 | 5/1998 |
| WO | WO 01/02379 A1 | 1/2001 |
| WO | 01 37826 | 5/2001 |
| WO | WO 03/010175 A2 | 2/2003 |
| WO | WO 03/010175 A3 | 2/2003 |
| WO | WO 03/028641 A2 | 4/2003 |
| WO | WO 03/028641 A3 | 4/2003 |
| WO | WO 03/104255 A2 | 12/2003 |
| WO | WO 03/104255 A3 | 12/2003 |
| WO | 2004 080411 | 9/2004 |
| WO | 2004 081005 | 9/2004 |
| WO | 2004 089919 | 10/2004 |
| WO | WO 2004/087680 A1 | 10/2004 |
| WO | 2005 016928 | 2/2005 |
| WO | WO 2006/014482 A1 | 2/2006 |
| WO | 2007 125952 | 11/2007 |
| WO | 2008 026564 | 3/2008 |
| WO | WO 2009/106531 A1 | 9/2009 |
| WO | WO 2009/153720 A1 | 12/2009 |

OTHER PUBLICATIONS

Catalina Betancur, et al., "Nonpeptide antagonists of neuropeptide receptors: tools for research and therapy", Trends in Pharmacological Sciences Reviews, vol. 18, Oct. 1997, pp. 372-386.

Ambikaipakan Balasubramaniam, "Neuropeptide Y Family of Hormones: Receptor Subtypes and Antagonists", Peptides, vol. 18, No. 3, 1997, pp. 445-457.

Thomas J. Lukas, et al., Identification of Novel Classes of Protein Kinase Inhibitors Using Combinatorial Peptide Chemistry Based on Functional Genomics Knowledge, Jorunal of Medicinal Chemistry, vol. 42, 1999, pp. 910-919.

Seiichiro Tabuchi, et al., "Novel Potent Antagonists of Human Neuropeptide Y Y5 Receptor. Part 1: 2-Oxobenzothiazolin-3-acetic Acid Derivatives", Bioorganic & Medicinal Chemistry Letters, vol. 12, 2002, pp. 1171-1175.

* cited by examiner

CYCLOHEXANE DERIVATIVE HAVING NPY Y5 RECEPTOR ANTAGONISM

TECHNICAL FIELD

The present invention relates to a novel cyclohexane derivatives having NPY Y5 receptor antagonistic activity.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an antistress activity, etc. in central nervous system, and it may be pivotally involved in the central nervous system diseases such as depression, Alzheimer-type dementia and Parkinson's disease. NPY is thought to be associated with circulatory disorders, since it induces a contraction of smooth muscles such as blood vessels or cardiac muscles in the peripheral tissues. Furthermore, NPY is also known to be involved in the metabolic diseases such as obesity, diabetes and hormone abnormalities (Non-patent Document 1). Therefore, an NPY receptor antagonist is expected as a medicine for preventing or treating various diseases involved in the NPY receptor like the above.

As to NPY receptor, Y1, Y2, Y3, Y4, Y5, and Y6 subtypes have been identified (Non-patent Document 2). It has been suggested that Y5 receptor is at least involved in the feeding behavior and its antagonist is expected as an anti-obesity agent (Non-patent Document 3).

As a NPY Y5 receptor antagonist, WO2001/2379 (Patent Document 1) disclose compounds having a tricyclic condensed hetero ring, JP2003-137872 (Patent Document 2) discloses substituted 2-cyclohexylyl-4-phenyl-1H-imidazole derivatives, WO97/20823 (Patent Document 3) discloses cyclohexane derivatives connecting aryl via methylenecarbonyl group, WO2004/89919 (Patent Document 4) discloses cyclohexanecarboxamido derivatives having a substituted dihydrobenzoxazolyl or substituted dihydrooxazolopyridy, WO2003/010175 (Patent Document 15) and Bioorganic & Medicinal Chemistry Letters (2002), 12(8), 1171-1175 (Non-patent Document 5) discloses cyclohexanecarboxamido derivatives substituted with hydroxy, WO2006/14482 (Patent Document 5) discloses pyrimidine derivatives connecting cyclohexane via iminomethylene group, WO01/37826 (Patent Document 6) and WO2006/001318 (Patent Document 7) disclose sulphonamide compounds, WO2007/125952 (Patent Document 8) and WO2009/054434 (Patent Document 13) disclose amine derivatives, WO2008/026563 (Patent Document 9) discloses hydrazineamide derivatives, WO2008/026564 (Patent Document 10) discloses urea derivatives, WO2009/131096 (Patent Document 14) discloses compounds having a monocyclic or bicyclic aromatic hetero ring. These compounds differ from the compound of the invention in structure.

Also, compounds having a similar structure to the compound of the present invention are disclosed in WO2003/028641 (Patent Document 11), JP2004-315511 (Patent Document 12), WO2004/072025 (Patent Document 16), WO2009/153720 (Patent Document 17), WO2009/106531 (Patent Document 18), WO2006/004040 (Patent Document 19), WO2005/080399 (Patent Document 20), WO2005/063734 (Patent Document 21), JP2005-120080 (Patent Document 22), WO2003/082847 (Patent Document 23), WO98/22432 (Patent Document 24), JP6-271762 (Patent Document 25), JP6-220269 (Patent Document 26), etc. However, these documents do not describe NPY Y5 receptor antagonism to suggest the present invention.

[Patent Document 1] WO2001/2379
[Patent Document 2] JP2003-137872
[Patent Document 3] WO97/20823
[Patent Document 4] WO2004/89919
[Patent Document 5] WO2006/14482
[Patent Document 6] WO01/37826
[Patent Document 7] WO2006/001318
[Patent Document 8] WO2007/125952
[Patent Document 9] WO2008/026563
[Patent Document 10] WO2008/026564
[Patent Document 11] WO2003/028641
[Patent Document 12] JP2004-315511
[Patent Document 13] WO2009/054434
[Patent Document 14] WO2009/131096
[Patent Document 15] WO2003/010175
[Patent Document 16] WO2004/072025
[Patent Document 17] WO2009/153720
[Patent Document 18] WO2009/106531
[Patent Document 19] WO2006/004040
[Patent Document 20] WO2005/080399
[Patent Document 21] WO2005/063734
[Patent Document 22] JP2005-120080
[Patent Document 23] WO2003/082847
[Patent Document 24] WO98/22432
[Patent Document 25] JP6-271762
[Patent Document 26] JP6-220269
[Non-patent Document 1] Trends in Pharmacological Sciences, Vol. 15, 153 (1994)
[Non-patent Document 2] Trends in Pharmacological Sciences, Vol. 18, 372 (1997)
[Non-patent Document 3] Peptides, Vol. 18, 445 (1997)
[Non-patent Document 4] Journal of Medicinal Chemistry (1999), 42(5), 910-919
[Non-patent Document 5] Bioorganic & Medicinal Chemistry Letters (2002), 12(8), 1171-1175

DISCLOSURE OF INVENTION

Problems to be Solved by the Invention

The objection of the present invention is to provide excellent new compounds having NPY Y5 receptor antagonistic activity.

Means for Solving the Problem

The present invention provides the followings.
[1] A compound of the formula (I):

[Chemical Formula 1]

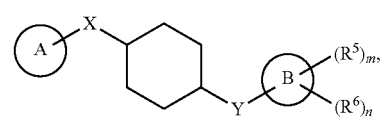

a pharmaceutically acceptable salt or solvate thereof, wherein
A is substituted or unsubstituted aryl or substituted or unsubstituted heterocyclyl;
X and Y are any one selected from the following combinations:

(X, Y)=(C(=O)N(R$^1$), C(=O)N(R$^2$))
(C(=O)N(R$^1$), imidazole-1,3-diyl)
(N(R$^1$), C(=O)N(R$^2$))
(O, C(=O)N(R$^2$))
(C(R$^3$)(R$^4$), N(R$^2$)) or
(a single bond, C(=O)N(R$^2$))
wherein R$^1$, R$^2$, R$^3$ and R$^4$ are independently hydrogen or substituted or unsubstituted alkyl;

B is aromatic carbocycle, monocyclic heterocycle or fused bicyclic heterocycle;

R$^5$ is substituted or unsubstituted aryl or substituted or unsubstituted heterocyclyl;

R$^6$ is each independently selected from the group consisting of:

halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5;

provided that a compound wherein A is substituted dihydrobenzoxazolyl or substituted dihydrooxazolopyridyl is excluded.

[2] The compound, pharmaceutically acceptable salt or solvate thereof according to [1] wherein the combination of X and Y is (X, Y)=(C(=O)N(R$^1$), C(=O)N(R$^2$)) or (C(=O)N(R$^1$), imidazole-1,3-diyl).

[3] The compound, pharmaceutically acceptable salt or solvate thereof according to [1] wherein the combination of X and Y is (X, Y)=(N(R$^1$), C(=O)N(R$^2$)) or (O, C(=O)N(R$^2$)).

[4] The compound, pharmaceutically acceptable salt or solvate thereof according to [1] wherein the combination of X and Y is (X, Y)=(C(R$^3$)(R$^4$), N(R$^2$)).

[5] The compound, pharmaceutically acceptable salt or solvate thereof according to [1] wherein the combination of X and Y is (X, Y)=(a single bond, C(=O)N(R$^2$)).

[6] The compound, pharmaceutically acceptable salt or solvate thereof according to any one of [1] to [5] wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzoisothiazolyl, or substituted or unsubstituted benzoxathiazolyl.

[7] The compound, pharmaceutically acceptable salt or solvate thereof according to any one of [1] to [6] wherein B is benzene, pyrazole, imidazole, pyridine, pyradine, indazole or dihydrobenzoxazole.

[8] The compound, pharmaceutically acceptable salt or solvate thereof according to any one of [1] to [7] wherein m is 1.

[9] The compound, pharmaceutically acceptable salt or solvate thereof according to [8] wherein R$^5$ is substituted or unsubstituted phenyl, substituted or unsubstituted pyridyl, or substituted or unsubstituted morpholino.

[10] The compound, pharmaceutically acceptable salt or solvate thereof according to any one of [1] to [7] wherein n is 1 and m is 0.

[11] The compound, pharmaceutically acceptable salt or solvate thereof according to any one of [1] to [10] wherein R$^6$ is halogen, oxo, substituted or unsubstituted alkyl, substituted or unsubstituted alkoxy, or substituted or unsubstituted aryloxy.

[12] A pharmaceutical composition comprising the compound, a pharmaceutically acceptable salt or solvate thereof according to any one of [1] to [11] as an active ingredient.

[13] An NPY Y5 receptor antagonist comprising the compound, a pharmaceutically acceptable salt or solvate thereof according to any one of [1] to [11] as an active ingredient.

[14] A pharmaceutical composition having NPY Y5 receptor antagonistic activity comprising a compound of the formula (I):

[Chemical Formula 2]

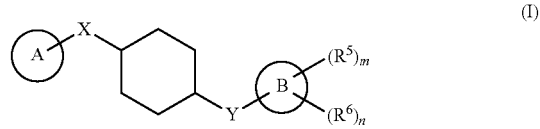

(I)

a pharmaceutically acceptable salt or solvate thereof, wherein

A is substituted or unsubstituted aryl or substituted or unsubstituted heterocyclyl;

the group of the formula:

[Chemical Formula 3]

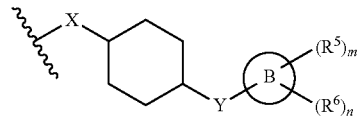

is any one of the following groups:

[Chemical Formula 4]

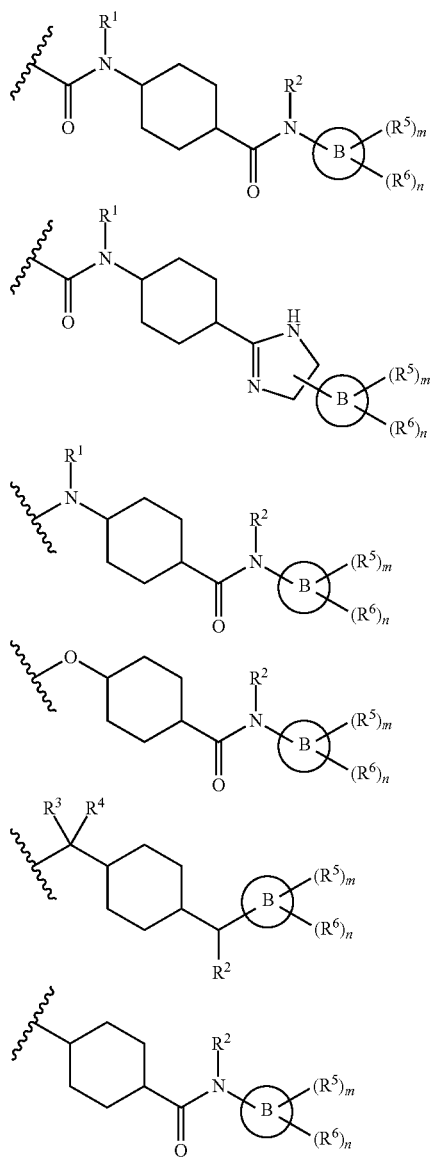

in which $R^1$, $R^2$, $R^3$ and $R^4$ are independently hydrogen or substituted or unsubstituted alkyl;

B is aromatic carbocycle, monocyclic heterocycle or fused bicyclic heterocycle;

$R^5$ is substituted or unsubstituted aryl or substituted or unsubstituted heterocyclyl;

$R^6$ is each independently selected from the group consisting of:

halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5, provided that a compound wherein A is substituted dihydrobenzoxazolyl or substituted dihydrooxazolopyridyl is excluded.

[15] The pharmaceutical composition having NPY Y5 receptor antagonistic activity according to [14] wherein the group of the formula:

[Chemical Formula 5]

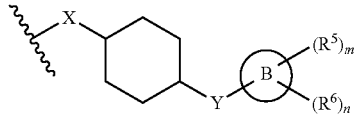

is

[Chemical Formula 6]

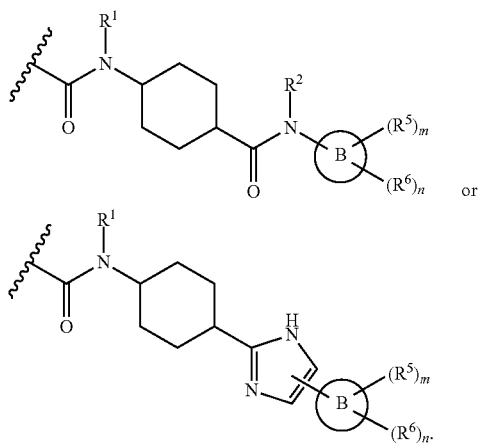

[16] The pharmaceutical composition having NPY Y5 receptor antagonistic activity according to [14] wherein the group of the formula:

[Chemical Formula 7]

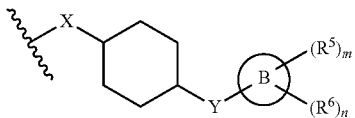

is

[Chemical Formula 8]

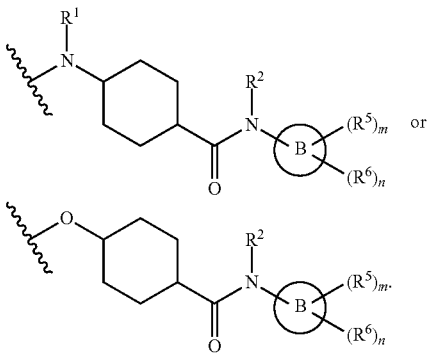

[17] The pharmaceutical composition having NPY Y5 receptor antagonistic activity according to [14] wherein the group of the formula:

[Chemical Formula 9]

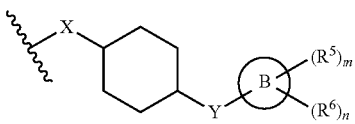

is

[Chemical Formula 10]

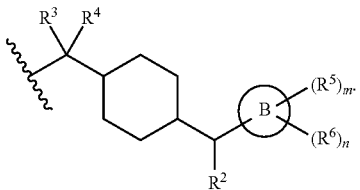

[18] The pharmaceutical composition having NPY Y5 receptor antagonistic activity according to [14] wherein the group of the formula:

[Chemical Formula 11]

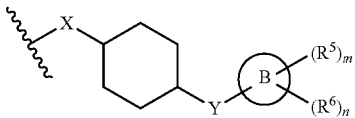

is

[Chemical Formula 12]

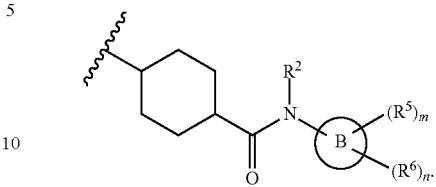

[19] The pharmaceutical composition having NPY Y5 receptor antagonistic activity according to any one of [14] to [18] wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzoisothiazolyl, or substituted or unsubstituted benzoxathiazolyl.

[20] The pharmaceutical composition having NPY Y5 receptor antagonistic activity according to any one of [14] to [19] wherein B is benzene, pyrazole, imidazole, pyridine, pyradine, indazole or dihydrobenzoxazole.

[21] The pharmaceutical composition having NPY Y5 receptor antagonistic activity according to any one of [14] to [20] wherein m is 1.

[22] The pharmaceutical composition having NPY Y5 receptor antagonistic activity according to [21] wherein $R^5$ is substituted or unsubstituted phenyl, substituted or unsubstituted pyridyl, or substituted or unsubstituted morpholino.

[23] The pharmaceutical composition having NPY Y5 receptor antagonistic activity according to any one of [14] to [20] wherein n is 1 and m is 0.

[24] The pharmaceutical composition having NPY Y5 receptor antagonistic activity according to any one of [14] to [23] wherein $R^6$ is halogen, oxo, substituted or unsubstituted alkyl, substituted or unsubstituted alkoxy, or substituted or unsubstituted aryloxy.

[25] The pharmaceutical composition having NPY Y5 receptor antagonistic activity according to any one of [1] to [24] for use in the prevention or treatment of obesity or obesity-related diseases, or weight control in obesity.

[26] A compound of the formula (II):

[Chemical Formula 13]

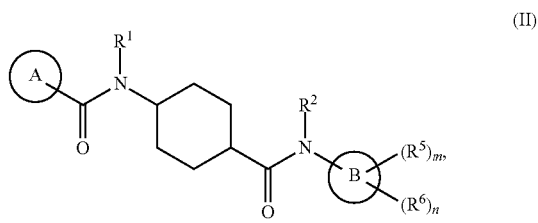

(II)

a pharmaceutically acceptable salt or solvate thereof, wherein
A is substituted or unsubstituted phenyl, substituted or unsubstituted thiazolyl, substituted or unsubstituted oxazolyl, substituted or unsubstituted isoxazolyl, substituted or unsubstituted pyridyl, substituted or unsubstituted naphthyridyl, or substituted or unsubstituted quinolyl;

R$^1$ and R$^2$ are independently hydrogen or substituted or unsubstituted alkyl;

B is benzene, pyrazole, pyridine, pyradine, indazole or dihydrobenzoxazole, provided that B is not benzene when A is substituted or unsubstituted phenyl;

R$^5$ is substituted or unsubstituted aryl or substituted or unsubstituted heterocyclyl;

R$^6$ is each independently selected from the group consisting of:

halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5.

[27] A compound of the formula (III):

[Chemical Formula 14]

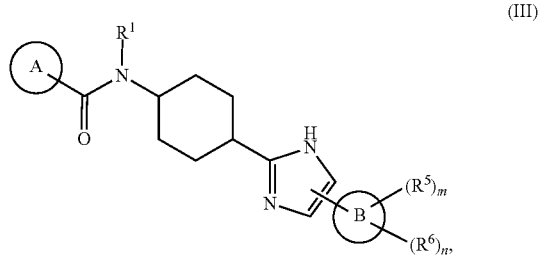

(III)

a pharmaceutically acceptable salt or solvate thereof, wherein

A is substituted or unsubstituted aryl or substituted or unsubstituted heterocyclyl;

R$^1$ is hydrogen or substituted or unsubstituted alkyl;

B is aromatic carbocycle, monocyclic heterocycle or fused bicyclic heterocycle;

R$^5$ is substituted or unsubstituted aryl or substituted or unsubstituted heterocyclyl;

R$^6$ is each independently selected from the group consisting of:

halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5.

[28] A compound of the formula (IV):

[Chemical Formula 15]

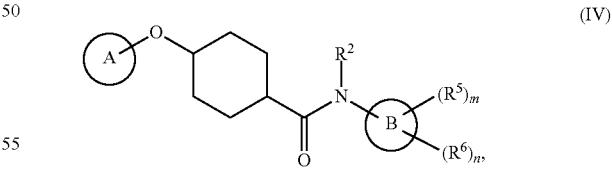

(IV)

a pharmaceutically acceptable salt or solvate thereof, wherein

A is substituted or unsubstituted aryl or substituted or unsubstituted heterocyclyl;

R$^2$ is hydrogen or substituted or unsubstituted alkyl;

B is aromatic carbocycle, monocyclic heterocycle or fused bicyclic heterocycle;

R$^5$ is substituted or unsubstituted aryl or substituted or unsubstituted heterocyclyl;

each of R$^6$ is independently selected from the group consisting of:

halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and
n is an integer of 0 to 5.

[29] A pharmaceutical composition comprising the compound, a pharmaceutically acceptable salt or solvate thereof according to any one of [26] to [28].
[30] Use of a compound, a pharmaceutically acceptable salt or solvate thereof according to any one of [1] to [28] for the manufacture of an NPY Y5 receptor antagonist.
[31] Use of a compound, a pharmaceutically acceptable salt or solvate thereof according to any one of [1] to [28] for the manufacture of a pharmaceutical composition for use in the prevention or treatment of obesity or obesity-related diseases, or weight control in obesity.
[32] Use of a compound, a pharmaceutically acceptable salt or solvate thereof according to any one of [1] to [28] for the manufacture of an anorectic agent.
[33] A compound, a pharmaceutically acceptable salt or solvate thereof according to any one of [1] to [28] for use in a method of prevention or treatment of a disease involving NPY Y5 receptor.
[34] A compound, a pharmaceutically acceptable salt or solvate thereof according to any one of [1] to [28] for use in the prevention or treatment of obesity or obesity-related diseases, or weight control in obesity.
[35] A method for the prevention or treatment of a disease involving NPY Y5 receptor, which comprises a step of administrating a compound, a pharmaceutically acceptable salt or solvate thereof according to any one of [1] to [28].
[36] A method for prevention or treatment of obesity, obesity-related diseases, or weight control in obesity, which comprises a step of administrating a compound, a pharmaceutically acceptable salt or solvate thereof according to any one of [1] to [28].

Effect of the Invention

The compound of the present invention having the formula (I) has an antagonistic activity against NPY Y5 receptor. Furthermore, the compound of the present invention is useful for a medicament and has any or all of the excellent features listed below.
a) Good pharmacokinetic such as high transportability through the blood-brain barrier.
b) High selectivity for Y5 receptor.
c) High metabolic stability.
d) Weak CYP enzyme (e.g., CYP1A2, CYP2C9, CYP3A4, etc.) inhibition.
e) Less induction of a drug-metabolizing enzyme.
f) Low toxicity, such as less anemia-inducing activity.
g) Good pharmacokinetics, such as high bioavailability and adequate drug clearance.
h) High water-solubility.

The compound of the present invention exhibits NPY Y5 receptor antagonistic activity and are very useful as a medicament, especially for the treatment and/or prevention of diseases involving NPY Y5, such as feeding disorder, obesity, hyperorexia, sexual disorder, impaired fertility, depression, epileptic seizure, hypertension, cerebral hemorrhage, congestive heart failure or sleep disorders, etc. Also, the compound of the present invention exhibits efficient anorectic activity, and thus, very useful in weight control in obesity, reduction of body weight, maintaining of weight after weight reduction. Moreover, the compound of the invention is useful for the treatment and/or prevention of the diseases in which obesity acts as a risk factor, such as diabetes, hypertension, dyslipidemia, atherosclerosis and acute coronary syndrome.

BEST MODE FOR CARRYING OUT THE INVENTION

As used herein, the term "halogen" includes fluorine, chlorine, bromine and iodine. In particular, fluorine and chlorine are preferable.

The term "alkyl" which is used alone or in combination with the other term means a straight or branched chain alkyl and includes, for example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecyl, n-dodecyl, n-tridecyl, n-tetradecyl, n-pentadecyl, etc.

The term "alkenyl" includes a straight or branched chain alkenyl having one or more double bonds in the above "alkyl" containing 2 to 10 carbon atoms, preferably 2-8 carbon atoms, and more preferably 3 to 6 carbon atoms. The alkenyl includes, for example, vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, etc.

The term "alkynyl" means a straight or branched chain alkynyl having one or more triple bonds in the above "alkyl" and containing 2 to 8 carbon atoms and includes, for example, ethynyl, 1-propynyl, 2-propynyl, 1-buthynyl, 2-buthynyl, 3 buthynyl, etc.

The term "aromatic carbocycle" is a mono- or poly-cyclic aromatic carbocyclic ring and includes, for example, benzene ring, naphthalene ring, anthracene ring, phenanthrene ring, indene ring, etc. In particular, benzene ring and naphthalene ring are preferable.

The term "aryl" is a group obtained by removing a hydrogen from the above aromatic carbocycle and includes, for example, phenyl, naphthyl, anthryl, phenanthryl, indenyl, etc.

The term "heterocyclyl" includes a heterocyclic group having one or more heteroatoms selected from O, S and N in the ring and includes 5- or 6-membered heteroaryl such as pyrrolyl, imidazolyl, pyrazolyl, pyridyl, pyradyl, pyridazinyl, pyrimidinyl, pyrazinyl, triazolyl, triazinyl, tetrazolyl, isoxazolyl, oxazolyl, oxadiazolyl, oxathiazolidyl, isothiazolyl, thiazolyl, thiadiazolyl, furyl, thienyl, etc; a fused bicyclic heterocyclic group such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzoimidazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzothiazolyl, imidazopyridyl, triazolopyridyl, imidazothiazolyl, pyrazinopyridazinyl, quinazolinyl, quinolyl, isoquinolyl, naphthyridinyl, naphthyridyl, dihydropyridyl, tetrahydroquinolyl, dihydrobenzisothiazolyl, benzoxathiazolyl, tetrahydrobenzothienyl, etc; tricyclic fused heterocyclic group such as carbazolyl, acrydinyl, xanthenyl, phenothiadinyl, phenoxathiinyl, phenoxadinyl, dibenzofuryl, etc; a non-aromatic heterocyclic group such as dioxanyl, thiiranyl, oxiranyl, oxathioranyl, azetidinyl, thianyl, pyrrolidyl, pyrrolinyl, imidazolidinyl, imidazolinyl, pyrazolidinyl, pyrazolinyl, piperidyl, piperadinyl, morpholinyl, morpholino, thiomorpholinyl, thiomorpholino, dihydropyridyl, tetrahydrofuryl, tetrahydropyranyl, tetrahydrothiazolyl, tetrahydroisothiazolyl, etc.

The term "cycloalkyl" includes a cyclic alkyl group having 3 to 8 carbon atoms, and preferably 5 or 6 carbon atoms, such as cyclopropyl, cyclobutyl, cyclopentyl, cyclohexyl, cycloheptyl, cyclooctyl, etc.

The term "cycloalkenyl" includes a group having one or more double bonds at any position in the above "cycloalkyl" ring, such as cyclopropenyl, cyclobutenyl, cyclopentenyl, cyclohexenyl and cyclohexadienyl, etc.

The term "alkoxy" means the above "alkyl" substituted by an oxygen atom and includes, for example, methoxy, ethoxy, n-propoxy, isopropoxy, n-butoxy, isobutoxy, sec-butoxy, tert-butoxy, n-pentyloxy, n-hexyloxy and n-heptyloxy, n-octyloxy, etc. Especially, a straight or branched chain alkoxy having 1 to 4 carbon atoms, such as methoxy, ethoxy, n-propoxy, isopropoxy, n-butoxy, isobutoxy, sec-butoxy and tert-butoxy are preferable.

The term "monocyclic heterocycle" includes a 5- or 6-membered monocyclic heterocyclic ring having one or more heteroatoms selected from O, S and N in the ring Specifically, it includes aromatic heterocyclic ring such as furan, thiophene, pyrrole, pyrazole, imidazole, oxazole, oxadiazole, isoxazole, thiazole, isothiazole, thiadiazole, pyran, thiopyran, pyridine, pyridazine, pyrimidine, pyradine, triazole, triadine, etc; a non-aromatic heterocyclic ring such as dihydropyridine, dihydropyridazine, dihydropyradine, dioxane, oxathiolane, thiane, pyrroline, pyrazolidine, piperidine, piperadine, morpholine, pyrrolidine, imidazolidine, isoxazolidine, isothiazolidine, tetrahydropyran, thiomorpholine, etc.

Substituent groups for "monocyclic heterocycle" includes the above alkyl, alkenyl, hydroxy, halogen, carboxy, alkoxycarbonyl, alkoxy, mercapto, alkylthio, alkylsulfonyl, aryl or heterocycle and one or more substituents may be substituted at any possible positions.

The term "fused bicyclic heterocycle" includes those wherein the above "monocyclic heterocycle" is fused with a monocyclic carbocycle (e.g., a ring derived from the above aromatic carbocycle or cycloalkyl, a ring derived from cycloalkenyl, etc.) or fused with monocyclic heterocycle as defined above. For example, it includes indole, isoindole, indazole, indolyzine, indoline, isoindole, quinoline, isoquinoline, cinnoline, phtharadine, quinazole, naphthyridine, quinoxaline, purine, pteridin, benzopyran, benzimidazole, benzisoxazole, benzoxazole, benzoxadiazole, benzisothiazole, benzothiazol, benzothiadiazol, benzofurin, isobenzofurin, benzothiene, benzotriazole, imidazopyridine, triazolopyridine, imidazothiazole, pyrazinopyridazine, quinazole, quinoline, isoquinoline, naphthyridine, dihydropyridine, tetrahydroquinoline, tetrahydrobenzothiene, pyrrolopyridine, dihydrobenzoxazole, etc.

An alkyl moiety in "alkylthio", "alkylcarbonyl", "alkylsulfonyl", "alkoxyalkyl" and "alkylsulfinyl" is the same as those in the above "alkyl".

An alkenyl moiety in "alkenyloxy", "alkenylthio", "alkenylcarbonyl", "alkenylsulfonyl" and "alkenylsulfinyl" is the same as those in the above "alkenyl".

An alkenyloxy moiety in "alkenyloxycarbonyl" is the same as those in the above "alkenyloxy".

An aryl moiety in "aryloxy", "arylthio", "arylcarbonyl", "arylsulfonyl" and "arylsulfinyl" is the same as those in the above "aryl".

An aryloxy moiety in "aryloxycarbonyl" is the same as those in the above "aryloxy".

A heterocyclyl moiety in "heterocyclyloxy", "heterocyclylthio", "heterocyclyloxycarbonyl", "heterocyclylcarbonyl", "heterocyclylsulfonyl" and "heterocyclylsulfinyl" is the same as those in the above "heterocyclyl".

A cycloalkyl moiety in "cycloalkyloxy", "cycloalkylthio", "cycloalkylcarbonyl", "cycloalkylsulfonyl" and "cycloalkylsulfinyl" is the same as those in the above "cycloalkyl".

A cycloalkyloxy moiety in "cycloalkyloxycarbonyl" is the same as those in the above "cycloalkyloxy".

A cycloalkenyl moiety in "cycloalkenyloxy", "cycloalkenylthio", "cycloalkenylcarbonyl", "cycloalkenylsulfonyl" and "cycloalkenylsulfinyl" is the same as those in the above "cycloalkenyl".

A cycloalkenyloxy moiety in "cycloalkenyloxycarbonyl" is the same as those in the above "cycloalkenyloxy".

An alkoxy moiety in "alkoxycarbonyl" and "alkoxyalkyl" is the same as those in the above "alkoxy".

Substituent groups for "substituted or unsubstituted alkyl", "substituted or unsubstituted alkenyl", "substituted or unsubstituted alkynyl", "substituted or unsubstituted alkoxy", "substituted or unsubstituted alkenyloxy", "substituted or unsubstituted cycloalkyl", "substituted or unsubstituted cycloalkyloxy", "substituted or unsubstituted cycloalkenyl", "substituted or unsubstituted cycloalkenyloxy", "substituted or unsubstituted aryl", "substituted or unsubstituted aryloxy", "substituted or unsubstituted heterocyclyl", "substituted or unsubstituted heterocyclyloxy", "substituted or unsubstituted alkylthio", "substituted or unsubstituted alkenylthio", "substituted or unsubstituted cycloalkylthio", "substituted or unsubstituted cycloalkenylthio", "substituted or unsubstituted arylthio", "substituted or unsubstituted heterocyclylthio", "substituted or unsubstituted alkoxycarbonyl", "substituted or unsubstituted alkenyloxycarbonyl", "substituted or unsubstituted cycloalkyloxycarbonyl", "substituted or unsubstituted cycloalkenyloxycarbonyl", "substituted or unsubstituted aryloxycarbonyl", "substituted or unsubstituted heterocyclyloxycarbonyl", "substituted or unsubstituted alkylcarbonyl", "substituted or unsubstituted alkenylcarbonyl", "substituted or unsubstituted cycloalkylcarbonyl", "substituted or unsubstituted cycloalkenylcarbonyl", "substituted or unsubstituted arylcarbonyl", "substituted or unsubstituted heterocyclylcarbonyl", "substituted or unsubstituted alkylsulfonyl", "substituted or unsubstituted alkenylsulfonyl", "substituted or unsubstituted cycloalkylsulfonyl", "substituted or unsubstituted cycloalkenylsulfonyl", "substituted or unsubstituted arylsulfonyl", "substituted or unsubstituted heterocyclylsulfonyl", "substituted or unsubstituted alkylsulfinyl", "substituted or unsubstituted alkenylsulfinyl", "substituted or unsubstituted cycloalkylsulfinyl", "substituted or unsubstituted cycloalkenylsulfinyl", "substituted or unsubstituted arylsulfinyl" and "substituted or unsubstituted heterocyclylsulfinyl" includes, for example, hydroxy, carboxy, halogen, halogenated alkyl (e.g., $CF_3$, $CH_2CF_3$, $CH_2CCl_3$), alkyl (e.g., methyl, ethyl, isopropyl, tert-butyl), alkenyl (e.g., vinyl), alkynyl(e.g., ethynyl), cycloalkyl(e.g., cyclopropyl), cycloalkenyl(e.g., cyclopropenyl), alkoxy (e.g., methoxy, ethoxy, propoxy, butoxy), halogenated alkoxy (e.g., $OCF_3$), alkenyloxy (e.g., vinyloxy, allyloxy), alkoxyalkyl (e.g., methoxymethyl, methoxyethyl), alkoxycarbonyl (e.g., methoxycarbonyl, ethoxycarbonyl, tert-butoxycarbonyl), nitro, nitroso, substituted or unsubstituted amino (e.g., alkylamino (e.g., methylamino, ethylamino, dimethylamino), acylamino (e.g., acetylamino, benzoylamino), aralkylamino (e.g., benzylamino, tritylamino), hydroxyamino, alkoxycarbonylamino, alkylsulfonylamino, carbamoylamino, heterocyclylcarbonylamino, arylsulfonylamino), azide, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethanesulfonyl), substituted or unsubstituted carbamoyl (e.g., alkylcarbamoyl (e.g., methylcarbamoyl, ethylcarbamoyl, dimethylcarbamoyl), alkylsulfonylcarbamoyl), sulfamoyl, acyl(e.g., formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azide, ureido, amidino, guanidino, phthalimide, oxo, heteroaryl, heterocyclyl, alkylene, alkylenedioxy (—O—$CH_2$—O—, —O—$CH_2$—$CH_2$—O—, —O—$CH_2$—$CH_2$—$CH_2$—O—, etc.), alkenylene, cycloalkylene, cycloalkenylene, arylene, heterocyclyldiyl, heteroarylene, heterocyclylcarbonyl, aryloxy(e.g., phenoxy), haloaryloxy (e.g., halophenoxy), aryloxycarbonyl, arylsulfonyl, arylthio, etc.

Substituent groups for "substituted or unsubstituted amino", "substituted or unsubstituted carbamoyl" and "substituted or unsubstituted sulfamoyl" includes alkyl, alkenyl, aryl, heteroaryl, alkylcarbonyl, arylcarbonyl, heteroarylcarbonyl, heterocyclylcarbonyl, alkoxycarbonyl, aryloxycarbonyl, heteroaryloxycarbonyl, heterocyclyloxycarbonyl, sulfamoyl, alkylsulfonyl, carbamoyl, cycloalkylsulfonyl, arylsulfonyl, heteroarylsulfonyl, heterocyclylsulfonyl, acyl, hydroxy, sulfinyl, etc.

A compound of the present invention includes any formable and pharmaceutically acceptable salts thereof. Examples of "the pharmaceutically acceptable salt" are salts with mineral acids such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium, magnesium, etc.

The compound of the present invention includes solvates of the compound of the formula (I). Hydrate is preferable and arbitrary numbers of water molecules may coordinate to the compound of the present invention.

In addition, the compound of the present invention includes a prodrug thereof. The prodrug is a derivative of the compound of the present invention having a group which can be chemically or metabolically degraded, and is a compound which serves as a pharmaceutically active compound of the present invention in vivo by solvolysis, or under physiological condition. A method of selecting a suitable prodrug derivative and a process for producing a suitable prodrug derivative are described, for example, in Design of Prodrugs, Elsevier, Amsterdam 1985.

For example, when the compound (I) of the present invention has carboxy group, a prodrug such as an ester derivative produced by reacting carboxy group of the compound (I) and a suitable alcohol, and an amide derivative produced by reacting carboxy group of the compound (I) and a suitable amine is exemplified.

For example, when the compound (I) of the present invention has hydroxy group, a prodrug such as an acyloxy derivative produced by reacting hydroxy group of the compound (I) and suitable acyl halide or suitable acid anhydride is exemplified.

For example, when the compound (I) of the present invention has amino group, a prodrug such as an amide derivative produced by reacting amino group of the compound (I) and suitable acid halide or suitable mixed acid anhydride is exemplified.

When the compound (I) of the present invention has an asymmetric carbon atom, racemate, enantiomeric pairs and all steric isomers (geometrical isomer, epimer, enantiomer and the like) are included. In addition, when the compound of the formula (I) has one or more double bonds and an E-form and Z-form are present, these forms are included in the scope of the compound of the present invention.

In addition, one or more hydrogen, carbon or other atoms of a compound of the formula (I) can be replaced by an isotope of the hydrogen, carbon or other atoms. The compounds of formula (I) include all radiolabeled forms of compounds of the formula (I). Such "radiolabeled" "radiolabeled form" and the like of a compound of formula (I), each of which is encompassed by the invention, is useful as a research and/or diagnostic tool in metabolism pharmacokinetic studies and in binding assays. Examples of isotopes that can be incorporated into a compound of the formula (I) of the present invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of formula (I) can be prepared by introducing tritium into the particular compound of Formula (I), for example, by catalytic dehalogenation with tritium. This method may include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

Particularly preferable compounds of the formula (I) are as follows.

In the formula (I),
(A1) A is substituted or unsubstituted phenyl (hereinafter referred to as "A is A1").

(A1) A is substituted or unsubstituted triazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzimidazolyl, substituted or unsubstituted dihydrobenzisothiazolyl, or substituted or unsubstituted benzoxathiazolyl (hereinafter referred to as "A is A2").

(B1) B is benzene (hereinafter referred to as "B is B1").

(B2) B is pyrazole, imidazole, pyridine or pyradine (hereinafter referred to as "B is B2").

(B3) B is indazole or dihydrobenzoxazole (hereinafter referred to as "B is B3").

(M1) m is 0 (hereinafter referred to as "m is M1").

(M2) m is 1 (hereinafter referred to as "m is M2").

(N1) n is 0 (hereinafter referred to as "n is N1").

(N2) n is 1 (hereinafter referred to as "n is N2").

(R5a) $R^5$ is substituted or unsubstituted phenyl (hereinafter referred to as "$R^5$ is R5a").

(R5b) $R^5$ is substituted or unsubstituted pyridyl, or substituted or unsubstituted morpholino (hereinafter referred to as "$R^5$ is R5b").

(R6a) $R^6$ is halogen, oxo, substituted or unsubstituted alkyl (hereinafter referred to as "$R^6$ is R6a").

(R6b) $R^6$ is substituted or unsubstituted alkoxy, or substituted or unsubstituted aryloxy (hereinafter referred to as "$R^6$ is R6b").

(X1Y1) X is C(=O)N($R^1$) and Y is C(=O)N($R^2$) (hereinafter referred to as "X1Y1").

(X1Y2) X is C(=O)N($R^1$) and Y is imidazole-1,3-diyl (hereinafter referred to as "X1Y2").

(X2Y1) X is N($R^1$) and Y is C(=O)N($R^2$) (hereinafter referred to as "X2Y1").

(X3Y1) X is O and Y is C(=O)N($R^2$) (hereinafter referred to as "X3Y1").

(X4Y3) X is C($R^3$)($R^4$) and Y is N($R^2$) (hereinafter referred to as "X4Y3").

(X5Y1) X is a single bond and Y is C(=O)N($R^2$) (hereinafter referred to as "X5Y1").

The compounds wherein the combinations of A, B, m, n, $R^5$, $R^6$, X and Y, i.e., (A, B, m, n, $R^5$, $R^6$, XY), are as follows:

(A1, B1, M1, N1, R5a, R6a, X1Y1), (A1, B1, M1, N1, R5a, R6a, X1Y2), (A1, B1, M1, N1, R5a, R6a, X2Y1), (A1, B1, M1, N1, R5a, R6a, X3Y1), (A1, B1, M1, N1, R5a, R6a, X4Y3), (A1, B1, M1, N1, R5a, R6a, X5Y1), (A1, B1, M1, N1, R5a, R6b, X1Y1), (A1, B1, M1, N1, R5a, R6b, X1Y2), (A1, B1, M1, N1, R5a, R6b, X2Y1), (A1, B1, M1, N1, R5a, R6b, X3Y1), (A1, B1, M1, N1, R5a, R6b, X4Y3), (A1, B1, M1, N1, R5a, R6b, X5Y1), (A1, B1, M1, N1, R5b, R6a, X1Y1), (A1, B1, M1, N1, R5b, R6a, X1Y2), (A1, B1, M1, N1, R5b, R6a, X2Y1), (A1, B1, M1, N1, R5b, R6a, X3Y1), (A1, B1, M1, N1, R5b, R6a, X4Y3), (A1, B1, M1, N1, R5b, R6a, X5Y1), (A1, B1, M1, N1, R5b, R6b, X1Y1), (A1, B1, M1, N1, R5b, R6b, X1Y2), (A1, B1, M1, N1, R5b, R6b, X2Y1), (A1, B1, M1, N1, R5b, R6b, X3Y1), (A1, B1, M1, N1, R5b, R6b, X4Y3), (A1, B1, M1, N1, R5b, R6b, X5Y1), (A1, B1, M1, N2, R5a, R6a, X1Y1), (A1, B1, M1, N2, R5a, R6a, X1Y2), (A1, B1, M1, N2, R5a, R6a, X2Y1), (A1, B1, M1, N2, R5a, R6a, X3Y1), (A1, B1, M1, N2, R5a, R6a, X4Y3), (A1, B1, M1, N2, R5a, R6a, X5Y1), (A1, B1, M1, N2, R5a, R6b, X1Y1), (A1, B1, M1, N2, R5a, R6b, X1Y2), (A1, B1, M1, N2, R5a, R6b, X2Y1), (A1, B1, M1, N2, R5a, R6b, X3Y1), (A1, B1, M1, N2, R5a, R6b, X4Y3), (A1, B1, M1, N2, R5a, R6b, X5Y1), (A1, B1, M1, N2, R5b, R6a, X1Y1), (A1, B1, M1, N2, R5b, R6a, X1Y2), (A1, B1, M1, N2, R5b, R6a, X2Y1), (A1, B1, M1, N2, R5b, R6a, X3Y1), (A1, B1, M1, N2, R5b, R6a, X4Y3), (A1, B1, M1, N2, R5b, R6a, X5Y1), (A1, B1, M1, N2, R5b, R6b, X1Y1), (A1, B1, M1, N2, R5b, R6b, X1Y2), (A1, B1, M1, N2, R5b, R6b, X2Y1), (A1, B1, M1, N2, R5b, R6b, X3Y1), (A1, B1, M1, N2, R5b, R6b, X4Y3), (A1, B1, M1, N2, R5b, R6b, X5Y1), (A1, B1, M2, N1, R5a, R6a, X1Y1), (A1, B1, M2, N1, R5a, R6a, X1Y2), (A1, B1, M2, N1, R5a, R6a, X2Y1), (A1, B1, M2, N1, R5a, R6a, X3Y1), (A1, B1, M2, N1, R5a, R6a, X4Y3), (A1, B1, M2, N1, R5a, R6a, X5Y1), (A1, B1, M2, N1, R5a, R6b, X1Y1), (A1, B1, M2, N1, R5a, R6b, X1Y2), (A1, B1, M2, N1, R5a, R6b, X2Y1), (A1, B1, M2, N1, R5a, R6b, X3Y1), (A1, B1, M2, N1, R5a, R6b, X4Y3), (A1, B1, M2, N1, R5a, R6b, X5Y1), (A1, B1, M2, N1, R5b, R6a, X1Y1), (A1, B1, M2, N1, R5b, R6a, X1Y2), (A1, B1, M2, N1, R5b, R6a, X2Y1), (A1, B1, M2, N1, R5b, R6a, X3Y1), (A1, B1, M2, N1, R5b, R6a, X4Y3), (A1, B1, M2, N1, R5b, R6a, X5Y1), (A1, B1, M2, N1, R5b, R6b, X1Y1), (A1, B1, M2, N1, R5b, R6b, X1Y2), (A1, B1, M2, N1, R5b, R6b, X2Y1), (A1, B1, M2, N1, R5b, R6b, X3Y1), (A1, B1, M2, N1, R5b, R6b, X4Y3), (A1, B1, M2, N1, R5b, R6b, X5Y1), (A1, B1, M2, N2, R5a, R6a, X1Y1), (A1, B1, M2, N2, R5a, R6a, X1Y2), (A1, B1, M2, N2, R5a, R6a, X2Y1), (A1, B1, M2, N2, R5a, R6a, X3Y1), (A1, B1, M2, N2, R5a, R6a, X4Y3), (A1, B1, M2, N2, R5a, R6a, X5Y1), (A1, B1, M2, N2, R5a, R6b, X1Y1), (A1, B1, M2, N2, R5a, R6b, X1Y2), (A1, B1, M2, N2, R5a, R6b, X2Y1), (A1, B1, M2, N2, R5a, R6b, X3Y1), (A1, B1, M2, N2, R5a, R6b, X4Y3), (A1, B1, M2, N2, R5a, R6b, X5Y1), (A1, B1, M2, N2, R5b, R6a, X1Y1), (A1, B1, M2, N2, R5b, R6a, X1Y2), (A1, B1, M2, N2, R5b, R6a, X2Y1), (A1, B1, M2, N2, R5b, R6a, X3Y1), (A1, B1, M2, N2, R5b, R6a, X4Y3), (A1, B1, M2, N2, R5b, R6a, X5Y1), (A1, B1, M2, N2, R5b, R6b, X1Y1), (A1, B1, M2, N2, R5b, R6b, X1Y2), (A1, B1, M2, N2, R5b, R6b, X2Y1), (A1, B1, M2, N2, R5b, R6b, X3Y1), (A1, B1, M2, N2, R5b, R6b, X4Y3), (A1, B1, M2, N2, R5b, R6b, X5Y1), (A1, B2, M1, N1, R5a, R6a, X1Y1), (A1, B2, M1, N1, R5a, R6a, X1Y2), (A1, B2, M1, N1, R5a, R6a, X2Y1), (A1, B2, M1, N1, R5a, R6a, X3Y1), (A1, B2, M1, N1, R5a, R6a, X4Y3), (A1, B2, M1, N1, R5a, R6a, X5Y1), (A1, B2, M1, N1, R5a, R6b, X1Y1), (A1, B2, M1, N1, R5a, R6b, X1Y2), (A1, B2, M1, N1, R5a, R6b, X2Y1), (A1, B2, M1, N1, R5a, R6b, X3Y1), (A1, B2, M1, N1, R5a, R6b, X4Y3), (A1, B2, M1, N1, R5a, R6b, X5Y1), (A1, B2, M1, N1, R5b, R6a, X1Y1), (A1, B2, M1, N1, R5b, R6a, X1Y2), (A1, B2, M1, N1, R5b, R6a, X2Y1), (A1, B2, M1, N1, R5b, R6a, X3Y1), (A1, B2, M1, N1, R5b, R6a, X4Y3), (A1, B2, M1, N1, R5b, R6a, X5Y1), (A1, B2, M1, N1, R5b, R6b, X1Y1), (A1, B2, M1, N1, R5b, R6b, X1Y2), (A1, B2, M1, N1, R5b, R6b, X2Y1), (A1, B2, M1, N1, R5b, R6b, X3Y1), (A1, B2, M1, N1, R5b, R6b, X4Y3), (A1, B2, M1, N1, R5b, R6b, X5Y1), (A1, B2, M1, N2, R5a, R6a, X1Y1), (A1, B2, M1, N2, R5a, R6a, X1Y2), (A1, B2, M1, N2, R5a, R6a, X2Y1), (A1, B2, M1, N2, R5a, R6a, X3Y1), (A1, B2, M1, N2, R5a, R6a, X4Y3), (A1, B2, M1, N2, R5a, R6a, X5Y1), (A1, B2, M1, N2, R5a, R6b, X1Y1), (A1, B2, M1, N2, R5a, R6b, X1Y2), (A1, B2, M1, N2, R5a, R6b, X2Y1), (A1, B2, M1, N2, R5a, R6b, X3Y1), (A1, B2, M1, N2, R5a, R6b, X4Y3), (A1, B2, M1, N2, R5a, R6b, X5Y1), (A1, B2, M1, N2, R5b, R6a, X1Y1), (A1, B2, M1, N2, R5b, R6a, X1Y2), (A1, B2, M1, N2, R5b, R6a, X2Y1), (A1, B2, M1, N2, R5b, R6a, X3Y1), (A1, B2, M1, N2, R5b, R6a, X4Y3), (A1, B2, M1, N2, R5b, R6a, X5Y1), (A1, B2, M1, N2, R5b, R6b, X1Y1), (A1, B2, M1, N2, R5b, R6b, X1Y2), (A1, B2, M1, N2, R5b, R6b, X2Y1), (A1, B2, M1, N2, R5b, R6b, X3Y1), (A1, B2, M1, N2, R5b, R6b, X4Y3), (A1, B2, M1, N2, R5b, R6b, X5Y1), (A1, B2, M2, N1, R5a, R6a, X1Y1), (A1, B2, M2, N1, R5a, R6a, X1Y2), (A1, B2, M2, N1, R5a, R6a, X2Y1), (A1, B2, M2, N1, R5a, R6a, X3Y1), (A1, B2, M2, N1, R5a, R6a, X4Y3), (A1, B2, M2, N1, R5a, R6a, X5Y1), (A1, B2, M2, N1, R5a, R6b, X1Y1), (A1, B2, M2, N1, R5a, R6b, X1Y2), (A1, B2, M2, N1, R5a, R6b, X2Y1), (A1, B2, M2, N1, R5a, R6b, X3Y1), (A1, B2, M2, N1, R5a, R6b, X4Y3), (A1, B2, M2, N1, R5a, R6b, X5Y1), (A1, B2, M2, N1, R5b, R6a, X1Y1), (A1, B2, M2, N1, R5b, R6a, X1Y2), (A1, B2, M2, N1, R5b, R6a, X2Y1), (A1, B2, M2, N1, R5b, R6a, X3Y1), (A1, B2, M2, N1, R5b, R6a, X4Y3), (A1, B2, M2, N1, R5b, R6a, X5Y1), (A1, B2, M2, N1, R5b, R6b, X1Y1), (A1, B2, M2, N1, R5b, R6b, X1Y2), (A1, B2, M2, N1, R5b, R6b, X2Y1), (A1, B2, M2, N1, R5b, R6b, X3Y1), (A1, B2, M2, N1, R5b, R6b, X4Y3), (A1, B2, M2, N1, R5b, R6b, X5Y1), (A1, B2, M2, N2, R5a, R6a, X1Y1), (A1, B2, M2, N2, R5a, R6a, X1Y2), (A1, B2, M2, N2, R5a, R6a, X2Y1), (A1, B2, M2, N2, R5a, R6a, X3Y1), (A1, B2, M2, N2, R5a, R6a, X4Y3), (A1, B2, M2, N2, R5a, R6a, X5Y1), (A1, B2, M2, N2, R5a, R6b, X1Y1), (A1, B2, M2, N2, R5a, R6b, X1Y2), (A1, B2, M2, N2, R5a, R6b, X2Y1), (A1, B2, M2, N2, R5a, R6b, X3Y1), (A1, B2, M2, N2, R5a, R6b, X4Y3), (A1, B2, M2, N2, R5a, R6b, X5Y1), (A1, B2, M2, N2, R5b, R6a, X1Y1), (A1, B2, M2, N2, R5b, R6a, X1Y2), (A1, B2, M2, N2, R5b, R6a, X2Y1), (A1, B2, M2, N2, R5b, R6a, X3Y1), (A1, B2, M2, N2, R5b, R6a, X4Y3), (A1, B2, M2, N2, R5b, R6a, X5Y1), (A1, B2, M2, N2, R5b, R6b, X1Y1), (A1, B2, M2, N2, R5b, R6b, X1Y2), (A1, B2, M2, N2, R5b, R6b, X2Y1), (A1, B2, M2, N2, R5b, R6b, X3Y1), (A1, B2, M2, N2, R5b, R6b, X4Y3), (A1, B2, M2, N2, R5b, R6b, X5Y1), (A1, B3, M1, N1, R5a, R6a, X1Y1), (A1, B3, M1, N1, R5a, R6a, X1Y2), (A1, B3, M1, N1, R5a, R6a, X2Y1), (A1, B3, M1, N1, R5a, R6a, X3Y1), (A1, B3, M1, N1, R5a, R6a, X4Y3), (A1, B3, M1, N1, R5a, R6a, X5Y1), (A1, B3, M1, N1, R5a, R6b, X1Y1), (A1, B3, M1, N1, R5a, R6b, X1Y2), (A1, B3, M1, N1, R5a, R6b, X2Y1), (A1, B3, M1, N1, R5a, R6b, X3Y1), (A1, B3, M1, N1, R5a, R6b, X4Y3), (A1, B3, M1, N1, R5a, R6b, X5Y1), (A1, B3, M1, N1, R5b, R6a, X1Y1), (A1, B3, M1, N1, R5b, R6a, X1Y2), (A1, B3, M1, N1, R5b, R6a, X2Y1), (A1, B3, M1, N1, R5b, R6a, X3Y1), (A1, B3, M1, N1, R5b, R6a, X4Y3), (A1, B3, M1, N1, R5b, R6a, X5Y1), (A1, B3, M1, N1, R5b, R6b, X1Y1), (A1, B3, M1, N1, R5b, R6b, X1Y2), (A1, B3, M1, N1, R5b, R6b, X2Y1), (A1, B3, M1, N1, R5b, R6b, X3Y1), (A1, B3, M1, N1, R5b, R6b, X4Y3), (A1, B3, M1, N1, R5b, R6b, X5Y1), (A1, B3, M1, N2, R5a, R6a, X1Y1), (A1, B3, M1, N2, R5a, R6a, X1Y2), (A1, B3, M1, N2, R5a, R6a, X2Y1), (A1, B3, M1, N2, R5a, R6a, X3Y1), (A1, B3, M1, N2, R5a, R6a, X4Y3), (A1, B3, M1, N2, R5a, R6a, X5Y1), (A1, B3, M1, N2, R5a, R6b, X1Y1), (A1, B3, M1, N2, R5a, R6b, X1Y2), (A1, B3, M1, N2, R5a, R6b, X2Y1), (A1, B3, M1, N2, R5a, R6b, X3Y1), (A1, B3, M1, N2, R5a, R6b, X4Y3), (A1, B3, M1, N2, R5a, R6b, X5Y1), (A1, B3, M1, N2, R5b, R6a, X1Y1), (A1, B3, M1, N2, R5b, R6a, X1Y2), (A1, B3, M1, N2, R5b, R6a, X2Y1), (A1, B3, M1, N2, R5b, R6a, X3Y1), (A1, B3, M1, N2, R5b, R6a, X4Y3), (A1, B3, M1, N2, R5b, R6a, X5Y1), (A1, B3, M1, N2, R5b, R6b, X1Y1), (A1, B3, M1, N2, R5b, R6b, X1Y2), (A1, B3, M1, N2, R5b, R6b, X2Y1), (A1, B3, M1, N2, R5b, R6b, X3Y1), (A1, B3, M1, N2, R5b, R6b, X4Y3), (A1, B3, M1, N2, R5b, R6b, X5Y1), (A1, B3, M2, N1, R5a, R6a, X1Y1), (A1, B3, M2, N1, R5a, R6a, X1Y2), (A1, B3, M2, N1, R5a, R6a, X2Y1), (A1, B3, M2, N1, R5a, R6a, X3Y1), (A1, B3, M2, N1, R5a, R6a, X4Y3), (A1, B3, M2, N1, R5a, R6a, X5Y1), (A1, B3, M2, N1, R5a, R6b, X1Y1), (A1, B3, M2, N1, R5a, R6b, X1Y2), (A1, B3, M2, N1, R5a, R6b, X2Y1), (A1, B3, M2, N1, R5a, R6b, X3Y1), (A1, B3, M2, N1, R5a, R6b, X4Y3), (A1, B3, M2, N1, R5a, R6b, X5Y1), (A1, B3, M2, N1, R5b, R6a, X1Y1), (A1, B3, M2, N1, R5b, R6a, X1Y2), (A1, B3, M2, N1, R5b, R6a, X2Y1), (A1, B3, M2, N1, R5b, R6a, X3Y1), (A1, B3, M2, N1, R5b, R6a, X4Y3), (A1, B3, M2, N1, R5b, R6a, X5Y1), (A1, B3, M2, N1, R5b, R6b, X1Y1), (A1, B3, M2, N1, R5b, R6b, X1Y2), (A1, B3, M2, N1, R5b, R6b, X2Y1), (A1, B3, M2, N1, R5b, R6b, X3Y1), (A1, B3, M2, N1, R5b, R6b, X4Y3), (A1, B3, M2, N1, R5b, R6b, X5Y1), (A1, B3, M2, N2, R5a, R6a, X1Y1), (A1, B3, M2, N2, R5a, R6a, X1Y2), (A1, B3, M2, N2, R5a, R6a, X2Y1), (A1, B3, M2, N2, R5a, R6a, X3Y1), (A1, B3, M2, N2, R5a, R6a, X4Y3), (A1, B3, M2, N2, R5a, R6a, X5Y1), (A1, B3, M2, N2, R5a, R6b, X1Y1), (A1, B3, M2, N2, R5a, R6b, X1Y2), (A1, B3, M2, N2, R5a, R6b, X2Y1), (A1, B3, M2, N2, R5a, R6b, X3Y1), (A1, B3, M2, N2, R5a, R6b, X4Y3), (A1, B3, M2, N2, R5a, R6b, X5Y1), (A1, B3, M2, N2, R5b, R6a, X1Y1), (A1, B3, M2, N2, R5b, R6a, X1Y2), (A1, B3, M2, N2, R5b, R6a, X2Y1), (A1, B3, M2, N2, R5b, R6a, X3Y1), (A1, B3, M2, N2, R5b, R6a, X4Y3), (A1, B3, M2, N2, R5b, R6a, X5Y1), (A1, B3, M2, N2, R5b, R6b, X1Y1), (A1, B3, M2, N2, R5b, R6b, X1Y2), (A1, B3, M2, N2, R5b, R6b, X2Y1), (A1, B3, M2, N2, R5b, R6b, X3Y1), (A1, B3, M2, N2, R5b, R6b, X4Y3), (A1, B3, M2, N2, R5b, R6b, X5Y1), (A2, B1, M1, N1, R5a, R6a, X1Y1), (A2, B1, M1, N1, R5a, R6a, X1Y2), (A2, B1, M1, N1, R5a, R6a, X2Y1), (A2, B1, M1, N1, R5a, R6a, X3Y1), (A2, B1, M1, N1, R5a, R6a, X4Y3), (A2, B1, M1, N1, R5a, R6a, X5Y1), (A2, B1, M1, N1, R5a, R6b, X1Y1), (A2, B1, M1, N1, R5a, R6b, X1Y2), (A2, B1, M1, N1, R5a, R6b, X2Y1), (A2, B1, M1, N1, R5a, R6b, X3Y1), (A2, B1, M1, N1, R5a, R6b, X4Y3), (A2, B1, M1, N1, R5a, R6b, X5Y1), (A2, B1, M1, N1, R5b, R6a, X1Y1), (A2, B1, M1, N1, R5b, R6a, X1Y2), (A2, B1, M1, N1, R5b, R6a, X2Y1), (A2, B1, M1, N1, R5b, R6a, X3Y1), (A2, B1, M1, N1, R5b, R6a, X4Y3), (A2, B1, M1, N1, R5b, R6a, X5Y1), (A2, B1, M1, N1, R5b, R6b, X1Y1), (A2, B1, M1, N1, R5b, R6b, X1Y2), (A2, B1, M1, N1, R5b, R6b, X2Y1), (A2, B1, M1, N1, R5b, R6b, X3Y1), (A2, B1, M1, N1, R5b, R6b, X4Y3), (A2, B1, M1, N1, R5b, R6b, X5Y1), (A2, B1, M1, N2, R5a, R6a, X1Y1), (A2, B1, M1, N2, R5a, R6a, X1Y2), (A2, B1, M1, N2, R5a, R6a, X2Y1), (A2, B1, M1, N2, R5a, R6a, X3Y1), (A2, B1, M1, N2, R5a, R6a, X4Y3), (A2, B1, M1, N2, R5a, R6a, X5Y1), (A2, B1, M1, N2, R5a, R6b, X1Y1), (A2, B1, M1, N2, R5a, R6b, X1Y2), (A2, B1, M1, N2, R5a, R6b, X2Y1), (A2, B1, M1, N2, R5a, R6b, X3Y1), (A2, B1, M1, N2, R5a, R6b, X4Y3), (A2, B1, M1, N2, R5a, R6b, X5Y1), (A2, B1, M1, N2, R5b, R6a, X1Y1), (A2, B1, M1, N2, R5b, R6a, X1Y2), (A2, B1, M1, N2, R5b, R6a, X2Y1), (A2, B1, M1, N2, R5b, R6a, X3Y1), (A2, B1, M1, N2, R5b, R6a, X4Y3), (A2, B1, M1, N2, R5b, R6a, X5Y1), (A2, B1, M1, N2, R5b, R6b, X1Y1), (A2, B1, M1, N2, R5b, R6b, X1Y2), (A2, B1, M1, N2, R5b, R6b, X2Y1), (A2, B1, M1, N2, R5b, R6b, X3Y1), (A2, B1, M1, N2, R5b, R6b, X4Y3), (A2, B1, M1, N2, R5b, R6b, X5Y1), (A2, B1, M2, N1, R5a, R6a, X1Y1), (A2, B1, M2, N1, R5a, R6a, X1Y2), (A2, B1, M2, N1, R5a, R6a, X2Y1), (A2, B1, M2, N1, R5a, R6a, X3Y1), (A2, B1, M2, N1, R5a, R6a, X4Y3), (A2, B1, M2, N1, R5a, R6a, X5Y1), (A2, B1, M2, N1, R5a, R6b, X1Y1), (A2, B1, M2, N1, R5a, R6b, X1Y2), (A2, B1, M2, N1, R5a, R6b, X2Y1), (A2, B1, M2, N1, R5a, R6b, X3Y1), (A2, B1, M2, N1, R5a, R6b, X4Y3), (A2, B1, M2, N1, R5a, R6b, X5Y1), (A2, B1, M2, N1, R5b, R6a, X1Y1), (A2, B1, M2, N1, R5b, R6a, X1Y2), (A2, B1, M2, N1, R5b, R6a, X2Y1), (A2, B1, M2, N1, R5b, R6a, X3Y1), (A2, B1, M2, N1, R5b, R6a, X4Y3), (A2, B1, M2, N1, R5b, R6a, X5Y1), (A2, B1, M2, N1, R5b, R6b, X1Y1), (A2, B1, M2, N1, R5b, R6b, X1Y2), (A2, B1, M2, N1, R5b, R6b, X2Y1), (A2, B1, M2, N1, R5b, R6b, X3Y1), (A2, B1, M2, N1, R5b, R6b, X4Y3), (A2, B1, M2, N1, R5b, R6b, X5Y1), (A2, B1, M2, N2, R5a, R6a, X1Y1), (A2, B1, M2, N2, R5a, R6a, X1Y2), (A2, B1, M2, N2, R5a, R6a, X2Y1), (A2, B1, M2, N2, R5a, R6a, X3Y1), (A2, B1, M2, N2, R5a, R6a, X4Y3), (A2, B1, M2, N2, R5a, R6a, X5Y1), (A2, B1, M2, N2, R5a, R6b, X1Y1), (A2, B1, M2, N2, R5a, R6b, X1Y2), (A2, B1, M2, N2, R5a, R6b, X2Y1), (A2, B1, M2, N2, R5a, R6b, X3Y1), (A2, B1, M2, N2, R5a, R6b, X4Y3), (A2, B1, M2, N2, R5a, R6b, X5Y1), (A2, B1, M2, N2, R5b, R6a, X1Y1), (A2, B1, M2, N2, R5b, R6a, X1Y2), (A2, B1, M2, N2, R5b, R6a, X2Y1), (A2, B1, M2, N2, R5b, R6a, X3Y1), (A2, B1, M2, N2, R5b, R6a, X4Y3), (A2, B1, M2, N2, R5b, R6a, X5Y1), (A2, B1, M2, N2, R5b, R6b, X1Y1), (A2, B1, M2, N2, R5b, R6b, X1Y2), (A2, B1, M2, N2, R5b, R6b, X2Y1), (A2, B1, M2, N2, R5b, R6b, X3Y1), (A2, B1, M2, N2, R5b, R6b, X4Y3), (A2, B1, M2, N2, R5b, R6b, X5Y1), (A2, B2, M1, N1, R5a, R6a, X1Y1), (A2, B2, M1, N1, R5a, R6a, X1Y2), (A2, B2, M1, N1, R5a, R6a, X2Y1), (A2, B2, M1, N1, R5a, R6a, X3Y1), (A2, B2, M1, N1, R5a, R6a, X4Y3), (A2, B2, M1, N1, R5a, R6a, X5Y1), (A2, B2, M1, N1, R5a, R6b, X1Y1), (A2, B2, M1, N1, R5a, R6b, X1Y2), (A2, B2, M1, N1, R5a, R6b, X2Y1), (A2, B2, M1, N1, R5a, R6b, X3Y1), (A2, B2, M1, N1, R5a, R6b, X4Y3), (A2, B2, M1, N1, R5a, R6b, X5Y1), (A2, B2, M1, N1, R5b, R6a, X1Y1), (A2, B2, M1, N1, R5b, R6a, X1Y2), (A2, B2, M1, N1, R5b, R6a, X2Y1), (A2, B2, M1, N1, R5b, R6a, X3Y1), (A2, B2, M1, N1, R5b, R6a, X4Y3), (A2, B2, M1, N1, R5b, R6a, X5Y1), (A2, B2, M1, N1, R5b, R6b, X1Y1), (A2, B2, M1, N1, R5b, R6b, X1Y2), (A2, B2, M1, N1, R5b, R6b, X2Y1), (A2, B2, M1, N1, R5b, R6b, X3Y1), (A2, B2, M1, N1, R5b, R6b, X4Y3), (A2, B2, M1, N1, R5b, R6b, X5Y1), (A2, B2, M1, N2, R5a, R6a, X1Y1), (A2, B2, M1, N2, R5a, R6a, X1Y2), (A2, B2, M1, N2, R5a, R6a, X2Y1), (A2, B2, M1, N2, R5a, R6a, X3Y1), (A2, B2, M1, N2, R5a, R6a, X4Y3), (A2, B2, M1, N2, R5a, R6a, X5Y1), (A2, B2, M1, N2, R5a, R6b, X1Y1), (A2, B2, M1, N2, R5a, R6b, X1Y2), (A2, B2, M1, N2, R5a, R6b, X2Y1), (A2, B2, M1, N2, R5a, R6b, X3Y1), (A2, B2, M1, N2, R5a, R6b, X4Y3), (A2, B2, M1, N2, R5a, R6b, X5Y1), (A2, B2, M1, N2, R5b, R6a, X1Y1), (A2, B2, M1, N2, R5b, R6a, X1Y2), (A2, B2, M1, N2, R5b, R6a, X2Y1), (A2, B2, M1, N2, R5b, R6a, X3Y1), (A2, B2, M1, N2, R5b, R6a, X4Y3), (A2, B2, M1, N2, R5b, R6a, X5Y1), (A2, B2, M1, N2, R5b, R6b, X1Y1), (A2, B2, M1, N2, R5b, R6b, X1Y2), (A2, B2, M1, N2, R5b, R6b, X2Y1), (A2, B2, M1, N2, R5b, R6b, X3Y1), (A2, B2, M1, N2, R5b, R6b, X4Y3), (A2, B2, M1, N2, R5b, R6b, X5Y1), (A2, B2, M2, N1, R5a, R6a, X1Y1), (A2, B2, M2, N1, R5a, R6a, X1Y2), (A2, B2, M2, N1, R5a, R6a, X2Y1), (A2, B2, M2, N1, R5a, R6a, X3Y1), (A2, B2, M2, N1, R5a, R6a, X4Y3), (A2, B2, M2, N1, R5a, R6a, X5Y1), (A2, B2, M2, N1, R5a, R6b, X1Y1), (A2, B2, M2, N1, R5a, R6b, X1Y2), (A2, B2, M2, N1, R5a, R6b, X2Y1), (A2, B2, M2, N1, R5a, R6b, X3Y1), (A2, B2, M2, N1, R5a, R6b, X4Y3), (A2, B2, M2, N1, R5a, R6b, X5Y1), (A2, B2, M2, N1, R5b, R6a, X1Y1), (A2, B2, M2, N1, R5b, R6a, X1Y2), (A2, B2, M2, N1, R5b, R6a, X2Y1), (A2, B2, M2, N1, R5b, R6a, X3Y1), (A2, B2, M2, N1, R5b, R6a, X4Y3), (A2, B2, M2, N1, R5b, R6a, X5Y1), (A2, B2, M2, N1, R5b, R6b, X1Y1), (A2, B2, M2, N1, R5b, R6b, X1Y2), (A2, B2, M2, N1, R5b, R6b, X2Y1), (A2, B2, M2, N1, R5b, R6b, X3Y1), (A2, B2, M2, N1, R5b, R6b, X4Y3), (A2, B2, M2, N1, R5b, R6b, X5Y1), (A2, B2, M2, N2, R5a, R6a, X1Y1), (A2, B2, M2, N2, R5a, R6a, X1Y2), (A2, B2, M2, N2, R5a, R6a, X2Y1), (A2, B2, M2, N2, R5a, R6a, X3Y1), (A2, B2, M2, N2, R5a, R6a, X4Y3), (A2, B2, M2, N2, R5a, R6a, X5Y1), (A2, B2, M2, N2, R5a, R6b, X1Y1), (A2, B2, M2, N2, R5a, R6b, X1Y2), (A2, B2, M2, N2, R5a, R6b, X2Y1), (A2, B2, M2, N2, R5a, R6b, X3Y1), (A2, B2, M2, N2, R5a, R6b, X4Y3), (A2, B2, M2, N2, R5a, R6b, X5Y1), (A2, B2, M2, N2, R5b, R6a, X1Y1), (A2, B2, M2, N2, R5b, R6a, X1Y2), (A2, B2, M2, N2, R5b, R6a, X2Y1), (A2, B2, M2, N2, R5b, R6a, X3Y1), (A2, B2, M2, N2, R5b, R6a, X4Y3), (A2, B2, M2, N2, R5b, R6a, X5Y1), (A2, B2, M2, N2, R5b, R6b, X1Y1), (A2, B2, M2, N2, R5b, R6b, X1Y2), (A2, B2, M2, N2, R5b, R6b, X2Y1), (A2, B2, M2, N2, R5b, R6b, X3Y1), (A2, B2, M2, N2, R5b, R6b, X4Y3), (A2, B2, M2, N2, R5b, R6b, X5Y1), (A2, B3, M1, N1, R5a, R6a, X1Y1), (A2, B3, M1, N1, R5a, R6a, X1Y2), (A2, B3, M1, N1, R5a, R6a, X2Y1), (A2, B3, M1, N1, R5a, R6a, X3Y1), (A2, B3, M1, N1, R5a, R6a, X4Y3), (A2, B3, M1, N1, R5a, R6a, X5Y1), (A2, B3, M1, N1, R5a, R6b, X1Y1), (A2, B3, M1, N1, R5a, R6b, X1Y2), (A2, B3, M1, N1, R5a, R6b, X2Y1), (A2, B3, M1, N1, R5a, R6b, X3Y1), (A2, B3, M1, N1, R5a, R6b, X4Y3), (A2, B3, M1, N1, R5a, R6b, X5Y1), (A2, B3, M1, N1, R5b, R6a, X1Y1), (A2, B3, M1, N1, R5b, R6a, X1Y2), (A2, B3, M1, N1, R5b, R6a, X2Y1), (A2, B3, M1, N1, R5b, R6a, X3Y1), (A2, B3, M1, N1, R5b, R6a, X4Y3), (A2, B3, M1, N1, R5b, R6a, X5Y1), (A2, B3, M1, N1, R5b, R6b, X1Y1), (A2, B3, M1, N1, R5b, R6b, X1Y2), (A2, B3, M1, N1, R5b, R6b, X2Y1), (A2, B3, M1, N1, R5b, R6b, X3Y1), (A2, B3, M1, N1, R5b, R6b, X4Y3), (A2, B3, M1, N1, R5b, R6b, X5Y1), (A2, B3, M1, N2, R5a, R6a, X1Y1), (A2, B3, M1, N2, R5a, R6a, X1Y2), (A2, B3, M1, N2, R5a, R6a, X2Y1), (A2, B3, M1, N2, R5a, R6a, X3Y1), (A2, B3, M1, N2, R5a, R6a, X4Y3), (A2, B3, M1, N2, R5a, R6a, X5Y1), (A2, B3, M1, N2, R5a, R6b, X1Y1), (A2, B3, M1, N2, R5a, R6b, X1Y2), (A2, B3, M1, N2, R5a, R6b, X2Y1), (A2, B3, M1, N2, R5a, R6b, X3Y1), (A2, B3, M1, N2, R5a, R6b, X4Y3), (A2, B3, M1, N2, R5a, R6b, X5Y1), (A2, B3, M1, N2, R5b, R6a, X1Y1), (A2, B3, M1, N2, R5b, R6a, X1Y2), (A2, B3, M1, N2, R5b, R6a, X2Y1), (A2, B3, M1, N2, R5b, R6a, X3Y1), (A2, B3, M1, N2, R5b, R6a, X4Y3), (A2, B3, M1, N2, R5b, R6a, X5Y1), (A2, B3, M1, N2, R5b, R6b, X1Y1), (A2, B3, M1, N2, R5b, R6b, X1Y2), (A2, B3, M1, N2, R5b, R6b, X2Y1), (A2, B3, M1, N2, R5b, R6b, X3Y1), (A2, B3, M1, N2, R5b, R6b, X4Y3), (A2, B3, M1, N2, R5b, R6b, X5Y1), (A2, B3, M2, N1, R5a, R6a, X1Y1), (A2, B3, M2, N1, R5a, R6a, X1Y2), (A2, B3, M2, N1, R5a, R6a, X2Y1), (A2, B3, M2, N1, R5a, R6a, X3Y1), (A2, B3, M2, N1, R5a, R6a, X4Y3), (A2, B3, M2, N1, R5a, R6a, X5Y1), (A2, B3, M2, N1, R5a, R6b, X1Y1), (A2, B3, M2, N1, R5a, R6b, X1Y2), (A2, B3, M2, N1, R5a, R6b, X2Y1), (A2, B3, M2, N1, R5a, R6b, X3Y1), (A2, B3, M2, N1, R5a, R6b, X4Y3), (A2, B3, M2, N1, R5a, R6b, X5Y1), (A2, B3, M2, N1, R5b, R6a, X1Y1), (A2, B3, M2, N1, R5b, R6a, X1Y2), (A2, B3, M2, N1, R5b, R6a, X2Y1), (A2, B3, M2, N1, R5b, R6a, X3Y1), (A2, B3, M2, N1, R5b, R6a, X4Y3), (A2, B3, M2, N1, R5b, R6a, X5Y1), (A2, B3, M2, N1, R5b, R6b, X1Y1), (A2, B3, M2, N1, R5b, R6b, X1Y2), (A2, B3, M2, N1, R5b, R6b, X2Y1), (A2, B3, M2, N1, R5b, R6b, X3Y1), (A2, B3, M2, N1, R5b, R6b, X4Y3), (A2, B3, M2, N1, R5b, R6b, X5Y1), (A2, B3, M2, N2, R5a, R6a, X1Y1), (A2, B3, M2, N2, R5a, R6a, X1Y2), (A2, B3, M2, N2, R5a, R6a, X2Y1), (A2, B3, M2, N2, R5a, R6a, X3Y1), (A2, B3, M2, N2, R5a, R6a, X4Y3), (A2, B3, M2, N2, R5a, R6a, X5Y1), (A2, B3, M2, N2, R5a, R6b, X1Y1), (A2, B3, M2, N2, R5a, R6b, X1Y2), (A2, B3, M2, N2, R5a, R6b, X2Y1), (A2, B3, M2, N2, R5a, R6b, X3Y1), (A2, B3, M2, N2, R5a, R6b, X4Y3), (A2, B3, M2, N2, R5a, R6b, X5Y1), (A2, B3, M2, N2, R5b, R6a, X1Y1), (A2, B3, M2, N2, R5b, R6a, X1Y2), (A2, B3, M2, N2, R5b, R6a, X2Y1), (A2, B3, M2, N2, R5b, R6a, X3Y1), (A2, B3, M2, N2, R5b, R6a, X4Y3), (A2, B3, M2, N2, R5b, R6a, X5Y1), (A2, B3, M2, N2, R5b, R6b, X1Y1), (A2, B3, M2, N2, R5b, R6b, X1Y2), (A2, B3, M2, N2, R5b, R6b, X2Y1), (A2, B3, M2, N2, R5b, R6b, X3Y1), (A2, B3, M2, N2, R5b, R6b, X4Y3) or (A2, B3, M2, N2, R5b, R6b, X5Y1).

Further examples of A include, for example, a group selected from the group consisting of the followings:

[Chemical Formula 16]

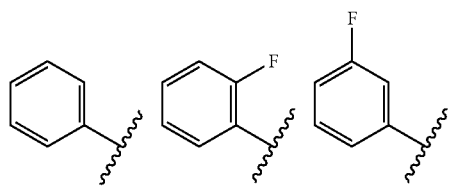

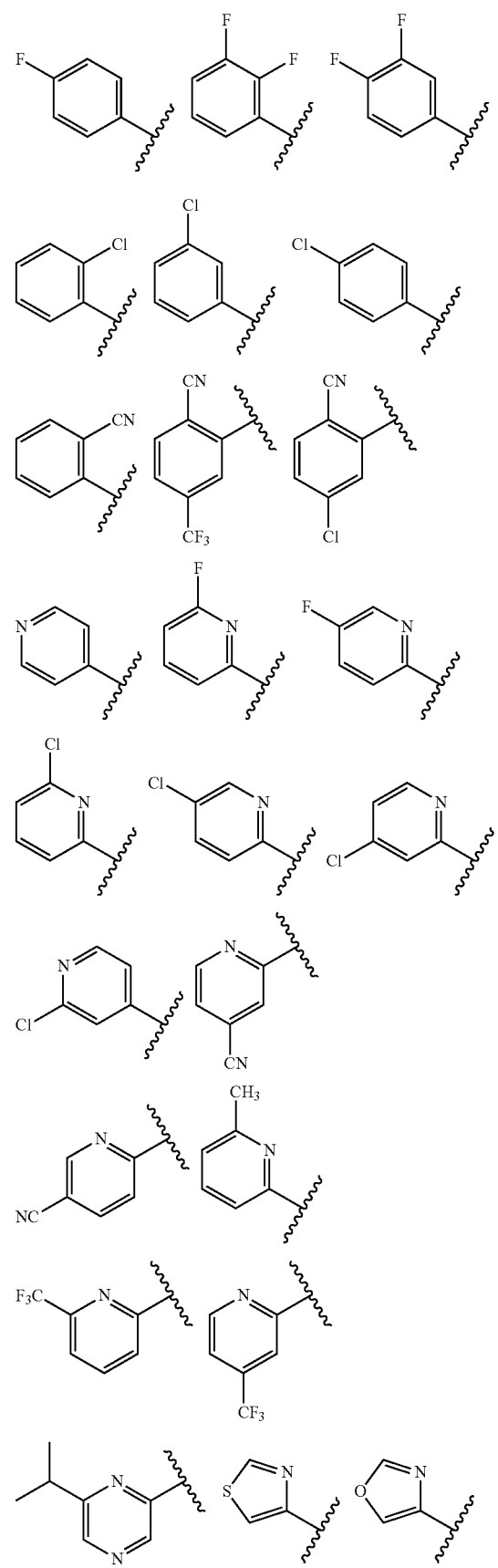

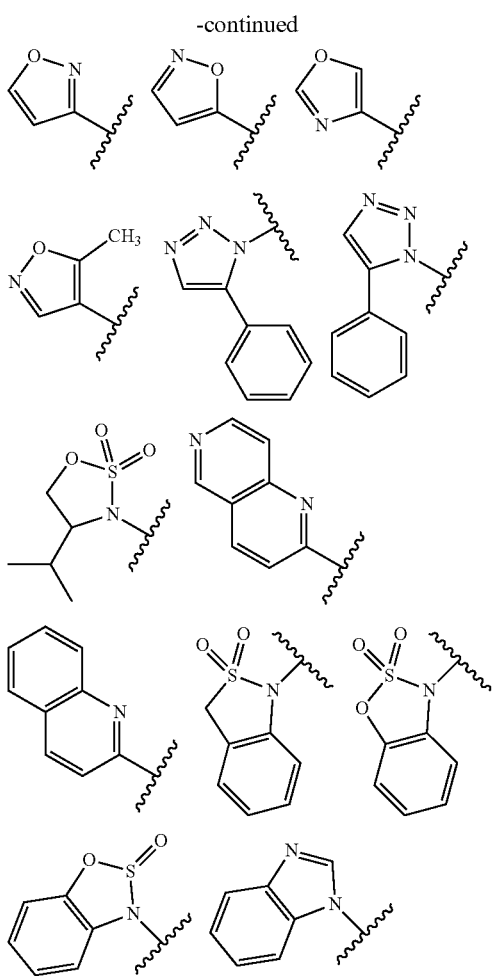

wherein the bond from the groups binds to X.

Further examples of B include, for example, a group selected from the group consisting of the followings:

[Chemical Formula 17]

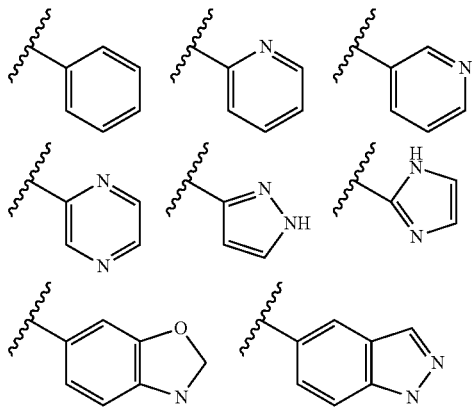

wherein the bond from the groups binds to Y and each ring is substituted or unsubstituted with m $R^5$s and n $R^6$s.

Further examples of $R^5$ include, for example, a group selected from a group consisting of the followings:

[Chemical Formula 18]

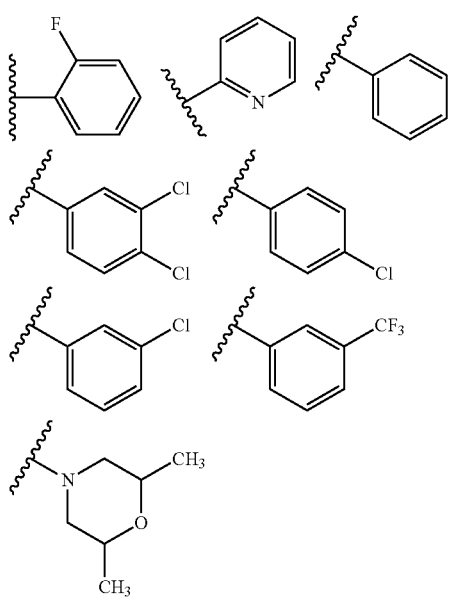

wherein the from the groups binds to B.

Further examples of $R^6$ include, for example, a group selected from a group consisting of the followings:

[Chemical Formula 19]

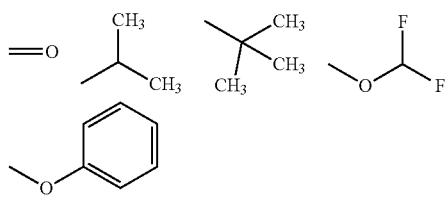

wherein the from the groups binds to B.

The compound of the formula (I) is a compound of the formula (I-1):

[Chemical Formula 20]

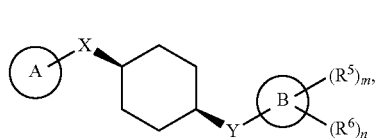

(I-1)

wherein each symbol is as defined for formula (I), or a compound of the formula (I-2):

[Chemical Formula 21]

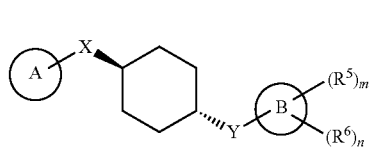

(I-2)

wherein each symbol is as defined for formula (I). Particularly preferable compound is a compound of the formula (I-1):

[Chemical Formula 22]

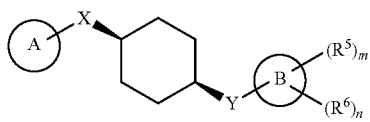

(I-1)

wherein each symbol is as defined for the formula (I).

The compound of the formula (I) of the present invention can be synthesized by, for example, as described below. If necessary, an amino group or an imino group of the compound may be protected at appropriate stage according to a conventional method, for example, using a protecting group such as Cbz (benzyloxycarbonyl), Fmoc (9-Fluororenylmethyloxycarbonyl), Boc (tert-butoxycarbonyl) conventionally used in the art.

vent at 0° C. to 50° C. for several minutes to several hours. For the reaction solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixed solvent thereof may be used.

Step B

Compound 3 is obtained by reacting Compound 2 with an amino compound having a desired substituent Z in an appropriate solvent at 0° C. to 50° C. for several minutes to several hours. For the reaction solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and a mixed solvent thereof may be used. If necessary, an activating agent such as thionyl chloride, acid halide, acid anhydrate, activated ester, etc., may be used.

Step C

Compound 4 is obtained by reacting Compound 1 with an amino compound having a desired substituent Z in an appropriate solvent at 0° C.-50° C. for several minutes to several

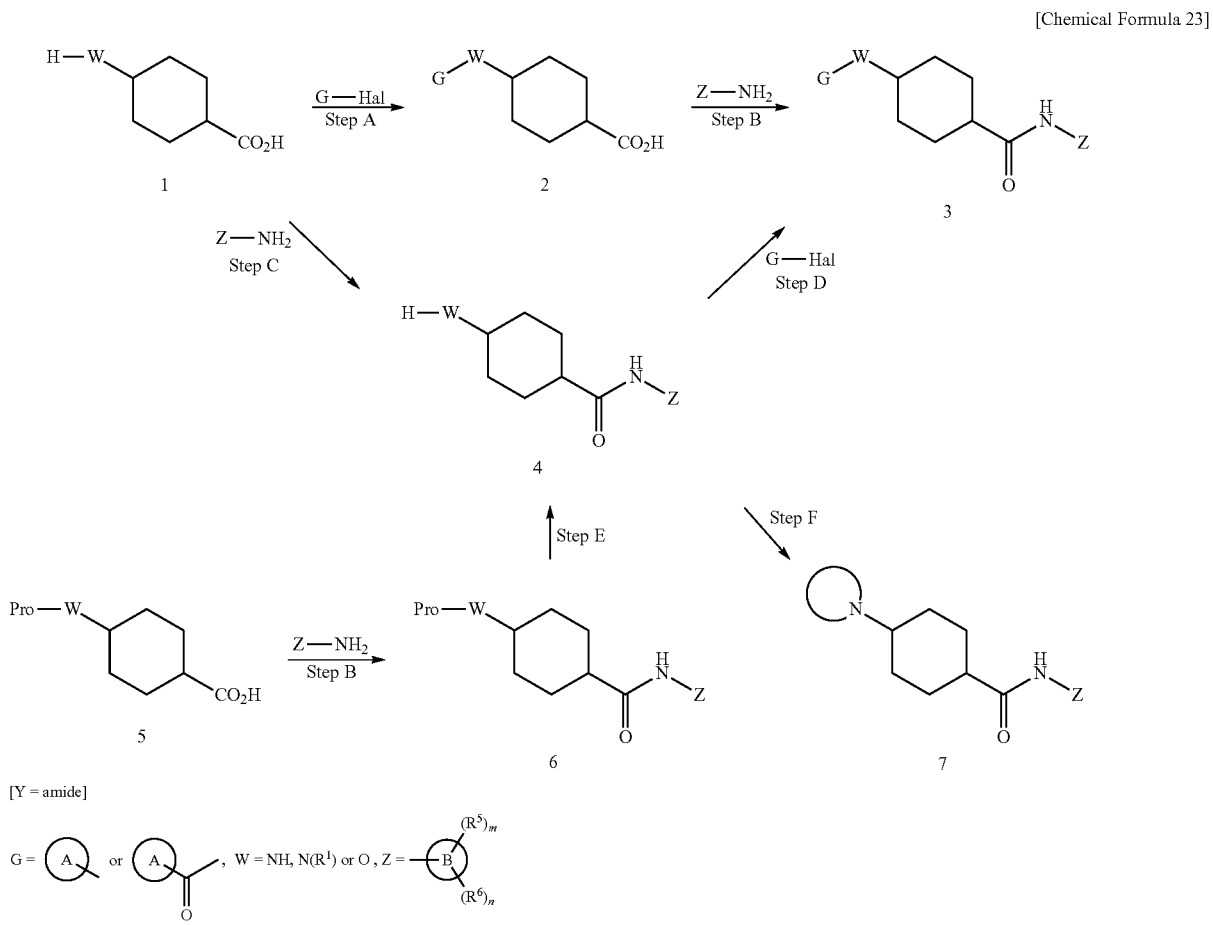

wherein Hal is halogen, Pro is a protecting group and the other symbols are as defined above.

Step A

Compound 2 is obtained by reacting Compound 1 with a halide having a desired substituent G in an appropriate solhours. For the reaction solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and a mixed solvent thereof may be used. If necessary, an activating agent such as thionyl chloride, acid halide, acid anhydride, activated ester, etc., may be used.

Step D

Compound 3 is obtained by reacting Compound 4 with a halide having a desired substituent G in an appropriate solvent at 0° C. to 50° C. for several minutes to several hours. For the reaction solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixed solvent thereof may be used.

Step E

Also, Compound 4 can be obtained by subjecting Compound 6 to deprotection by conventional method.

Step F

Compound 7 is obtained by converting a substituent —W—H in Compound 4 to an amino functional group using a conventional method. For example, when the substituent —W—H is a hydroxyl group, Compound 7 is obtained by subjecting Compound 4 to substitution reaction with an amino compound through a mesylate compound.

Method 2

[Chemical Formula 24]

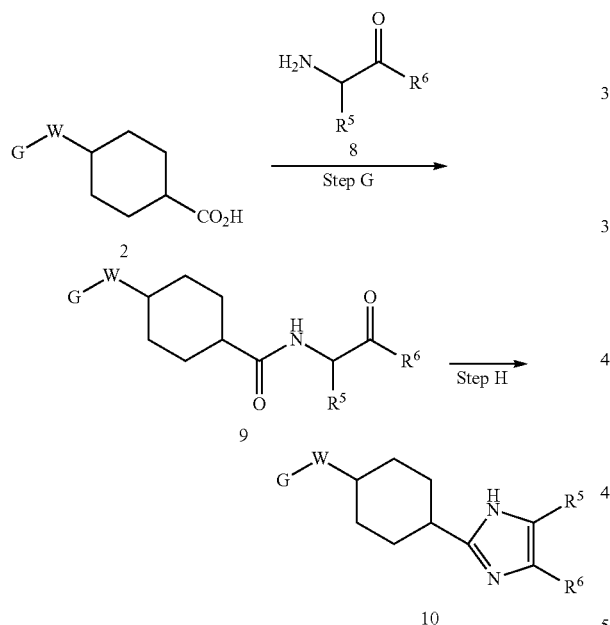

[B = imidazole]

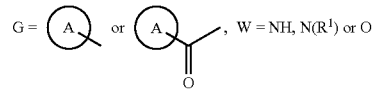, W = NH, N(R$^1$) or O wherein each of G and W is a substituent group corresponding to the desired compound and the other symbols are as defined above.

Step G

Compound 9 is obtained by reacting Compound 2 with an amino compound 8 having a desired substituent R$^5$ and R$^6$ in an appropriate solvent at 0° C. to 50° C. for several minutes to several hours. For the reaction solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and a mixed solvent thereof may be used. If necessary, an activating agent such as thionyl chloride, acid halides, acid anhydrides and activated esters may be used.

Step H

Compound 10 is obtained by reacting Compound 9 with ammonium acetate in an appropriate solvent at room temperature to 150° C. for several minutes to several hours. For the solvent, acetic acid, methylene chloride, tetrahydrofuran, dimethylformamide, dimethylacetamide, N-methylpyrrolidone, diethyl ether, diisopropyl ether, 1,2-dichloroethane, toluene, benzene, xylene, cyclohexane, hexane, chloroform, ethyl acetate, butyl acetate, pentane, heptane, dioxane, acetone, methanol, ethanol, propanol, acetonitrile, water and a mixed solvent thereof may be used. Acetic acid is preferable.

Method 3

[Chemical Formula 25]

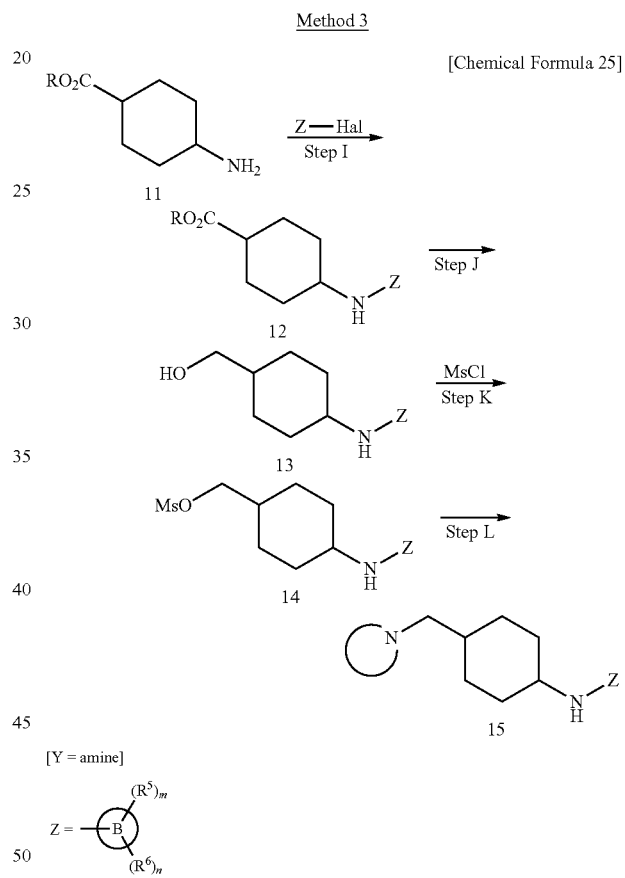

[Y = amine]

Z = ⟨B⟩ (R$^5$)$_m$ (R$^6$)$_n$ wherein the symbols are as defined above.

Step I

Compound 12 is obtained by reacting Compound 11 with a halide having a desired substituent Z in an appropriate solvent at 0° C. to 50° C. for several minutes to several hours. For the solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixed solvent thereof may be used.

Step J

Compound 13 is obtained by treating Compound 12 with a reducing agent in an appropriate solvent at 0° C. to 100° C. for several minutes to several hours. For the reducing agent, sodium boron hydride, lithium boron hydride, lithium aluminum hydride and diborane may be used. For the solvent, tetrahydrofuran, dimethylformamide, dioxane, acetonitrile, methanol, ethanol, propanol and a mixed solvent thereof may be used. If necessary, Compound 13 may be prepared through an intermediate such as acid halide, acid anhydride or activated ester.

Step K

Compound 14 is obtained by treating Compound 13 with mesyl chloride in an appropriate solvent at 0° C. to 100° C. for several minutes to several hours. For the solvent, tetrahydrofuran, dimethylformamide, dioxane, acetonitrile, and a mixed solvent thereof may be used.

Step L

Compound 15 is obtained by converting the mesyl group in Compound 14 to an amino functional group using a conventional method.

Those skilled in the art can prepare a compound of the formula (I) by reference to the above steps or by taking advantage of their knowledge of synthetic organic chemistry.

When administering a compound of the present invention as a pharmaceutical composition, it can be administered orally or parenterally. For oral administration, the compound of the present invention can be used in any form of usual formulations, for example, tablets, granules, powders, capsules, pills, solutions, syrup, buccals, sublingual tablets or the like which are made by the usual procedure. For parenteral administration, the compound of the present invention can be used in any form of usual formulations, for example, injections such as intramuscular administration and intravenous administration, suppository, transdermal therapeutic agent, insufflation or the like. A compound of the present invention can be preferably used as an oral formulation because it has high oral bioavailability.

The pharmaceutical formulation according to the present invention may be manufactured by combining a therapeutically effective amount of a compound of the present invention with various pharmaceutically acceptable excipients, binder, moistening agent, disintegrating agents, lubricant, diluent and the like. When it is an injectable formulation, the compound of the present invention may be subjected to sterilization treatment together with an appropriate carrier to obtain such formulation.

Specifically, the excipient includes lactose, saccharose, glucose, starch, calcium carbonate, crystalline cellulose and the like. The binder includes methylcellulose, carboxymethylcellulose, hydroxypropylcellulose, gelatin, polyvinylpyrrolidone and the like. The disintegrating agent includes carboxymethylcellulose, sodium carboxymethylcellulose, starch, sodium alginate, powdered agar, sodium lauryl sulfate and the like. The lubricant includes talc, magnesium stearate, macrogol and the like. As a basis for suppository, cocoa butter, macrogol, methyl cellulose and the like can be used. When the present invention is manufactured as an injectable formulation of liquid, emulsion or suspension, conventionally used solubilizing agent, suspending agent, emulsifying agent, stabilizing agent, preservatives, isotonic agent and the like may be appropriately added. In case of oral formulation, sweetening agent, flavoring agent and the like may be added.

The dose of a compound of the present invention is preferably determined depending on age, body weight, type and severity of disease of the patient, administration route, and the like. In case of oral administration for an adult, it is usually 0.05 to 100 mg/kg/day and preferably 0.1 to 10 mg/kg/day. In case of parenteral administration, although it is very different depending on route of administration, it is usually 0.005 to 10 mg/kg/day and preferably 0.01 to 1 mg/kg/day. The dose may be administrated at once or divided to several times a day.

The pharmaceutical composition of the present invention can be used in combination with other anti-obesity agent (agents that can be used in obesity and weight control in obesity). Also, the administration regimen of the pharmaceutical composition of the invention may be combined with diet, drug therapy, exercise, etc.

The present invention is further explained by the following Examples, which are not intended to limit the scope of the present invention.

The abbreviations used in the following Examples have the following meanings.

EDC: 1-ethyl-3-(3-dimethylaminopropyl)carbodiimide
HOBt: 1-hydroxybenzotriazole

Example 1

Synthesis of Compound Ia-37

Step 1

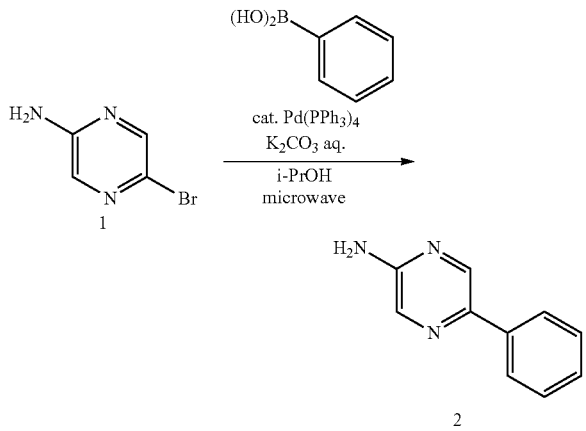

[Chemical Formula 26]

2-amino-5-bromopyridine 1 (522 mg, 3.00 mmol), phenylboronic acid (732 mg, 6.00 mmol), an aqueous solution of 2M potassium carbonate (6 ml, 12.0 mmol) and tetrakis(triphenylphosphine)palladium complex (104 mg, 90.0 µmol) were suspended in 6 ml of isopropyl alcohol, and the suspension was sealed and stirred for ten minutes at 150° C. using a microwave reactor. The reaction mixture was poured into water and extracted with ethyl acetate. The organic layer was washed with water and brine, and dried over magnesium sulfate. The solvent was removed in vacuo, and the residue was purified by silica gel chromatography to yield amine compound 2 (512.4 mg, yield 99%).

Step 2

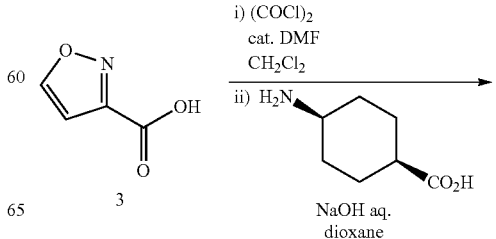

[Chemical Formula 27]

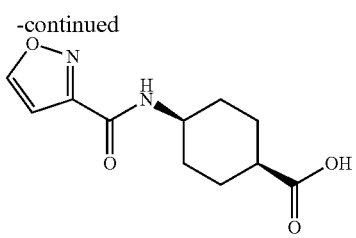

4

Carboxylic acid 3 (5.66 g, 50.1 mmol) was suspended in 57 ml of methylene chloride, and oxalyl chloride (5.4 ml, 60.1 mmol) was added to the suspension. 4 drops of N,N-dimethylformamide was carefully added dropwise, and the mixture was stirred for 1 hour at room temperature.

In another reaction vessel, cis-4-amino-1-cyclohexylcarbonic acid (8.6 g, 60.1 mmol) was suspended in 57 ml of 1,4-dioxane. 2N sodium hydroxide (60 ml, 120.2 mmol) and followed by a solution of methylene chloride obtained in the above step were added dropwise at 0° C., and the mixture was stirred overnight at room temperature. The reaction mixture was poured into 2N hydrochloric acid to acidify and extracted with ethyl acetate. The organic layer was washed with water and brine and dried over magnesium sulfate. The resulting residue was suspended with heating, and the solution was allowed to stand at room temperature to yield carboxylic acid 4 (8.49 g, yield 71%) after filtration. $^1$H-NMR (DMSO-$d_6$) δ: 1.53-1.72 (m, 6H), 1.97-2.03 (m, 2H), 2.52-2.53 (m, 1H), 3.82-3.90 (m, 1H), 6.90 (d, 1H, J=1.5 Hz), 8.58 (d, 1H, J=7.2 Hz), 9.07 (d, 1H, J=1.5 Hz), 12.17 (s, 1H).

Step 3

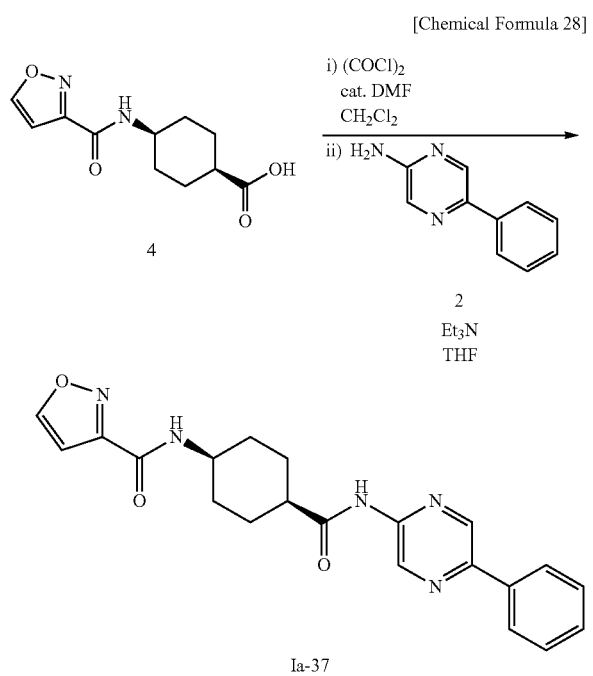

Carboxylic acid 4 (200 mg, 0.84 mmol) obtained in Step 2 was suspended in 2 ml of methylene chloride, and oxalyl chloride (90 μl, 1.01 mmol) was added to the suspension. 2 drops of N,N-dimethylformamide was carefully added dropwise, and the mixture was stirred for 1 hour at room temperature.

In another reaction vessel, amine compound 2 (131 mg, 0.76 mmol) obtained in Step 1 was suspended in 2 ml of tetrahydrofuran, and the solution of methylene chloride obtained above and followed by triethylamine (425 μl, 3.05 mmol) were added dropwise at 0° C., and the mixture was stirred overnight at room temperature. The reaction mixture was poured into saturated aqueous sodium bicarbonate and extracted with ethyl acetate. The organic layer was washed with water and brine and dried over magnesium sulfate. The solvent was removed in vacuo, and the residue was purified by silica gel chromatography. The solvent was removed, and ethyl acetate and hexane were added to the resulting residue. The precipitated crystals were filtered off to yield a desired compound Ia-37 (125.3 mg, yield 42%).

$^1$H-NMR (DMSO-$d_6$) δ: 1.63-2.05 (m, 8H), 2.69-2.77 (m, 1H), 3.98-4.07 (m, 1H), 6.93 (d, 1H, J=2.4 Hz), 7.48-7.57 (m, 3H), 8.11-8.14 (m, 2H), 8.55-8.58 (m, 1H), 9.02-9.09 (m, 2H), 9.43-9.44 (m, 1H), 10.79 (s, 1H).

Example 2

Synthesis of Compound Ic-3

Step 1

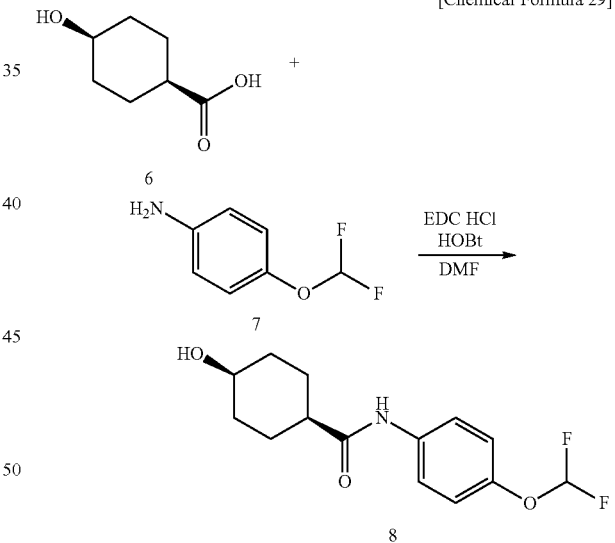

To a solution of cis-4-hydroxycyclohexane carbonic acid 6 (6.14 g, 42.6 mmol) in N,N'-dimethylformamide (40 mL) were added 4-difluoromethoxyaniline 7 (5.12 g, 35.5 mmol), HOBt (691 mg, 5.11 mmol) and EDC hydrochloride (9.77 g, 51.1 mmol) at room temperature, and the mixture was stirred overnight at room temperature. The reaction solution was poured into 1N hydrochloric acid and extracted with ethyl acetate, and then the organic layer was washed with saturated aqueous sodium bicarbonate and dried over magnesium sulfate, and then a solvent was removed in vacuo. The residue was washed with diethyl ether to yield the desired amide compound 8 (7.10 g, yield 70%) as a colorless solid.

Step 2

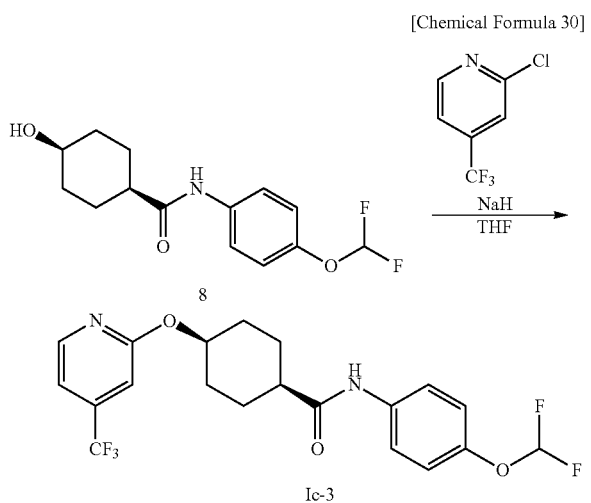

To a solution of Compound 8 (228 mg, 0.800 mmol) obtained in Step 1 in dimethoxyethane (2 mL) was added sodium hydride (60%, 106 mg, 2.64 mmol) at 0° C., and the mixture was stirred for 1 hour at the same temperature, and then 2-fluorobenzonitrile (130 μL, 1.20 mmol) was added thereto and stirred for 2.5 hours at 80° C. The reaction solution was cooled to room temperature, and then poured into saturated brine and extracted with ethyl acetate, and dried over magnesium sulfate, and then a solvent was removed in vacuo. The residue was purified by column chromatography (n-hexane:ethyl acetate=60:40→50:50) using silica gel (12 g) to yield the desired compound Ic-3 (246 mg, yield 80%)

$^1$H-NMR (DMSO-d$_6$) δ: 1.42-1.53 (m, 2H), 1.57-1.69 (m, 2H), 1.93-1.99 (m, 2H), 2.17-2.25 (m, 2H), 2.34-2.44 (m, 1H), 5.00-5.08 (m, 1H), 7.12 (t, 1H, J=74.4 Hz), 7.12-7.14 (m, 3H), 7.29 (d, 1H, J=4.8 Hz), 7.66 (d, 2H, J=8.8 Hz), 8.44 (d, 1H, J=4.8 Hz), 10.04 (s, 1H).

Example 3

Synthesis of Compound Id-1

[Chemical Formula 31]

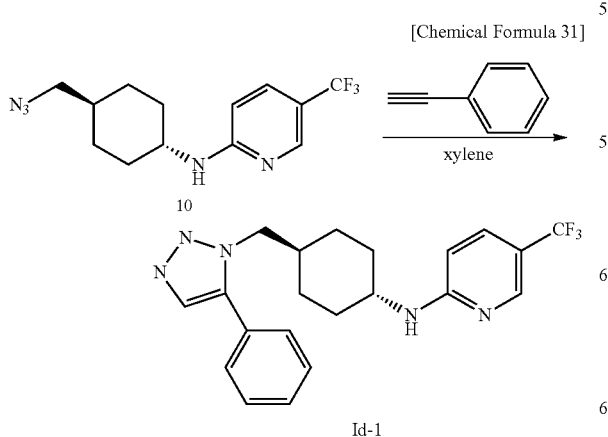

To a solution of azide 10 (synthesized according to WO2007/125952) (300 mg, 1.00 mmol) in xylene (3 mL) was added phenylacetylene (549 μL, 5.00 mmol) at room temperature, and then stirred at 120° C. overnight. A solvent was removed from the reaction solution under reduced pressure, and then the residue was purified by silica gel chromatography (n-hexane:ethyl acetate=80:20→50:50). The solvent was removed in vacuo, and to the resulting residue were added ethyl acetate and hexane, and then the precipitated crystals were filtered off to yield the desired triazole compound Id-1 (86 mg, yield 21%).

$^1$H-NMR (DMSO-d$_6$) δ: 0.92-1.14 (m, 4H), 1.42-1.53 (m, 2H), 1.73 (bs, 1H), 1.85-1.93 (m, 2H), 3.65 (bs, 1H), 4.32 (d, 2H, J=7.14 Hz), 6.51 (d, 1H, J=9.06 Hz), 7.17 (d, 1H, J=7.42 Hz), 7.51-7.61 (m, 6H), 7.89 (s, 1H), 8.23 (s, 1H).

The following compounds were synthesized in similar manner as described above. The structural formulae and the physical properties of these compounds are shown below.

[Chemical Formula 32]

Compound Ia-1

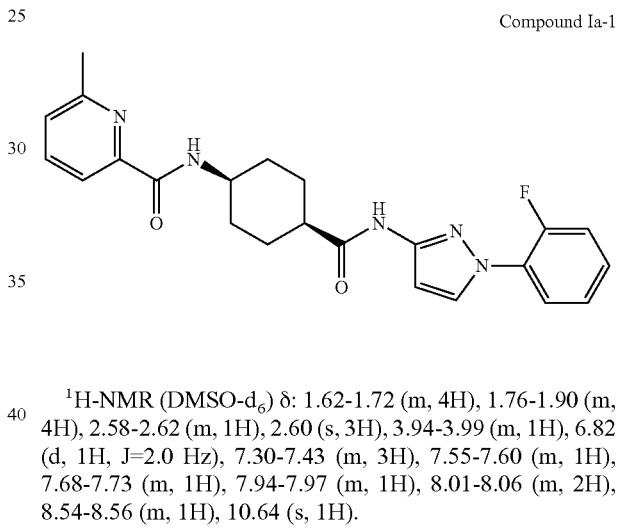

$^1$H-NMR (DMSO-d$_6$) δ: 1.62-1.72 (m, 4H), 1.76-1.90 (m, 4H), 2.58-2.62 (m, 1H), 2.60 (s, 3H), 3.94-3.99 (m, 1H), 6.82 (d, 1H, J=2.0 Hz), 7.30-7.43 (m, 3H), 7.55-7.60 (m, 1H), 7.68-7.73 (m, 1H), 7.94-7.97 (m, 1H), 8.01-8.06 (m, 2H), 8.54-8.56 (m, 1H), 10.64 (s, 1H).

[Chemical Formula 33]

Compound Ia-2

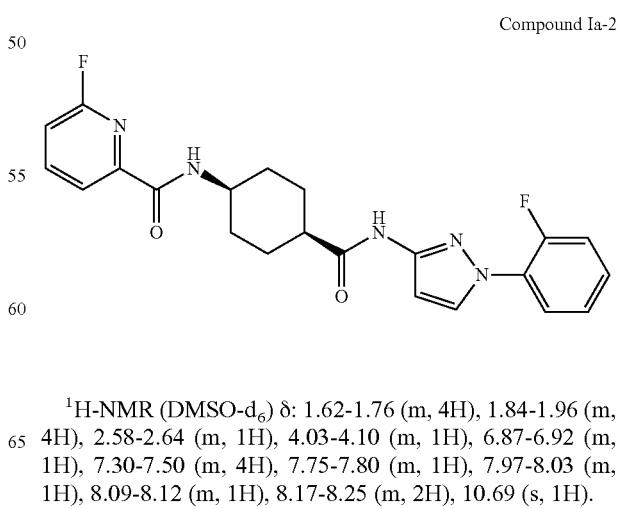

$^1$H-NMR (DMSO-d$_6$) δ: 1.62-1.76 (m, 4H), 1.84-1.96 (m, 4H), 2.58-2.64 (m, 1H), 4.03-4.10 (m, 1H), 6.87-6.92 (m, 1H), 7.30-7.50 (m, 4H), 7.75-7.80 (m, 1H), 7.97-8.03 (m, 1H), 8.09-8.12 (m, 1H), 8.17-8.25 (m, 2H), 10.69 (s, 1H).

[Chemical Formula 34]

Compound Ia-3

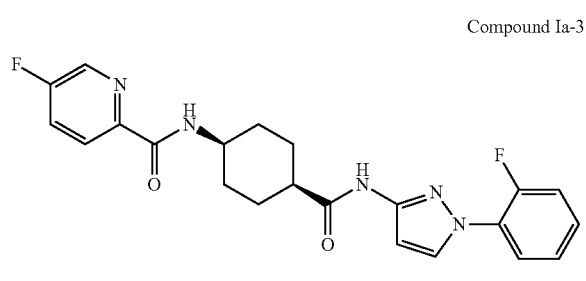

¹H-NMR (DMSO-d₆) δ: 1.50-2.02 (m, 8H), 2.48-2.58 (m, 1H), 4.01-4.07 (m, 1H), 6.86 (s, 1H), 7.37-7.39 (m, 5H), 8.11 (s, 1H), 8.52-8.69 (m, 3H), 10.64 (s, 1H).

[Chemical Formula 35]

Compound Ia-4

¹H-NMR (DMSO-d₆) δ: 1.65-1.75 (m, 4H), 1.81-1.98 (m, 4H), 2.58-2.63 (m, 1H), 3.99-4.08 (m, 1H), 6.87-6.91 (m, 1H), 7.32-7.50 (m, 3H), 7.70-7.80 (m, 2H), 7.98-8.14 (m, 3H), 8.22-8.30 (m, 1H), 10.68 (s, 1H).

[Chemical Formula 36]

Compound Ia-5

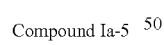

¹H-NMR (DMSO-d₆) δ: 1.78-1.93 (m, 8H), 2.56-2.59 (m, 1H), 4.04-4.07 (m, 1H), 7.21-7.54 (m, 7H), 7.66 (d, 1H, J=7.2 Hz), 7.75-7.78 (m, 1H), 7.91 (d, 1H, J=1.3 Hz), 8.02-8.11 (m, 2H), 8.26 (d, 1H, J=7.9 Hz), 9.97 (s, 1H).

[Chemical Formula 37]

Compound Ia-6

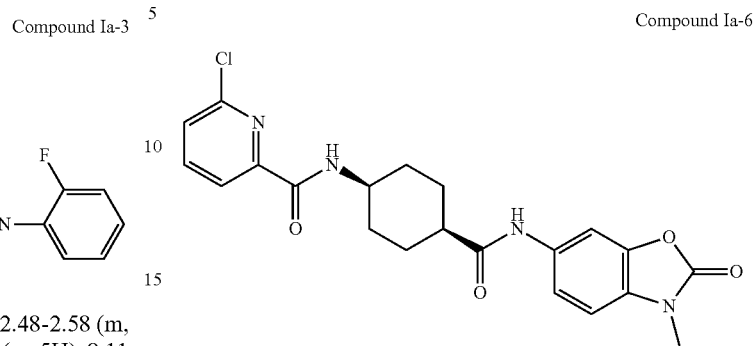

¹H-NMR (DMSO-d₆) δ: 1.47 (d, 6H, J=6.9 Hz), 1.73-1.88 (m, 8H), 3.30-3.35 (m, 1H), 4.03-4.06 (m, 1H), 4.46-4.48 (m, 1H), 7.34-7.38 (m, 2H), 7.76-7.79 (m, 2H), 8.04-8.09 (m, 2H), 8.25 (d, 1H, J=7.7 Hz), 9.95 (s, 1H).

[Chemcial Formula 38]

Compound Ia-7

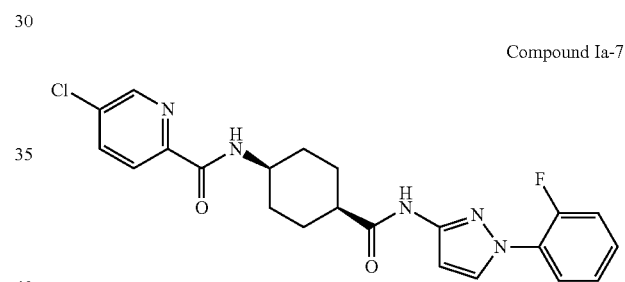

¹H-NMR (DMSO-d₆) δ: 1.65-1.80 (m, 4H), 1.81-1.97 (m, 4H), 2.58-2.66 (m, 1H), 4.07-4.15 (m, 1H), 6.89-6.92 (m, 1H), 7.34-7.51 (m, 3H), 7.65-7.72 (m, 1H), 8.05-8.17 (m, 3H), 8.37 (d, 1H, J=7.2 Hz), 8.74 (s, 1H), 10.71 (s, 1H).

[Chemical Formula 39]

Compound Ia-8

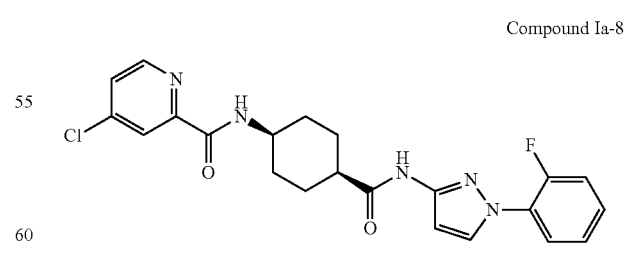

¹H-NMR (DMSO-d₆) δ: 1.60-1.72 (m, 4H), 1.72-1.89 (m, 4H), 2.51-2.59 (m, 1H), 4.00-4.10 (m, 1H), 6.81-6.84 (m, 1H), 7.27-7.42 (m, 3H), 7.67-7.74 (m, 2H), 7.97-8.05 (m, 2H), 8.39 (d, 1H, J=7.6 Hz), 8.61 (d, 1H, J=5.2 Hz), 10.62 (s, 1H).

[Chemical Formula 40]

Compound Ia-9

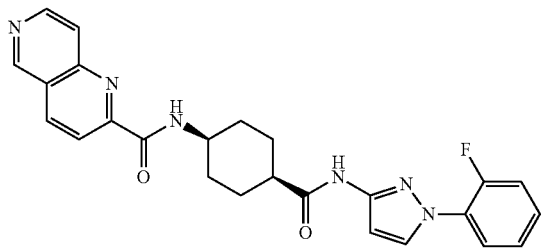

¹H-NMR (DMSO-d₆) δ: 1.66-1.76 (m, 4H), 1.82-1.96 (m, 4H), 2.54-2.62 (m, 1H), 4.04-4.08 (m, 1H), 6.81-6.84 (m, 1H), 7.28-7.43 (m, 3H), 7.67-7.73 (m, 1H), 8.02-8.05 (m, 2H), 8.24 (d, 1H, J=7.6 Hz), 8.65 (d, 1H, J=8.0 Hz), 8.74 (d, 1H, J=8.4 Hz), 8.78 (d, 1H, J=6.0 Hz), 9.45 (s, 1H) 10.62 (s, 1H).

[Chemical Formula 41]

Compound Ia-10

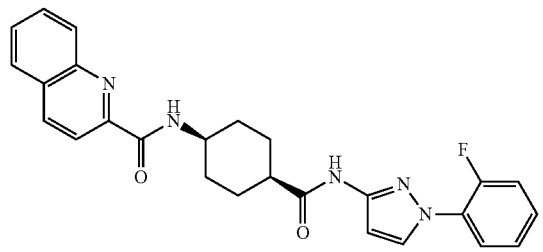

¹H-NMR (DMSO-d₆) δ: 1.67-2.06 (m, 8H), 2.60-2.68 (m, 1H), 4.07-4.14 (m, 1H), 6.89 (d, J=2.1 Hz, 1H), 7.34-7.45 (m, 3H), 7.69-7.78 (m, 2H), 7.84-7.89 (m, 1H), 8.07-8.20 (m, 4H), 8.56-8.59 (m, 2H), 10.70 (s, 1H).

[Chemical Formula 42]

Compound Ia-11

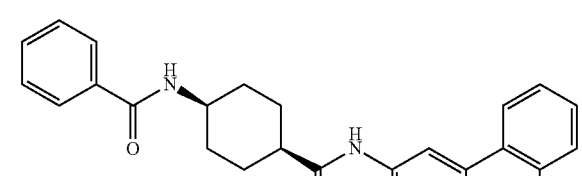

¹H-NMR (DMSO-d₆) δ: 1.58-1.68 (m, 4H), 1.79-2.01 (m, 4H), 2.52-2.60 (m, 1H), 3.95-3.97 (m, 1H), 6.82-6.84 (m, 1H), 7.30-7.44 (m, 3H), 7.69-7.75 (m, 3H), 8.02-8.07 (m, 1H), 8.52 (d, 1H, J=7.2 Hz), 8.68 (d, 1H, J=4.8 Hz), 10.58 (s, 1H).

[Chemical Formula 43]

Compound Ia-12

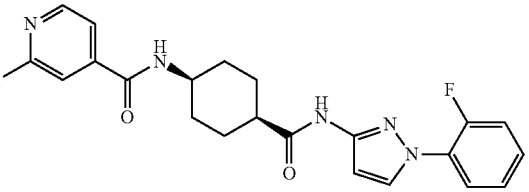

¹H-NMR (DMSO-d₆) δ: 1.58-1.68 (m, 4H), 1.78-2.00 (m, 4H), 2.52-2.60 (m, 1H), 3.94-3.96 (m, 1H), 6.83 (d, 1H, J=2.0 Hz), 7.29-7.44 (m, 3H), 7.69-7.75 (m, 2H), 7.84 (s, 1H), 8.02-8.07 (m, 1H), 8.51 (d, 1H, J=4.8 Hz), 8.60 (d, 1H, J=7.2 Hz), 10.58 (s, 1H).

[Chemical Formula 44]

Compound Ia-13

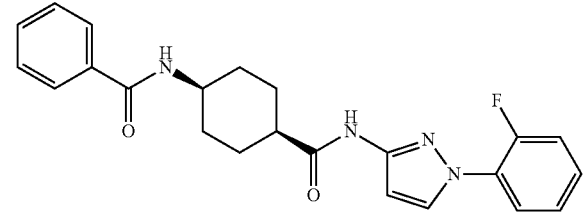

¹H-NMR (DMSO-d₆) δ: 1.64-2.01 (m, 8H), 2.57-2.63 (m, 1H), 3.99-4.04 (m, 1H), 6.88 (d, 1H, J=2.4 Hz), 7.34-7.56 (m, 6H), 7.74-7.89 (m, 3H), 8.10-8.22 (m, 2H), 10.62 (s, 1H).

[Chemical Formula 45]

Compound Ia-14

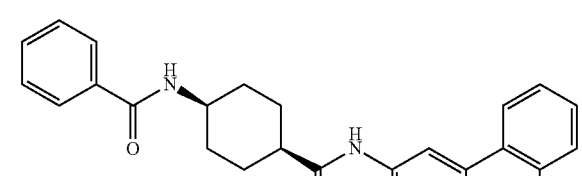

¹H-NMR (DMSO-d₆) δ: 1.65-1.68 (m, 4H), 1.90-2.04 (m, 4H), 2.51-2.60 (m, 1H), 3.98-4.01 (m, 1H), 7.21-7.55 (m, 9H), 7.66 (d, 1H, J=9.1 Hz), 7.86-7.91 (m, 3H), 8.22 (d, 1H, J=7.1 Hz), 9.92 (s, 1H).

[Chemical Formula 46]

Compound Ia-15

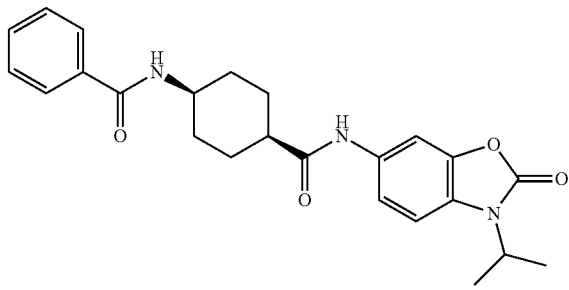

$^1$H-NMR (DMSO-$d_6$) δ: 1.47 (d, 6H, J=6.9 Hz), 1.64-1.67 (m, 4H), 1.88-2.01 (m, 4H), 3.32-3.33 (m, 1H), 3.98-4.01 (m, 1H), 4.46-4.48 (m, 1H), 7.31-7.53 (m, 5H), 7.83-7.87 (m, 3H), 8.22 (d, 1H, J=6.2 Hz), 9.91 (s, 1H).

[Chemical Formula 47]

Compound Ia-16

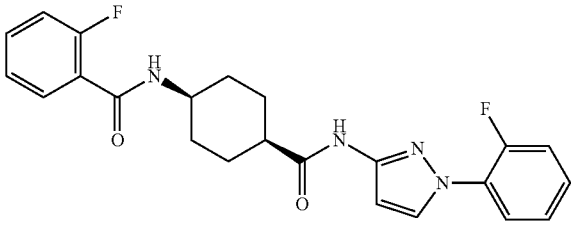

$^1$H-NMR (DMSO-$d_6$) δ: 1.63-1.93 (m, 8H), 2.52-2.54 (m, 1H), 3.99-4.07 (m, 1H), 6.87 (d, 1H, J=2.4 Hz), 7.25-7.59 (m, 7H), 7.73-7.79 (m, 1H), 8.10-8.12 (m, 1H), 8.28-8.30 (m, 1H), 10.62 (s, 1H).

[Chemical Formula 48]

Compound Ia-17

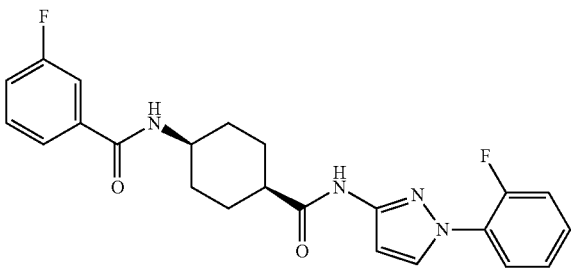

$^1$H-NMR (DMSO-$d_6$) δ: 1.61-2.07 (m, 8H), 2.56-2.64 (m, 1H), 3.99-4.07 (m, 1H), 6.89 (d, 1H, J=2.4 Hz), 7.36-7.80 (m, 8H), 8.11-8.13 (m, 1H), 8.32-8.34 (m, 1H), 10.64 (s, 1H).

[Chemical Formula 49]

Compound Ia-18

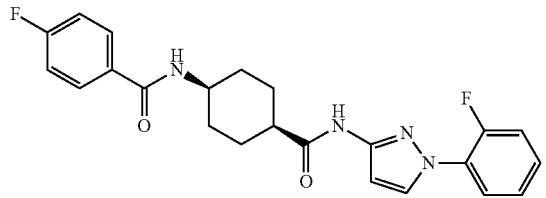

$^1$H-NMR (DMSO-$d_6$) δ: 1.61-2.06 (m, 8H), 2.56-2.64 (m, 1H), 3.95-4.04 (m, 1H), 6.89 (d, 1H, J=2.4 Hz), 7.27-7.51 (m, 5H), 7.74-7.98 (m, 3H), 8.11-8.13 (m, 1H), 8.24-8.27 (m, 1H), 10.64 (s, 1H).

[Chemical Formula 50]

Compound Ia-19

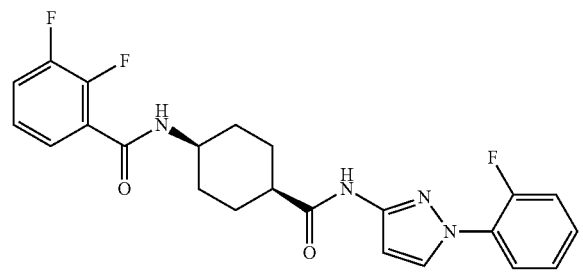

$^1$H-NMR (DMSO-$d_6$) δ: 1.59-1.97 (m, 8H), 2.53-2.58 (m, 1H), 4.01-4.07 (m, 1H), 6.87 (d, 1H, J=2.4 Hz), 7.28-7.56 (m, 6H), 7.74-7.79 (m, 1H), 8.10-8.11 (m, 1H), 8.46-8.49 (m, 1H), 10.63 (s, 1H).

[Chemical Formula 51]

Compound Ia-20

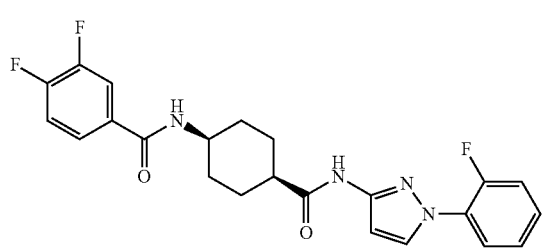

$^1$H-NMR (DMSO-$d_6$) δ: 1.59-2.07 (m, 8H), 2.57-2.64 (m, 1H), 3.94-4.00 (m, 1H), 6.88 (d, 1H, J=2.4 Hz), 7.37-7.79 (m, 6H), 7.93-8.00 (m, 1H), 8.11-8.12 (m, 1H), 8.32-8.34 (m, 1H), 10.64 (s, 1H).

[Chemical Formula 52]

Compound Ia-21

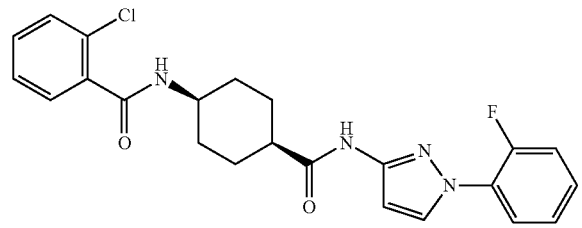

¹H-NMR (DMSO-d₆) δ: 1.57-1.96 (m, 8H), 2.49-2.56 (m, 1H), 4.00-4.07 (m, 1H), 6.85 (d, 1H, J=2.4 Hz), 7.36-7.52 (m, 7H), 7.73-7.79 (m, 1H), 8.09-8.12 (m, 1H), 8.46-8.48 (m, 1H), 10.60 (s, 1H).

[Chemical Formula 53]

Compound Ia-22

¹H-NMR (DMSO-d₆) δ: 1.59-2.06 (m, 8H), 2.53-2.64 (m, 1H), 3.94-4.02 (m, 1H), 6.88 (d, 1H, J=2.4 Hz), 7.37-7.94 (m, 8H), 8.10-8.13 (m, 1H), 8.36-8.38 (m, 1H), 10.64 (s, 1H).

[Chemical Formula 54]

Compound Ia-23

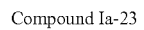

¹H-NMR (DMSO-d₆) δ: 1.59-2.06 (m, 8H), 2.53-2.64 (m, 1H), 3.94-4.03 (m, 1H), 6.88 (d, 1H, J=2.4 Hz), 7.37-7.92 (m, 8H), 8.11-8.13 (m, 1H), 8.30-8.33 (m, 1H), 10.63 (s, 1H).

[Chemical Formula 55]

Compound Ia-24

¹H-NMR (DMSO-d₆) δ: 1.62-2.03 (m, 8H), 2.54-2.61 (m, 1H), 4.02-4.09 (m, 1H), 6.87 (d, 1H, J=2.4 Hz), 7.37-7.79 (m, 7H), 7.91-8.94 (m, 1H), 8.10-8.12 (m, 1H), 8.66-8.68 (m, 1H), 10.63 (s, 1H).

[Chemical Formula 56]

Compound Ia-25

¹H-NMR (DMSO-d₆) δ: 1.64-1.91 (m, 8H), 2.57-2.63 (m, 1H), 4.05-4.10 (m, 1H), 6.90 (d, 1H, J=2.4 Hz), 7.35-7.52 (m, 3H), 7.75-8.13 (m, 3H), 8.36-8.37 (m, 1H), 9.22-9.23 (m, 1H), 10.69 (s, 1H).

[Chemical Formula 57]

Compound Ia-26

¹H-NMR (DMSO-d₆) δ: 1.60-1.94 (m, 8H), 2.56-2.61 (m, 1H), 3.97-4.07 (m, 1H), 6.88 (d, 1H, J=2.4 Hz), 7.34-7.52 (m, 3H), 7.74-7.80 (m, 2H), 8.11-8.12 (m, 1H), 8.53-8.54 (m, 1H), 8.66-8.67 (m, 1H), 10.65 (s, 1H).

[Chemical Formula 58]

Compound Ia-27

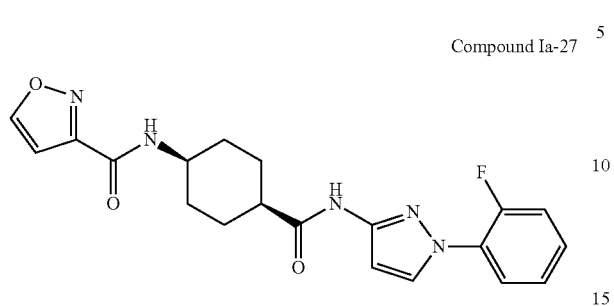

¹H-NMR (DMSO-d₆) δ: 1.61-2.02 (m, 8H), 2.53-2.62 (m, 1H), 3.96-4.04 (m, 1H), 6.88-6.93 (m, 2H), 7.37-7.49 (m, 3H), 7.74-7.80 (m, 1H), 8.12 (s, 1H), 8.52-8.55 (m, 1H), 9.09 (s, 1H), 10.63 (s, 1H).

[Chemical Formula 59]

Compound Ia-28

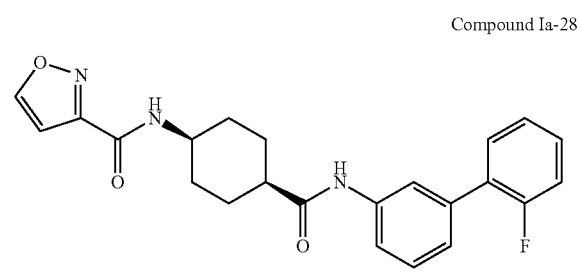

¹H-NMR (DMSO-d₆) δ: 1.62-2.03 (m, 8H), 2.54-2.58 (m, 1H), 3.96-4.04 (m, 1H), 6.92 (d, 1H, J=2.4 Hz), 7.21-7.68 (m, 7H), 7.89 (s, 1H), 8.53-8.55 (m, 1H), 9.07-9.08 (m, 1H), 9.93 (s, 1H).

[Chemical Formula 60]

Compound Ia-29

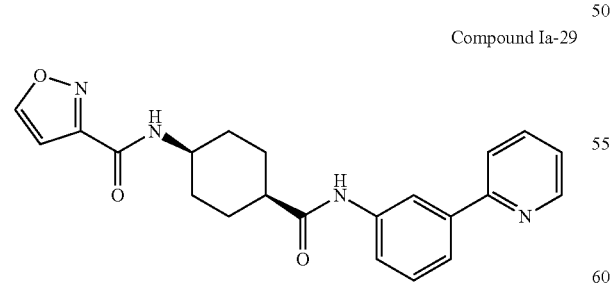

¹H-NMR (DMSO-d₆) δ: 1.64-2.05 (m, 8H), 2.54-2.60 (m, 1H), 3.96-4.07 (m, 1H), 6.93 (d, 1H, J=2.4 Hz), 7.37-7.46 (m, 2H), 7.72-7.76 (m, 2H), 7.91-7.92 (m, 1H), 8.42-8.70 (m, 3H), 9.08-9.09 (m, 1H), 9.95 (s, 1H).

[Chemical Formula 61]

Compound Ia-30

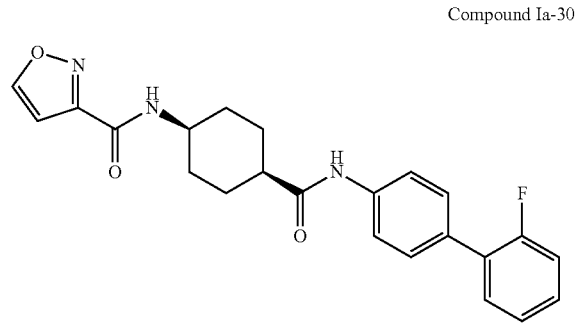

¹H-NMR (DMSO-d₆) δ: 1.63-2.04 (m, 8H), 2.53-2.59 (m, 1H), 3.97-4.07 (m, 1H), 6.93 (d, 1H, J=2.4 Hz), 7.28-7.77 (m, 8H), 8.54-8.57 (m, 1H), 9.08-9.09 (m, 1H), 9.95 (s, 1H).

[Chemical Formula 62]

Compound Ia-31

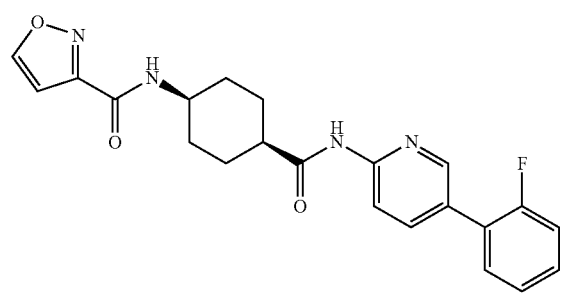

¹H-NMR (DMSO-d₆) δ: 1.61-2.02 (m, 8H), 2.65-2.72 (m, 1H), 3.97-4.06 (m, 1H), 6.93 (d, 1H, J=2.4 Hz), 7.33-7.65 (m, 4H), 8.00-8.03 (m, 1H), 8.22-8.25 (m, 1H), 8.53-8.56 (m, 2H), 9.08-9.09 (m, 1H), 10.52 (s, 1H).

[Chemical Formula 63]

Compound Ia-32

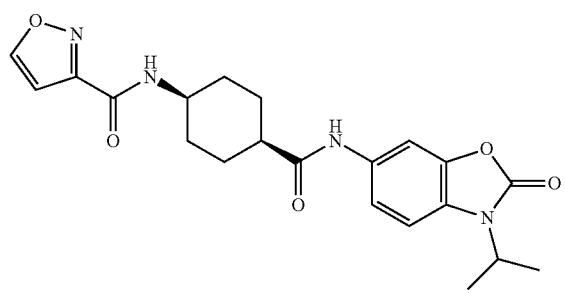

¹H-NMR (DMSO-d₆) δ: 1.47 (d, 6H, J=6.9 Hz), 1.61-1.99 (m, 8H), 2.48-2.53 (m, 1H), 4.00-4.04 (m, 1H), 4.47 (qq, 1H, J=6.9 Hz), 6.92 (d, 1H, J=2.4 Hz), 7.30-7.38 (m, 2H), 7.78-7.79 (m, 1H), 8.52-8.54 (m, 1H), 9.08-9.09 (m, 1H), 9.90 (s, 1H).

[Chemcial Formula 64]

Compound Ia-33

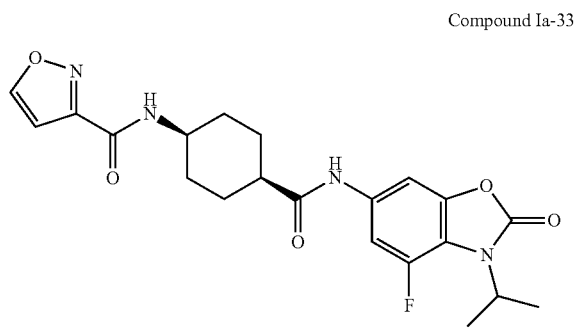

¹H-NMR (DMSO-d₆) δ: 1.45 (d, 6H, J=6.9 Hz), 1.63-2.00 (m, 8H), 2.52-2.54 (m, 1H), 3.95-4.03 (m, 1H), 4.56 (qq, 1H, J=6.9 Hz), 6.92 (d, 1H, J=2.4 Hz), 7.43-7.55 (m, 2H), 8.52-8.55 (m, 1H), 9.07-9.08 (m, 1H), 10.07 (s, 1H).

[Chemical Formula 65]

Compound Ia-34

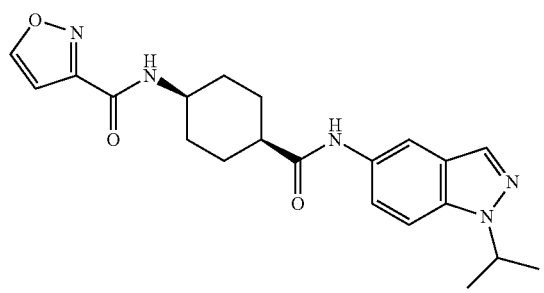

¹H-NMR (DMSO-d₆) δ: 1.49 (d, 6H, J=6.9 Hz), 1.62-2.05 (m, 8H), 2.52-2.54 (m, 1H), 3.97-4.05 (m, 1H), 4.95 (qq, 1H, J=6.9 Hz), 6.93 (d, 1H, J=2.4 Hz), 7.46-7.65 (m, 2H), 8.01-8.13 (m, 2H), 8.53-8.55 (m, 1H), 9.08-9.09 (m, 1H), 9.80 (s, 1H).

[Chemical Formula 66]

Compound Ia-35

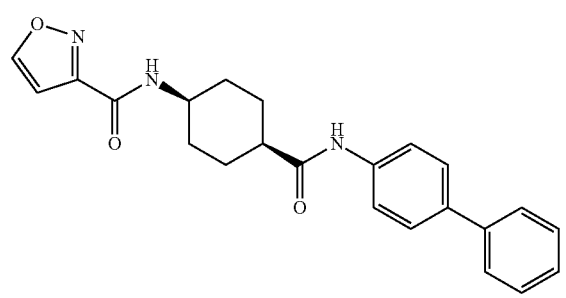

¹H-NMR (DMSO-d₆) δ: 1.63-2.04 (m, 8H), 2.53-2.59 (m, 1H), 3.96-4.06 (m, 1H), 6.93 (d, 1H, J=2.4 Hz), 7.32-7.76 (m, 9H), 8.54-8.56 (m, 1H), 9.08-9.09 (m, 1H), 9.91 (s, 1H).

[Chemical Formula 67]

Compound Ia-36

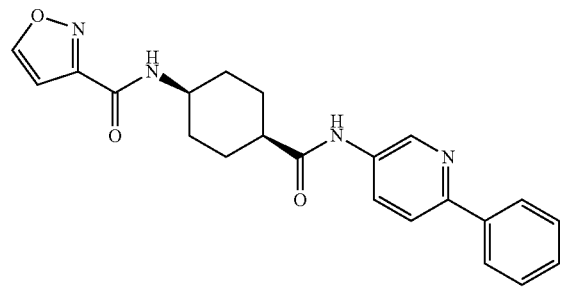

¹H-NMR (DMSO-d₆) δ: 1.64-2.05 (m, 8H), 2.55-2.63 (m, 1H), 3.96-4.06 (m, 1H), 6.93 (d, 1H, J=2.4 Hz), 7.39-7.52 (m, 3H), 7.94-8.21 (m, 4H), 8.55-8.57 (m, 1H), 8.87-8.88 (m, 1H), 9.08-9.09 (m, 1H), 10.13 (s, 1H).

[Chemical Formula 68]

Compound Ia-38

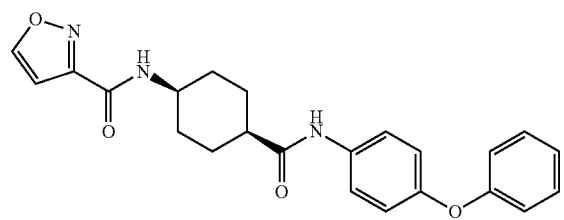

¹H-NMR (DMSO-d₆) δ: 1.62-2.01 (m, 8H), 2.48-2.53 (m, 1H), 3.96-4.04 (m, 1H), 6.92-7.14 (m, 6H), 7.36-7.41 (m, 2H), 7.64-7.67 (m, 2H), 8.52-8.55 (m, 1H), 9.08-9.09 (m, 1H), 9.83 (s, 1H).

[Chemical Formula 69]

Compound Ia-39

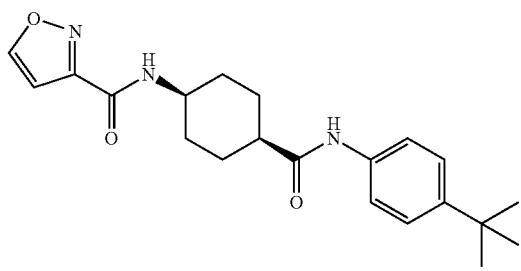

¹H-NMR (DMSO-d₆) δ: 1.28 (s, 9H), 1.62-2.02 (m, 8H), 2.47-2.54 (m, 1H), 3.98-4.05 (m, 1H), 6.93 (d, 1H, J=2.4 Hz), 7.33 (d, 2H, J=8.4 Hz), 7.56 (d, 2H, J=8.4 Hz), 8.52-8.54 (m, 1H), 9.08-9.09 (m, 1H), 9.72 (s, 1H).

[Chemical Formula 70]

Compound Ia-40

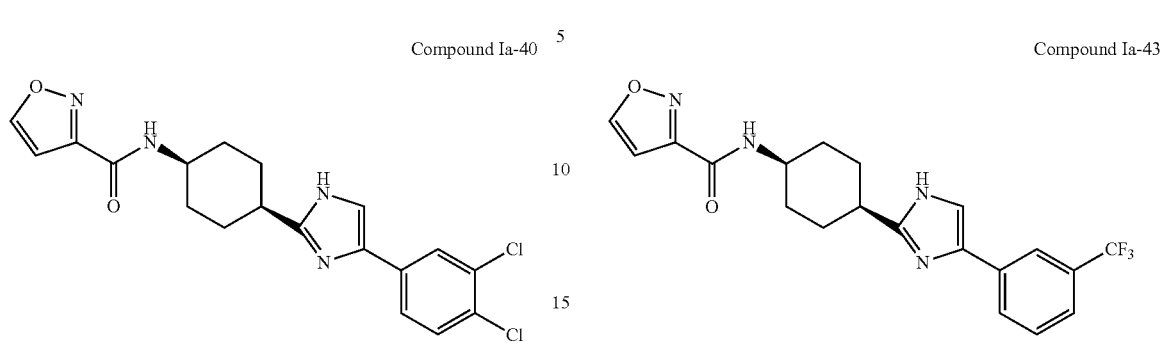

$^{1}$H-NMR (DMSO-d$_6$) δ: 1.61-2.26 (m, 8H), 2.87-2.96 (m, 1H), 3.92-4.06 (m, 1H), 6.89 (d, 1H, J=1.5 Hz), 7.54-7.77 (m, 3H), 7.98 (s, 1H), 8.45-8.88 (m, 1H), 9.03-9.04 (m, 1H), 11.94 (s, 1H).

[Chemical Formula 71]

Compound Ia-41

$^{1}$H-NMR (DMSO-d$_6$) δ: 1.66-1.85 (m, 6H), 2.16-2.24 (m, 2H), 2.89-2.97 (m, 1H), 3.95-4.04 (m, 1H), 6.90 (d, 1H, J=1.5 Hz), 7.39 (d, 2H, J=8.1 Hz), 7.59-7.60 (m, 1H), 7.81 (d, 2H, J=8.1 Hz), 8.47-8.50 (m, 1H), 9.05-9.06 (m, 1H), 11.85 (s, 1H).

[Chemical Formula 72]

Compound Ia-42

$^{1}$H-NMR (DMSO-d$_6$) δ: 1.66-1.85 (m, 6H), 2.14-2.25 (m, 2H), 2.90-2.97 (m, 1H), 3.95-4.05 (m, 1H), 6.91 (d, 1H, J=1.5 Hz), 7.19-7.39 (m, 2H), 7.67-7.84 (m, 3H), 8.48-8.50 (m, 1H), 9.05-9.06 (m, 1H), 11.90 (s, 1H).

[Chemical Formula 73]

Compound Ia-43

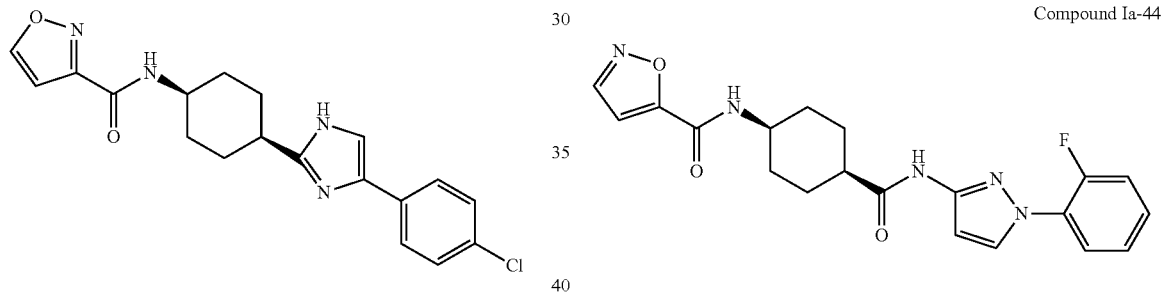

$^{1}$H-NMR (DMSO-d$_6$) δ: 1.69-1.89 (m, 6H), 2.16-2.28 (m, 2H), 2.92-3.00 (m, 1H), 3.98-4.10 (m, 1H), 6.92 (d, 1H, J=1.5 Hz), 7.51-7.76 (m, 3H), 8.07-8.11 (m, 2H), 8.49-8.51 (m, 1H), 9.06-9.07 (m, 1H), 11.98 (s, 1H).

[Chemical Formula 74]

Compound Ia-44

$^{1}$H-NMR (DMSO-d$_6$) δ: 1.59-2.07 (m, 8H), 2.58-2.65 (m, 1H), 3.91-4.02 (m, 1H), 6.88 (d, 1H, J=2.4 Hz), 7.13-7.14 (m, 1H), 7.34-7.51 (m, 3H), 7.74-7.79 (m, 1H), 8.10-8.13 (m, 1H), 8.70-8.74 (m, 2H), 10.64 (s, 1H).

[Chemical Formula 75]

Compound Ia-45

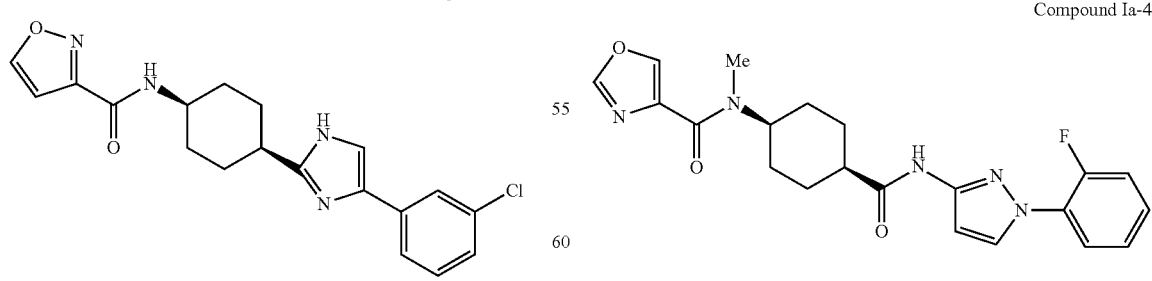

$^{1}$H-NMR (DMSO-d$_6$) δ: 1.41-2.17 (m, 8H), 2.68 (br, 1H×⅔), 2.77 (br, 1H×⅓), 2.89 (s, 3H×⅓), 2.91 (s, 3H×⅔), 3.58-3.69 (m, 1H×⅔), 4.39-4.49 (m, 1H×⅓), 6.82-6.90 (m, 2H), 7.37-7.52 (m, 3H), 7.74-7.80 (m, 1H), 8.11-8.12 (m, 1H), 9.08-9.11 (m, 1H), 10.65-10.69 (m, 1H).

[Chemical Formula 76]

Compound Ia-46

¹H-NMR (DMSO-d₆) δ: 1.59-2.03 (m, 8H), 2.56-2.62 (m, 1H), 2.64 (s, 3H), 3.90-3.97 (m, 1H), 6.88 (d, 1H, J=2.4 Hz), 7.34-7.52 (m, 3H), 7.73-7.79 (m, 1H), 8.04-8.12 (m, 2H), 9.00 (s, 1H), 10.65 (s, 1H).

[Chemical Formula 77]

Compound Ia-47

¹H-NMR (DMSO-d₆) δ: 1.61-1.95 (m, 8H), 2.55-2.62 (m, 1H), 3.97-4.06 (m, 1H), 7.21-7.90 (m, 9H), 8.54 (s, 1H), 8.67 (s, 1H), 9.95 (s, 1H).

[Chemical Formula 78]

Compound Ib-1

¹H-NMR (DMSO-d₆) δ: 1.53-1.67 (m, 4H), 1.72-1.94 (m, 4H), 2.48-2.51 (m, 1H), 6.00-6.04 (m, 1H), 6.39-6.47 (m, 1H), 6.79-6.88 (m, 1H), 7.28-7.50 (m, 5H), 7.67-7.77 (m, 1H), 8.01-8.09 (m, 1H), 10.60 (s, 1H).

[Chemical Formula 79]

Compound Ib-2

¹H-NMR (DMSO-d₆) δ: 1.56-1.68 (m, 4H), 1.77-1.93 (m, 4H), 2.39-2.48 (m, 1H), 3.86-4.02 (m, 1H), 6.04 (d, 1H, J=6.0 Hz), 6.45 (d, 1H, J=7.2 Hz), 6.92-6.95 (m, 1H), 7.09-7.12 (m, 1H), 7.13 (t, 1H, J=74.4 Hz), 7.41-7.49 (m, 1H), 7.65 (d, 2H, J=8.8 Hz), 9.90 (s, 1H).

[Chemical Formula 80]

Compound Ib-3

¹H-NMR (DMSO-d₆) δ: 1.13-1.28 (m, 2H), 1.46-1.62 (m, 2H), 1.80-2.06 (m, 4H), 2.35-2.50 (m, 1H), 3.49-3.58 (m, 1H), 6.00-6.07 (m, 1H), 6.28-6.32 (m, 1H), 6.77-6.89 (m, 2H), 7.29-7.51 (m, 4H), 7.68-7.77 (m, 1H), 8.05-8.12 (m, 1H), 10.65 (s, 1H).

[Chemical Formula 81]

Compound Ib-4

¹H-NMR (DMSO-d₆) δ: 1.44 (d, 6H, J=6.8 Hz), 1.56-1.68 (m, 4H), 1.77-1.92 (m, 4H), 2.38-2.46 (m, 1H), 3.85-3.92 (m, 1H), 4.40-4.49 (m, 1H), 6.02 (d, 1H, J=6.4 Hz), 6.45 (d, 1H, J=6.4 Hz), 6.93 (d, 1H, J=7.2 Hz), 7.27-7.35 (m, 2H), 7.41-7.49 (m, 1H), 7.74 (s, 1H), 9.92 (s, 1H).

[Chemical Formula 82]

Compound Ib-5

¹H-NMR (DMSO-d₆) δ: 1.14 (d, 6H, J=6.0 Hz), 1.56-1.65 (m, 4H), 1.77-1.90 (m, 4H), 2.17 (t, 2H, J=11.2 Hz), 2.35-2.42 (m, 1H), 3.48 (d, 2H, J=11.2 Hz), 3.63-3.72 (m, 2H), 3.84-3.91 (m, 1H), 6.03 (d, 1H, J=7.2 Hz), 6.45 (d, 1H, J=7.6 Hz), 6.87 (d, 2H, J=7.6 Hz), 6.90-6.94 (m, 1H), 7.41-7.49 (m, 3H), 9.58 (s, 1H).

[Chemical Formula 83]

Compound Ib-6

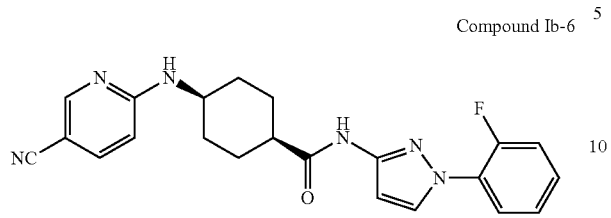

¹H-NMR (DMSO-d₆) δ: 1.61-1.71 (m, 4H), 1.76-1.98 (m, 4H), 2.51-2.62 (m, 1H), 4.03-4.16 (m, 1H), 6.82-6.85 (m, 1H), 6.96 (d, 1H, J=9.2 Hz), 7.30-7.48 (m, 3H), 7.70-7.88 (m, 2H), 8.07-8.09 (m, 1H), 8.45-8.69 (m, 2H), 10.67 (s, 1H).

[Chemcial Formula 84]

Compound Ib-7

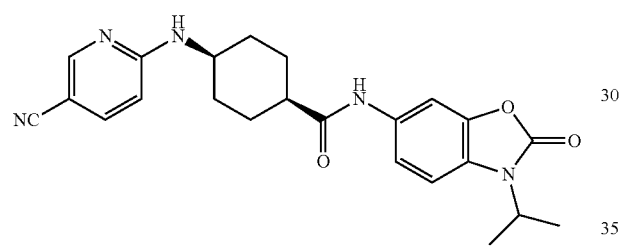

¹H-NMR (DMSO-d₆) δ: 1.47 (d, 6H, J=6.8 Hz), 1.61-1.69 (m, 4H), 1.78-1.92 (m, 4H), 2.40-2.48 (m, 1H), 4.02-4.14 (m, 1H), 4.41-4.48 (m, 1H), 6.67 (d, 1H, J=8.8 Hz), 7.26-7.36 (m, 2H), 7.58 (d, 1H, J=7.2 Hz), 7.63 (d, 1H, J=8.4 Hz), 7.77 (brs, 1H), 8.36-8.38 (m, 1H), 9.93 (s, 1H).

[Chemical Formula 85]

Compound Ic-1

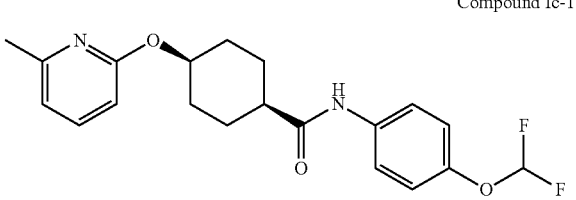

¹H-NMR (DMSO-d₆) δ: 1.34-1.48 (m, 2H), 1.55-1.67 (m, 2H), 1.88-1.96 (m, 2H), 2.13-2.19 (m, 2H), 2.34-2.44 (m, 1H), 2.37 (s, 3H), 4.92-5.01 (m, 1H), 6.53 (d, 1H, J=8.0 Hz), 6.78 (d, 1H, J=7.2 Hz), 7.11 (t, 1H, J=74.4 Hz), 7.12-7.15 (m, 2H), 7.55 (t, 1H, J=7.6 Hz), 7.64 (d, 2H, J=8.8 Hz), 9.97 (s, 1H).

[Chemical Formula 86]

Compound Ic-2

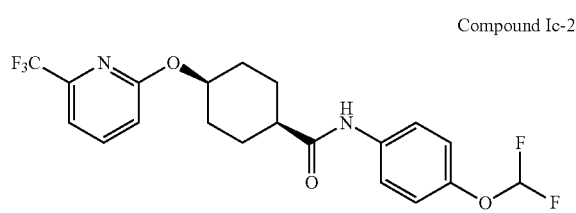

¹H-NMR (DMSO-d₆) δ: 1.39-1.54 (m, 2H), 1.57-1.69 (m, 2H), 1.91-1.99 (m, 2H), 2.16-2.24 (m, 2H), 2.34-2.43 (m, 1H), 4.91-5.00 (m, 1H), 7.12 (t, 1H, J=74.4 Hz), 7.11-7.16 (m, 3H), 7.45 (d, 1H, J=5.6 Hz), 7.65 (d, 2H, J=7.6 Hz), 7.92-7.98 (m, 1H), 9.97 (s, 1H).

[Chemical Formula 87]

Compound Ic-4

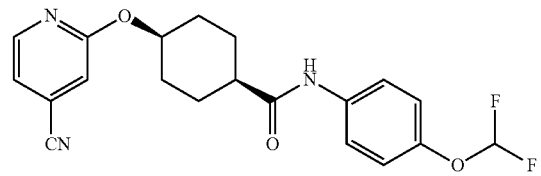

¹H-NMR (DMSO-d₆) δ: 1.61-1.73 (m, 4H), 1.76-1.90 (m, 2H), 1.97-2.08 (m, 2H), 2.46 (m, 1H), 5.27 (s, 1H), 7.11 (d, 2H, J=8.8 Hz), 7.12 (t, 1H, J=74.4 Hz), 7.36 (d, 1H, J=4.8 Hz), 7.64 (d, 2H, J=8.8 Hz), 8.38 (d, 1H, J=4.8 Hz), 9.93 (s, 1H).

[Chemical Formula 88]

Compound Ic-5

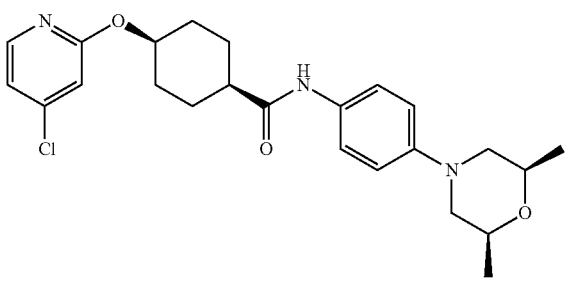

¹H-NMR (DMSO-d₆) δ: 1.14 (d, 6H, J=6.0 Hz), 1.59-1.72 (m, 4H), 1.75-1.89 (m, 2H), 1.97-2.05 (m, 2H), 2.18 (dd, 2H, J=11.2, 11.2 Hz), 2.41 (m, 1H), 3.48 (d, 2H, J=11.2 Hz), 3.63-3.72 (m, 2H), 5.24 (s, 1H), 6.87 (d, 2H, J=8.8 Hz), 6.96 (s, 1H), 7.06 (d, 1H, J=5.6 Hz), 7.45 (d, 2H, J=8.8 Hz), 8.14 (d, 1H, J=5.6 Hz), 9.60 (s, 1H).

[Chemical Formula 89]

Compound Ic-6

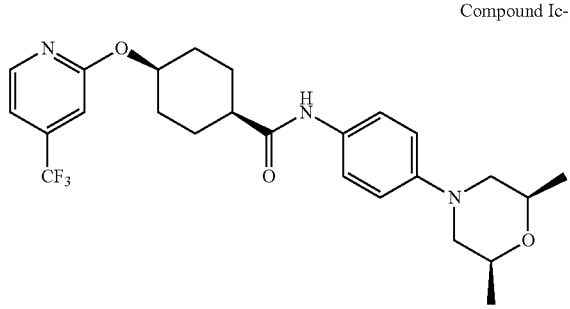

¹H-NMR (DMSO-d₆) δ: 1.14 (d, 6H, J=6.0 Hz), 1.62-1.72 (m, 4H), 1.79-1.91 (m, 2H), 2.00-2.08 (m, 2H), 2.18 (dd, 2H, J=11.2, 11.2 Hz), 2.42 (m, 1H), 3.48 (d, 2H, J=11.2 Hz), 3.63-3.72 (m, 2H), 5.31 (s, 1H), 6.87 (d, 2H, J=8.8 Hz), 7.13 (s, 1H), 7.28 (d, 1H, J=5.2 Hz), 7.46 (d, 2H, J=8.8 Hz), 8.42 (d, 1H, J=5.2 Hz), 9.65 (s, 1H).

[Chemical Formula 90]

Compound Ic-7

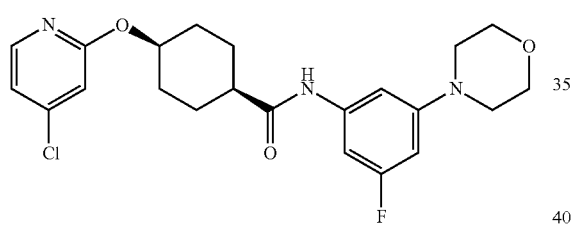

¹H-NMR (DMSO-d₆) δ: 1.59-1.71 (m, 4H), 1.73-1.88 (m, 2H), 1.94-2.05 (m, 2H), 2.42 (m, 1H), 3.03-3.12 (m, 4H), 3.69-3.73 (m, 4H), 5.24 (s, 1H), 6.46 (d, 1H, J=12.4 Hz), 6.93-7.03 (m, 3H), 7.06 (d, 1H, J=5.6 Hz), 8.14 (d, 1H, J=5.6 Hz), 9.88 (s, 1H).

[Chemical Formula 91]

Compound Ic-8

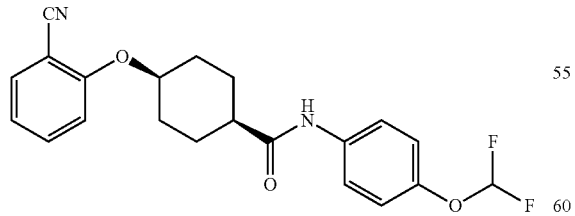

¹H-NMR (DMSO-d₆) δ: 1.62-1.75 (m, 4H), 1.80-1.92 (m, 2H), 1.98-2.08 (m, 2H), 2.46 (m, 1H), 4.83 (s, 1H), 7.07 (dd, 1H, J=7.6, 7.6 Hz), 7.12 (d, 2H, J=8.8 Hz), 7.13 (t, 1H, J=74.4 Hz), 7.27 (d, 1H, J=7.6 Hz), 7.64 (m, 1H), 7.65 (d, 2H, J=8.8 Hz), 7.72 (d, 1H, J=7.6 Hz), 9.92 (s, 1H).

[Chemical Formula 92]

Compound Ic-9

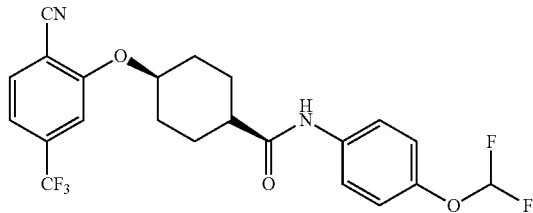

¹H-NMR (DMSO-d₆) δ: 1.65-1.78 (m, 4H), 1.79-1.93 (m, 2H), 1.99-2.09 (m, 2H), 2.47 (m, 1H), 5.04 (s, 1H), 7.12 (d, 2H, J=8.8 Hz), 7.13 (t, 1H, J=74.4 Hz), 7.44 (d, 1H, J=8.0 Hz), 7.61 (s, 1H), 7.65 (d, 2H, J=8.8 Hz), 8.00 (d, 1H, J=8.0 Hz), 9.93 (s, 1H).

[Chemical Formula 93]

Compound Ic-10

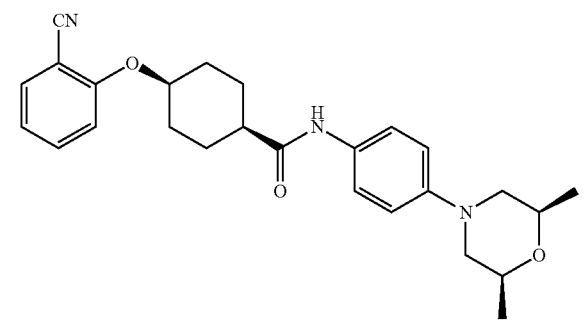

¹H-NMR (DMSO-d₆) δ: 1.14 (d, 6H, J=6.0 Hz), 1.67 (bs, 3H), 1.79-1.92 (m, 2H), 2.00-2.04 (m, 2H), 2.17 (t, 2H, J=16.5 Hz), 2.41 (t, 1H, J=11.1 Hz), 3.49 (d, 1H, J=11.4 Hz), 3.66-3.70 (m, 1H), 6.87 (d, 2H, J=8.7 Hz), 7.07 (t, 1H, J=7.5 Hz), 7.27 (d, 1H, J=8.4 Hz), 7.46 (d, 2H, J=9.0 Hz), 7.64 (t, 1H, J=9.0 Hz), 7.72 (d, 1H, J=7.5 Hz), 9.59 (s, 1H).

[Chemical Formula 94]

Compound Ic-11

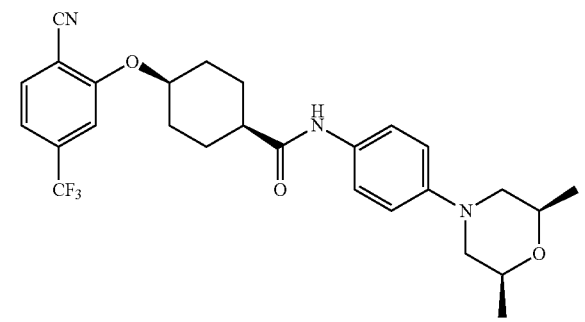

¹H-NMR (DMSO-d₆) δ: 1.13 (d, 6H, J=6.3 Hz), 1.67 (brs, 3H), 1.77-1.85 (m, 2H), 2.02 (d, 2H, J=8.1 Hz), 2.17 (t, 2H, J=10.8 Hz), 2.37 (t, 1H, J=10.8 Hz), 3.48 (d, 2H, J=10.8 Hz), 3.66-3.70 (m, 2H), 4.81 (brs, 1H), 6.87 (d, 2H, J=9.3 Hz), 7.31 (d, 1H, J=9.3 Hz), 7.46 (d, 2H, J=9.0 Hz), 7.69 (dd, 1H, J=9.0, 2.4 Hz), 7.91 (d, 1H, J=3.0 Hz), 9.59 (s, 1H).

[Chemical Formula 95]

Compound Ic-12

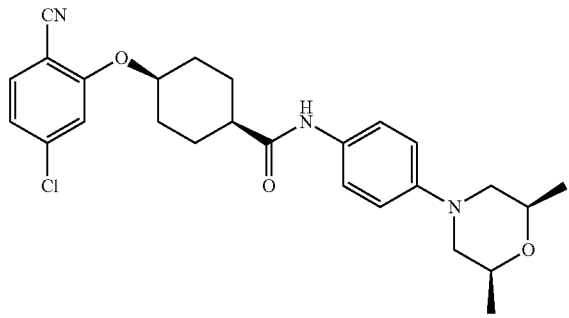

¹H-NMR (DMSO-d₆) δ: 1.14 (d, 6H, J=6.3 Hz), 1.69 (brs, 3H), 1.85-1.86 (m, 2H), 1.99-2.04 (m, 2H), 2.18 (t, 2H, J=11.1 Hz), 2.42 (t, 1H, J=9.9 Hz), 3.49 (d, 2H, J=10.5 Hz), 3.66-3.71 (m, 2H), 5.03 (brs, 1H), 6.87 (d, 2H, J=9.0 Hz), 7.42-7.47 (m, 3H), 7.60 (s, 1H), 8.00 (d, 1H, J=8.1 Hz), 9.06 (s, 1H).

[Chemical Formula 96]

Compound Ic-13

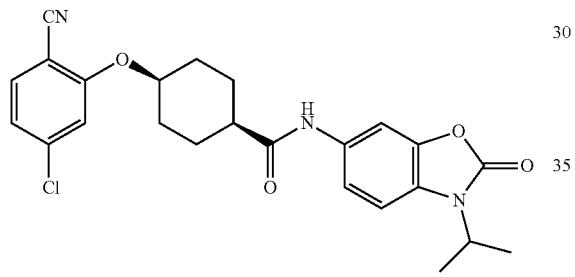

¹H-NMR (CDCl₃) δ: 1.52 (d, 6H, J=7.0 Hz), 1.62-1.75 (m, 2H), 1.88-2.00 (m, 2H), 2.01-2.09 (m, 2H), 2.13-2.24 (m, 2H), 2.49 (m, 1H), 4.52 (m, 1H), 4.78 (m, 1H), 6.98-7.05 (m, 3H), 7.27 (dd, 1H, J=2.0, 8.5 Hz), 7.50 (d, 1H, J=8.5 Hz), 7.55 (brs, 1H), 7.67 (d, 1H, J=2.0 Hz).

[Chemical Formula 97]

Compound Ic-14

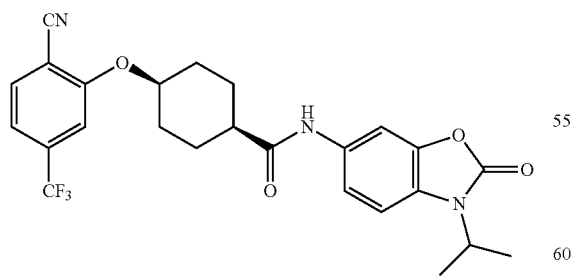

¹H-NMR (DMSO-d₆) δ: 1.44 (d, 6H, J=6.9 Hz), 1.64-1.76 (m, 4H), 1.77-1.92 (m, 2H), 1.97-2.08 (m, 2H), 2.46 (m, 1H), 4.44 (m, 1H), 5.03 (m, 1H), 7.26-7.35 (m, 2H), 7.43 (m, 1H), 7.60 (brs, 1H), 7.75 (d, 1H, J=1.8 Hz), 7.99 (m, 1H), 9.94 (s, 1H).

[Chemical Formula 98]

Compound Ic-15

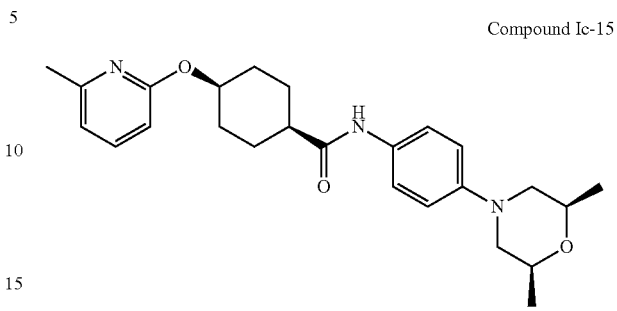

¹H-NMR (DMSO-d₆) δ: 1.14 (d, 6H, J=6.0 Hz), 1.32-1.48 (m, 2H), 1.51-1.66 (m, 2H), 1.85-1.94 (m, 2H), 2.11-2.22 (m, 3H), 2.35-2.41 (m, 1H), 2.37 (s, 3H), 3.45-3.51 (m, 2H), 3.61-3.77 (m, 2H), 4.91-5.00 (m, 2H), 6.51-6.56 (m, 1H), 6.76-6.82 (m, 1H), 6.84-6.92 (m, 2H), 7.42-7.49 (m, 2H), 7.52-7.60 (m, 1H), 9.65 (s, 1H).

[Chemical Formula 99]

Compound Ic-16

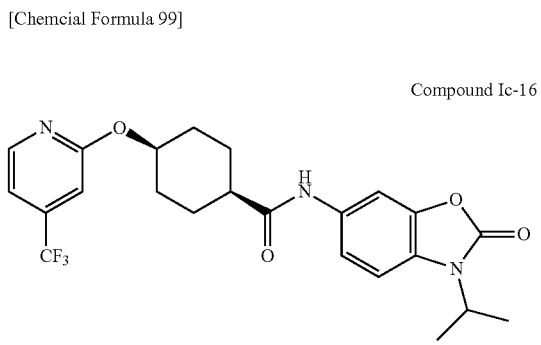

¹H-NMR (DMSO-d₆) δ: 1.44 (d, 6H, J=6.7 Hz), 1.61-1.72 (m, 4H), 1.74-1.91 (m, 2H), 1.96-2.06 (m, 2H), 2.44 (m, 1H), 4.44 (m, 1H), 5.24 (m, 1H), 6.97 (dd, 1H, J=0.5, 1.8 Hz), 7.07 (dd, 1H, J=1.8, 5.5 Hz), 7.26-7.35 (m, 2H), 7.75 (d, 1H, J=1.7 Hz), 8.13 (dd, 1H, J=0.5, 5.5 Hz), 9.96 (s, 1H).

[Chemical Formula 100]

Compound Ic-17

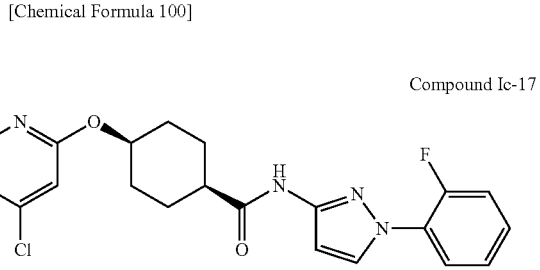

¹H-NMR (DMSO-d₆) δ: 1.57-1.72 (m, 4H), 1.74-1.91 (m, 2H), 1.94-2.06 (m, 2H), 2.52 (m, 1H), 5.23 (m, 1H), 6.83 (d, 1H, J=2.6 Hz), 6.97 (d, 1H, J=1.7 Hz), 7.07 (dd, 1H, J=1.8, 5.5 Hz), 7.29-7.50 (m, 3H), 7.69-7.76 (m, 1H), 8.08 (t, 1H, J=2.6 Hz), 8.13 (d, 1H, J=5.5 Hz), 10.66 (s, 1H).

[Chemical Formula 101]

Compound Ic-18

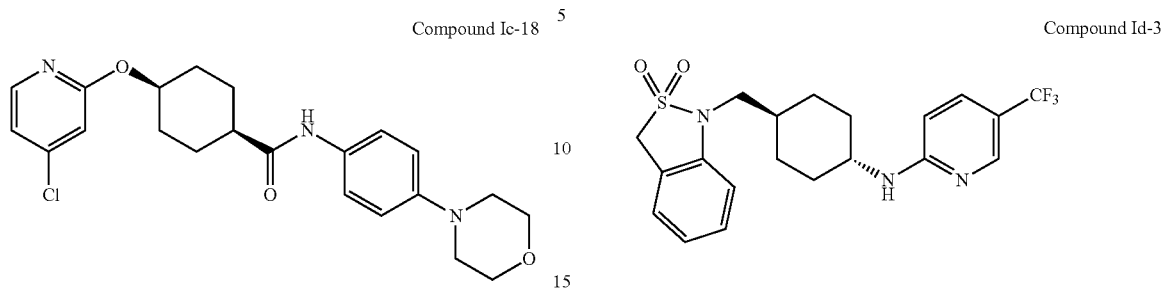

¹H-NMR (DMSO-d₆) δ: 1.58-1.70 (m, 4H), 1.75-1.88 (m, 2H), 1.96-2.05 (m, 2H), 2.41 (m, 1H), 2.98-3.05 (m, 4H), 3.70-3.74 (m, 4H), 5.24 (s, 1H), 6.87 (d, 2H, J=8.8 Hz), 6.97 (s, 1H), 7.06 (d, 1H, J=5.6 Hz), 7.46 (d, 2H, J=8.8 Hz), 8.14 (d, 1H, J=5.6 Hz), 9.66 (s, 1H).

[Chemical Formula 102]

Compound Ic-19

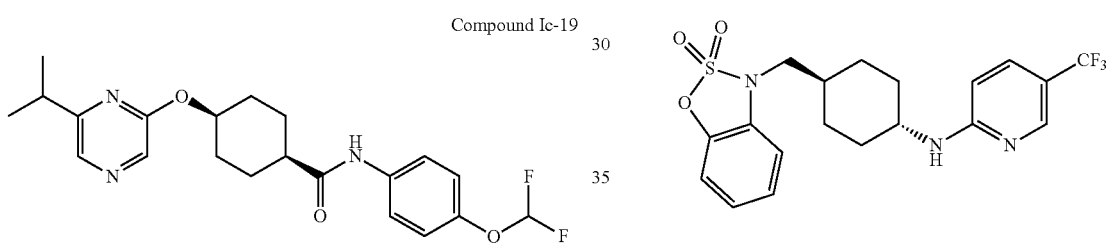

¹H-NMR (DMSO-d₆) δ: 1.23 (d, 6H, J=8.0 Hz), 1.63-1.75 (m, 4H), 1.75-1.91 (m, 2H), 2.00-2.10 (m, 2H), 2.46 (m, 1H), 2.98 (m, 1H), 5.27 (s, 1H), 7.11 (d, 2H, J=8.0 Hz), 7.12 (t, 1H, J=74.4 Hz), 7.63 (s, 1H), 7.66 (s, 1H), 8.09 (d, 1H, J=8.0 Hz), 9.95 (s, 1H).

[Chemical Formula 103]

Compound Id-2

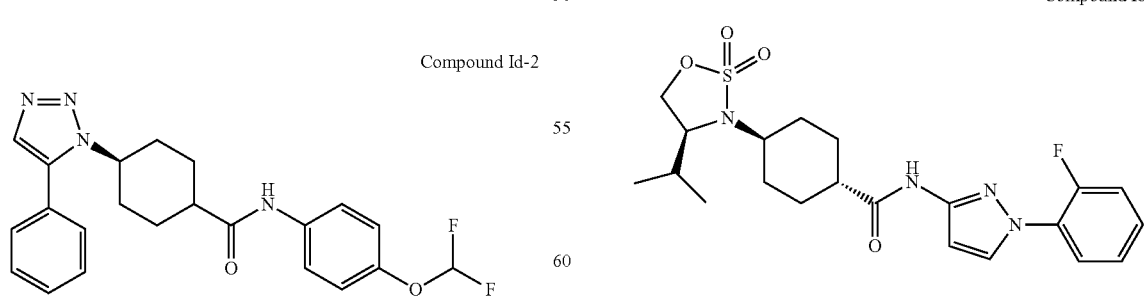

¹H-NMR (DMSO-d₆) δ: 1.51-1.67 (m, 2H), 1.94-2.17 (m, 6H), 2.47 (m, 1H), 4.36 (m, 1H), 6.90 (s, 0.3H), 7.10-7.18 (m, 2.6H), 7.40 (s, 0.3H), 7.52-7.68 (m, 7H), 7.87 (s, 1H), 10.01 (s, 1H).

[Chemical Formula 104]

Compound Id-3

¹H-NMR (DMSO-d₆) δ: 1.13-1.26 (m, 4H), 1.68-1.78 (m, 1H), 1.84-1.92 (m, 2H), 1.97-2.03 (m, 2H), 3.38 (d, 2H, J=7.2 Hz), 3.69-3.80 (m, 1H), 4.65 (s, 2H), 6.54 (d, 1H, J=8.8 Hz), 6.96-7.03 (m, 2H), 7.21 (d, 1H, J=7.6 Hz), 7.30-7.36 (m, 2H), 7.58 (d, 1H, J=8.8 Hz), 8.27 (s, 1H).

[Chemical Formula 105]

Compound Id-4

¹H-NMR (DMSO-d₆) δ: 1.14-1.32 (m, 4H), 1.76-1.94 (m, 3H), 1.95-2.08 (m, 2H), 3.64-3.84 (m, 3H), 6.54 (d, 1H, J=8.7 Hz), 7.06-7.16 (m, 1H), 7.20-7.34 (m, 3H), 7.38 (d, 1H, J=7.8 Hz), 7.59 (dd, 1H, J=9.0, 2.4 Hz), 8.27 (s, 1H).

[Chemical Formula 106]

Compound Id-5

¹H-NMR (DMSO-d₆) δ: 0.93-0.96 (m, 6H), 1.51-2.03 (m, 8H), 2.36-2.44 (m, 1H), 3.24-3.34 (m, 2H), 3.78-3.83 (m, 1H), 4.44-4.53 (m, 2H), 6.84 (d, J=2.4 Hz, 1H), 7.34-7.51 (m, 3H), 7.73-7.79 (m, 1H), 8.10-8.11 (m, 1H), 10.70 (s, 1H).

[Chemical Formula 107]

Compound Id-6

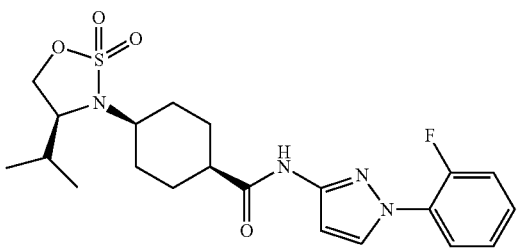

¹H-NMR (DMSO-d₆) δ: 0.90-0.98 (m, 6H), 1.58-2.09 (m, 8H), 2.61-2.68 (m, 1H), 3.31-3.37 (m, 2H), 3.69-3.74 (m, 1H), 4.47-4.49 (m, 2H), 6.86 (d, J=2.4 Hz, 1H), 7.34-7.52 (m, 3H), 7.73-7.79 (m, 1H), 8.10-8.12 (m, 1H), 10.63 (s, 1H).

[Chemical Formula 108]

Compound Id-7

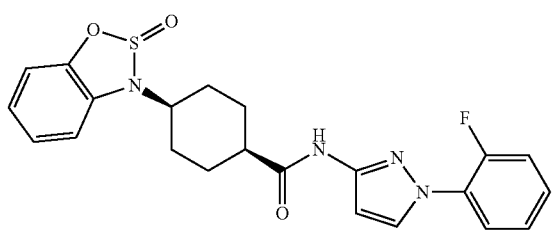

¹H-NMR (DMSO-d₆) δ: 1.70-2.46 (m, 8H), 2.76-2.79 (m, 1H), 4.05-4.14 (m, 1H), 6.89 (d, J=2.4 Hz, 1H), 6.99-7.49 (m, 7H), 7.72-7.78 (m, 1H), 8.09-8.11 (m, 1H), 10.69 (s, 1H).

[Chemical Formula 109]

Compound Id-8

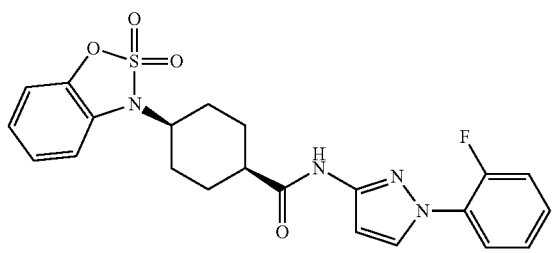

¹H-NMR (DMSO-d₆) δ: 1.72-2.41 (m, 8H), 2.76-2.81 (m, 1H), 4.12-4.20 (m, 1H), 6.90 (d, J=2.4 Hz, 1H), 7.05-7.49 (m, 7H), 7.72-7.78 (m, 1H), 8.11-8.12 (m, 1H), 10.69 (s, 1H).

[Chemical Formula 110]

Compound Id-9

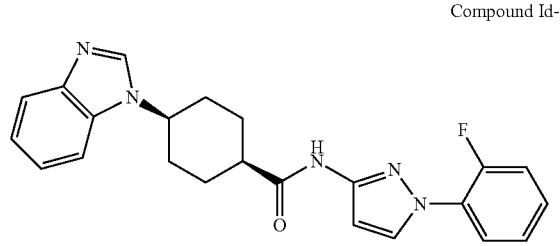

¹H-NMR (DMSO-d₆) δ: 1.80-2.45 (m, 8H), 3.34-3.36 (m, 1H), 4.45-4.55 (m, 1H), 6.94 (d, J=2.4 Hz, 1H), 7.20-7.52 (m, 5H), 7.67-7.81 (m, 3H), 8.13-8.15 (m, 1H), 8.29 (s, 1H), 10.75 (s, 1H).

Test Example 1-1

Affinity for NPY Y5 Receptor cDNA sequence encoding mouse NPY Y5 receptor (Biochem. Biophys. Acta 1328: 83-89, 1997) was cloned in the expression vector (pME18S, Takebe et al. Mol. Cell. Biol. 8, 466-472). The obtained expression vector was transfected into CHO cells as a host according to the instruction manual using Lipofectamine reagent (Trademark, Gibco BRL Co., Ltd.). The cells that stably express NPY Y5 receptor were obtained.

The membrane samples prepared from the CHO cells expressing NPY Y5 receptor, the compound of the invention and 30,000 cpm $^{125}$I peptide YY (60 pM of final concentration: Amersham) were incubated in the assay buffer (20 mM HEPES-Hanks buffer containing 0.1% bovine serum albumin, pH 7.4) at 25° C. for 2 hours. The membrane samples were then filtered from the mixture through a glassfilter (GF/C) presoaked with 1% polyethyleneimine. After washing with 50 mM Tris-HCl buffer (pH 7.4), radioactivity retained on the filters was determined using gamma counter. Non-specific binding was determined in the presence of 200 nM of peptide YY and the 50% inhibitory concentration ($IC_{50}$ value) of the test compound for specific peptide YY binding was calculated (Inui, A. et al. Endocrinology 131, 2090-2096 (1992)). The results are shown in Table 1.

The compounds of the present invention inhibited the binding of peptide YY (homologue of NPY) to NPY Y5 receptor, indicating that the compounds of the present invention have an affinity for the NPY Y5 receptor.

TABLE 1

| Compound No. | Binding $IC_{50}$(nM) |
| --- | --- |
| Ia-2 | 1.6 |
| Ia-4 | 3.8 |
| Ia-14 | 4.1 |
| Ia-15 | 4.5 |
| Ia-24 | 2.9 |
| Ia-28 | 4.1 |
| Ia-30 | 0.71 |
| Ia-32 | 3.3 |
| Ia-35 | 0.65 |
| Ia-40 | 0.26 |
| Ia-42 | 3.0 |
| Ia-43 | 1.8 |
| Ib-1 | 2.9 |
| Ib-4 | 1.5 |
| Ic-5 | 1.5 |
| Ic-8 | 2.3 |
| Ic-11 | 1.8 |
| Ic-12 | 1.1 |
| Ic-13 | 0.56 |
| Ic-14 | 0.68 |
| Ic-16 | 0.41 |
| Ic-17 | 0.69 |
| Id-1 | 3.8 |
| Id-8 | 0.58 |

Test Example 1-2

Affinity for NPY Y5 Receptor cDNA sequence encoding human NPY Y5 receptor (WO96/16542) was cloned in the expression vector (pME18S, Takebe et al. Mol. Cell. Biol. 8, 466-472). The obtained expression vector was transfected into CHO cells as a host according to the instruction manual using Lipofect AMINE reagent (Trademark, Gibco BRL Co., Ltd.). The cells that stably express NPY Y5 receptor were obtained.

The membrane samples prepared from the CHO cells expressing NPY Y5 receptor, the compound of the invention and 30,000 cpm $^{125}$I peptide YY (60 pM of final concentration: Amersham) were incubated in the assay buffer (20 mM HEPES-Hanks buffer containing 0.1% bovine serum albumin, pH 7.4) at 25° C. for 2 hours. The membrane samples were then filtered from the mixture through a glassfilter (GF/C) presoaked with 1% polyethyleneimine. After washing with 50 mM Tris-HCl buffer (pH 7.4), radioactivity retained on the filters was determined using gamma counter. Nonspecific binding was determined in the presence of 200 nM of peptide YY, and the 50% inhibitory concentration ($IC_{50}$ value) of the test compound against the specific peptide YY binding was calculated (Inui, A. et al. Endocrinology 131, 2090-2096 (1992)).

The compounds of the present invention inhibited the binding of peptide YY (homologue of NPY) to NPY Y5 receptor, indicating that the compounds of the present invention have an affinity for the NPY Y5 receptor (Data are not shown).

Test Example 2

Transportability Through the Blood-Brain Barrier and Drug-Drug Interactions Through P-gp To evaluate transportability of the compound of the invention through the blood-brain barrier (blood-brain partition coefficient; Kp), the concentrations of the compounds in plasma and brain after intravenous administration of the compounds (0.5 mg/2 mL/kg) were determined in mice (Jel; C57BL/6J mice, [male], 7 weeks) (data not shown). The results indicated that the compounds of the invention showed high transportability through the blood-brain barrier.

To evaluate the drug-drug interactions through P-gp in vivo, the brain Kp value of the compounds in the presence of P-gp inhibitor cyclosporin A (20 mg/kg) was determined ($Kp_{CSA}$), and the value was compared with that of control group ($Kp_{cont}$) (data not shown). The results indicated that the compound of the invention has no significant potential for drug-drug interactions through P-gp.

Test Example 3

NPY Y5 Receptor Selectivity

Using the membrane samples prepared from Y1-expression cells (human neuroblastoma, SK-N-MC) and the membrane samples prepared from Y2-expression cells (human neuroblastoma, SMS-KAN), the experiments were carried out in a similar manner as described in Test Example 1-2 to determine the affinity of the compounds of the invention for NPY Y1 and NPY Y2 receptors (data not shown). The results indicated that the compounds of the invention have high selectivity for NPY Y5 receptor.

Formulation Example 1

Tablets

Compound of the invention 15 mg
Starch 15 mg
Lactose 15 mg
Crystalline cellulose 19 mg
Polyvinyl alcohol 3 mg
Distilled water 30 ml
Calcium stearate 3 mg The above ingredients except calcium stearate are uniformly mixed and milled to granulate, and dried to obtain a suitable size of granules. Then, the granules are added with calcium stearate and compressed to form a tablet.

Formulation Example 2

Capsules

Compound of the invention 10 mg
Magnesium stearate 10 mg
Lactose 80 mg

The above ingredients are mixed uniformly to obtain powders or fine granules, which are then filled in a capsule.

Formulation Example 3

Granules

Compound of the invention 30 g
Lactose 265 g
Magnesium Stearate 5 g

The above ingredients are mixed uniformly, and the mixture was compressed. The compressed matters are milled, granulated and sieved to obtain the desired size of granules.

INDUSTRIAL APPLICABILITY

As shown in the above Experiments, the compounds of the present invention have a NPY Y5 receptor antagonistic activity. Therefore, the compound of the present invention is useful as a medicament for diseases involving an NPY Y5 receptor such as obesity.

The invention claimed is:

1. A pharmaceutical composition, comprising a compound of the formula (I), or a pharmaceutically acceptable salt or solvate thereof:

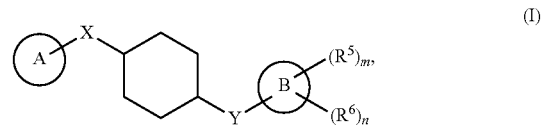

wherein

A is substituted or unsubstituted aryl or substituted or unsubstituted heterocyclyl;

the group of the formula:

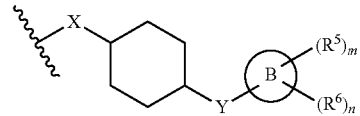

is any one of:

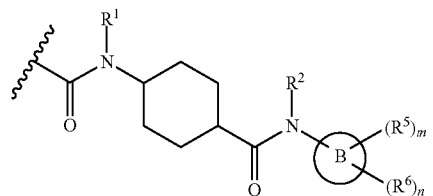

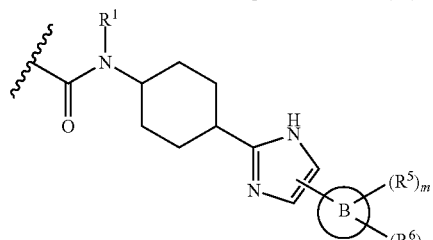

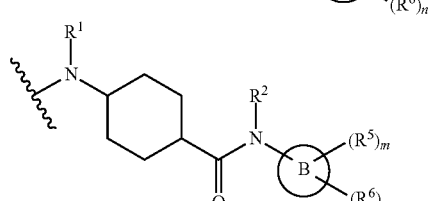

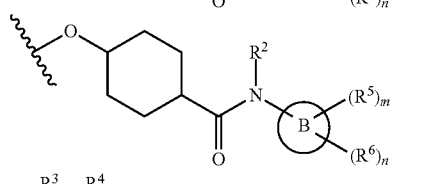

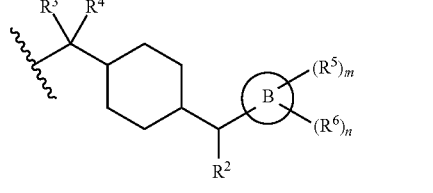

wherein
$R^1$, $R^2$, $R^3$, and $R^4$ are independently hydrogen or substituted or unsubstituted alkyl;
B is aromatic carbocycle, monocyclic heterocycle or fused bicyclic heterocycle;
$R^5$ is substituted or unsubstituted aryl or substituted or unsubstituted heterocyclyl;
$R^6$ is each independently selected from the group consisting of
halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl,
hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy,
mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio,
carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl,
formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl,
sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;
m is 0 or 1; and
n is an integer of 0 to 5,
provided that a compound wherein A is piperidino, substituted imidazolyl, substituted dihydrobenzoxazolyl, or substituted dihydroxazolopyridyl, is excluded,
wherein the composition has NPY Y5 receptor antagonistic activity.

2. The composition of claim 1, wherein the group of the formula:

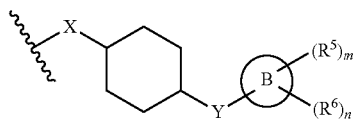

is

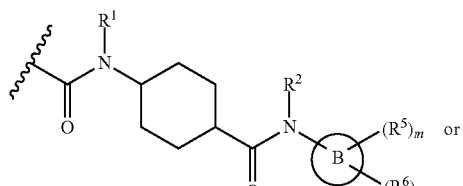

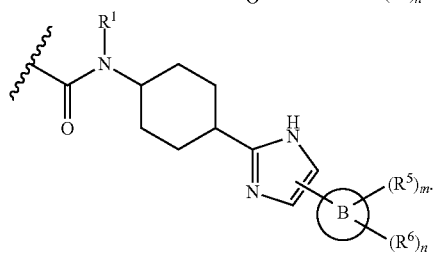

3. The composition of claim 1, wherein the group of the formula:

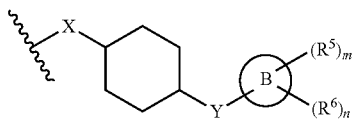

is

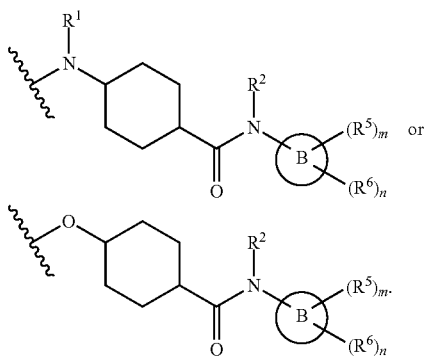

4. The composition of claim 1, wherein the group of the formula:

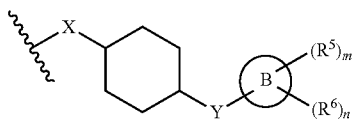

is

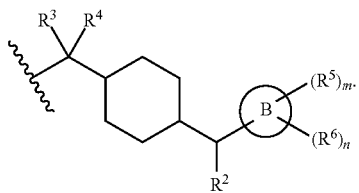

5. The composition of claim 1, wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzisothiazolyl, or substituted or unsubstituted benzoxathiazolyl.

6. The composition of claim 1, wherein B is benzene, pyrazole, imidazole, pyridine, pyradine, indazole, or dihydrobenzoxazole.

7. The composition of claim 1, wherein m is 1.

8. The composition of claim 7, wherein $R^5$ is substituted or unsubstituted phenyl, substituted or unsubstituted pyridyl, or substituted or unsubstituted morpholino.

9. The composition of claim 1, wherein n is 1 and m is 0.

10. The composition of claim 1, wherein $R^6$ is halogen, oxo, substituted or unsubstituted alkyl, substituted or unsubstituted alkoxy, or substituted or unsubstituted aryloxy.

11. A method of treating obesity or an obesity-related disease, or controlling weight in obesity, the method comprising administering to a subject in need thereof, an effective amount of the composition of claim 1.

12. A compound of formula (II), or a pharmaceutically acceptable salt or solvate thereof:

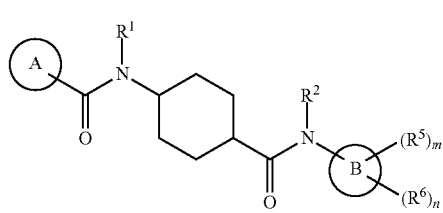

(II)

wherein
A is substituted or unsubstituted phenyl, substituted or unsubstituted thiazolyl, substituted or unsubstituted oxazolyl, substituted or unsubstituted isoxazolyl, substituted or unsubstituted pyridyl, substituted or unsubstituted naphthyridyl, or substituted or unsubstituted quinolyl;
$R^1$ and $R^2$ are independently hydrogen or substituted or unsubstituted alkyl;
B is benzene, pyrazole, pyridine, pyradine, indazole or dihydrobenzoxazole, provided that B is not benzene when A is substituted or unsubstituted phenyl;
$R^5$ is substituted or unsubstituted aryl or substituted or unsubstituted heterocyclyl;
$R^6$, in each case, is independently selected from the group consisting of
halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl,
hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy,
mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclthio,
carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl,
formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl,
sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5.

13. A compound of formula (III), or a pharmaceutically acceptable salt or solvate thereof:

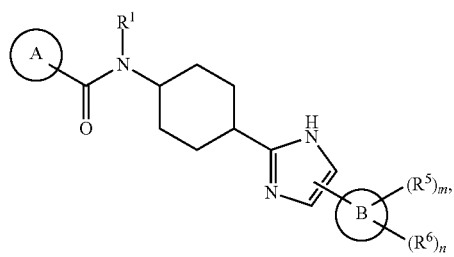

(III)

wherein
- A is substituted or unsubstituted aryl or substituted or unsubstituted heterocyclyl;
- $R^1$ is hydrogen or substituted or unsubstituted alkyl;
- B is aromatic carbocycle, monocyclic heterocycle or fused bicyclic heterocycle;
- $R^5$ is substituted or unsubstituted aryl or substituted or unsubstituted heterocyclyl;
- $R^6$ is each independently selected from the group consisting of
   halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl,
   hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy,
   mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio,
   carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl,
   formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino, m is 0 or 1; and n is an integer of 0 to 5.

14. A compound of the formula (IV), or a pharmaceutically acceptable salt or solvate thereof:

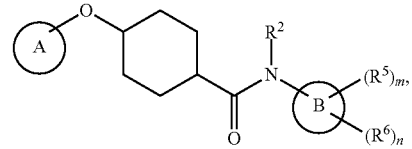

(IV)

wherein
- A is substituted or unsubstituted aryl or substituted or unsubstituted heterocyclyl;
- $R^2$ is hydrogen or substituted or unsubstituted alkyl;
- B is aromatic carbocycle, monocyclic heterocycle or fused bicyclic heterocycle;
- $R^5$ is substituted or unsubstituted aryl or substituted or unsubstituted heterocyclyl;
- each of $R^6$ is independently selected from the group consisting of
   halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl,
   hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy,
   mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio,
   carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl,
   formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl, and substituted or unsubstituted amino;

m is 0 or 1; and n is an integer of 0 to 5.

15. A pharmaceutical composition, comprising the compound, salt, or solvate of claim 12.

16. The composition of claim 2, wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzisothiazolyl, or substituted or unsubstituted benzoxathiazolyl.

17. The composition of claim 3, wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzisothiazolyl, or substituted or unsubstituted benzoxathiazolyl.

18. The composition of claim 4, wherein A is substituted or unsubstituted phenyl, substituted or unsubstituted thiazolyl, substituted or unsubstituted oxazolyl, substituted or unsubstituted isoxazolyl, substituted or unsubstituted triazolyl, substituted or unsubstituted oxathiazolidyl, substituted or unsubstituted pyridyl, substituted or unsubstituted pyradyl, substituted or unsubstituted naphthyridyl, substituted or unsubstituted quinolyl, substituted or unsubstituted benzoimidazolyl, substituted or unsubstituted dihydrobenzisothiazolyl, or substituted or unsubstituted benzoxathiazolyl.

* * * * *